United States Patent
Haap et al.

(10) Patent No.: US 10,172,843 B2
(45) Date of Patent: Jan. 8, 2019

(54) PIPERIDINE DERIVATIVES

(71) Applicant: Hoffmann-La Roche Inc., Little Falls, NJ (US)

(72) Inventors: Wolfgang Haap, Loerrach (DE); Holger Kuehne, Loerrach (DE); Harald Mauser, Riehen (CH)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 15/612,123

(22) Filed: Jun. 2, 2017

(65) Prior Publication Data

US 2017/0266175 A1 Sep. 21, 2017

Related U.S. Application Data

(63) Continuation of application No. PCT/EP2015/078026, filed on Nov. 30, 2015.

(30) Foreign Application Priority Data

Dec. 2, 2014 (EP) ..................... 14195778

(51) Int. Cl.

| | |
|---|---|
| *C07D 401/14* | (2006.01) |
| *C07D 471/04* | (2006.01) |
| *A61K 31/4523* | (2006.01) |
| *C07D 413/14* | (2006.01) |
| *C07D 403/14* | (2006.01) |
| *C07D 417/14* | (2006.01) |
| *A61K 31/38* | (2006.01) |
| *C07C 19/08* | (2006.01) |
| *C07C 317/02* | (2006.01) |
| *C07D 233/20* | (2006.01) |
| *C07D 265/02* | (2006.01) |
| *A61K 31/445* | (2006.01) |

(52) U.S. Cl.
CPC .......... *A61K 31/4523* (2013.01); *A61K 31/38* (2013.01); *C07C 19/08* (2013.01); *C07C 317/02* (2013.01); *C07D 233/20* (2013.01); *C07D 265/02* (2013.01); *C07D 401/14* (2013.01); *C07D 403/14* (2013.01); *C07D 413/14* (2013.01); *C07D 417/14* (2013.01); *C07D 471/04* (2013.01); *A61K 31/445* (2013.01)

(58) Field of Classification Search
CPC ............................ C07D 401/14; C07D 471/04
See application file for complete search history.

(56) References Cited

FOREIGN PATENT DOCUMENTS

| | | |
|---|---|---|
| EP | 2 668 951 A1 | 4/2013 |
| WO | 2013/076063 A1 | 5/2013 |

OTHER PUBLICATIONS

Albert et al., "An Integrated Approach to Fragment-Based Lead Generation: Philosophy, Strategy and Case Studies from AstraZeneca's Drug Discovery Programmes" Current Topics in Medicinal Chemistry 7(16):1600-1629 (Jan. 1, 2007).
Lee-Dutra et al., "Cathepsin S inhibitors: 2004-2010" Expert Opinion on Therapeutic Patents 21(3):311-337 (Mar. 1, 2011).

*Primary Examiner* — Brian E McDowell
(74) *Attorney, Agent, or Firm* — Jonathan Duffield

(57) ABSTRACT

The invention relates to a compound of formula (I)

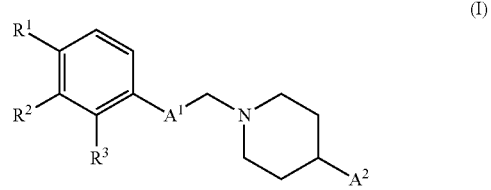

wherein $A^1$, $A^2$ and $R^1$ to $R^3$ are defined as in the description and in the claims. The compound of formula (I) can be used as a medicament.

14 Claims, No Drawings

PIPERIDINE DERIVATIVES

The present invention relates to organic compounds useful for therapy and/or prophylaxis in a mammal, and in particular to compounds that are preferential inhibitors of the cysteine protease cathepsin, in particular of the cysteine protease cathepsin S.

The invention relates in particular to a compound of formula (I)

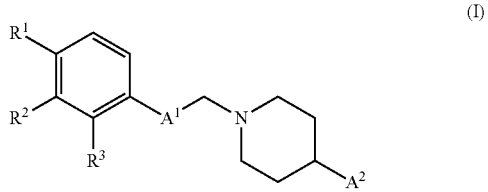

wherein
$R^1$ is haloalkylsulfonyl, haloalkyl, alkylsulfonyl, phenylalkylsulfonyl, halogen or alkyl;
$R^2$ is hydrogen or halogen;
$R^3$ is hydrogen or halogen;
$A^1$ is heterocyclyl or substituted heterocyclyl, wherein heterocyclyl is 1H-imidazolyl, 1H-[1,2,4]triazolyl, thiazolyl, oxazolyl or 1H-pyrazolyl and wherein substituted heterocyclyl is heterocyclyl substituted with one or two substituents independently selected from alkyl, phenyl, phenylalkyl and alkoxyalkyl;
$A^2$ is heterocyclyl or substituted heterocyclyl, wherein heterocyclyl is oxodihydroquinazolinyl, oxodihydrobenzoimidazolyl, 1H-pyrrolopyridine, oxodihydroindolyl, benzoimidazol-1-yl, 3-oxo-4H-benzo[1,4]oxazinyl, oxo-1H-imidazolyl, benzo[d]isoxazolyl, oxo-4H-[1,2,4]triazolyl, oxo-5H-imidazopyridinyl or oxopiperidinyl and wherein substituted heterocyclyl is heterocyclyl substituted with one or two substituents independently selected from alkyl, halogen, alkoxycarbonylalkyl, alkoxyalkyl, pyrrolidinyl, hydroxyalkyl, alkylcarbonyloxyalkyl, alkyl sulfonyl alkyl, morpholinyl, aminocarbonylalkyl, alkylaminocarbonylalkyl, alkylpiperazinyl, halophenyl and carboxyalkyl;
or a pharmaceutically acceptable salt or ester thereof.

The compounds of the invention are preferential inhibitors of the cysteine protease Cathepsin (Cat), in particular Cathepsin S and are therefore useful to treat metabolic diseases like diabetes, atherosclerosis, abdominal aortic aneurysm, peripheral arterial disease, cancer, reduction of cardiovascular events in chronic kidney disease and diabetic nephropathy. In addition, immune mediated diseases like rheumatoid arthritis, multiple sclerosis, sjorgen syndrome, lupus erythematosus, neuropathic pain, diabetes type I, asthma and allergy and skin related immune disease are suitable diseases to be treated with a cathepsin S inhibitor.

Objects of the present invention are the compounds of formula (I) and their aforementioned salts per se and their use as therapeutically active substances, a process for the manufacture of the said compounds, intermediates, pharmaceutical compositions, medicaments containing the said compounds, their pharmaceutically acceptable salts, the use of the said compounds and salts for the prophylaxis and/or therapy of illnesses, especially in the treatment or prophylaxis of diabetes, atherosclerosis, abdominal aortic aneurysm, peripheral arterial disease, cancer, reduction of cardiovascular events in chronic kidney disease and diabetic nephropathy, and the use of the said compounds and salts for the production of medicaments for the treatment or prophylaxis of diabetes, atherosclerosis, abdominal aortic aneurysm, peripheral arterial disease, cancer, reduction of cardiovascular events in chronic kidney disease and diabetic nephropathy.

Mammalian cathepsins are cysteine-type proteases involved in key steps of biological and pathological events. Cathepsins are considered tractable drug targets as it is feasible to inhibit enzymatic activity with small molecules and are therefore of interest to the pharmaceutical industry (Bromme, D. (2001), 'Papain-like cysteine proteases', Curr Protoc Protein Sci, Chapter 21, Unit 21 2; Roberts, R. (2005), 'Lysosomal cysteine proteases: structure, function and inhibition of cathepsins', Drug News Perspect, 18 (10), 605-14).

Cathepsin S is prominently expressed in antigen presenting cells like macrophages and dendritic cells and smooth muscle cells (Hsing, L. C. and Rudensky, A. Y. (2005), 'The lysosomal cysteine proteases in MHC class II antigen presentation', Immunol Rev, 207, 229-41; Rudensky, A. and Beers, C. (2006), 'Lysosomal cysteine proteases and antigen presentation', Ernst Schering Res Found Workshop, (56), 81-95). While Cathepsin S is only weakly expressed in normal arterial tissue, strong upregulation is seen in atherosclerotic arteries (Liu, J., et al. (2006), 'Increased serum cathepsin S in patients with atherosclerosis and diabetes', Atherosclerosis, 186 (2), 411-9; Sukhova, G. K., et al. (1998), 'Expression of the elastolytic cathepsins S and K in human atheroma and regulation of their production in smooth muscle cells', J Clin Invest, 102 (3), 576-83).

Preclinical data suggest that the function of Cathepsin S is critical for atherosclerosis as Cathepsin S deficient mice have a reduced atherosclerosis-phenotype when tested in appropriate mouse models. In LDL-Rec deficient mice reduced lipid accumulation, elastin-fibre breakdown and chronic arterial inflammation is reported. In APO E deficient mice a significant reduction of acute plaque rupture events was reported. When chronic renal disease is introduced into CatS/In APO-E deficient mice a strong reduction of accelerated calcification is seen on top of the anti atherosclerotic activity in arteries and heart valves (Aikawa, E., et al. (2009), 'Arterial and aortic valve calcification abolished by elastolytic cathepsin S deficiency in chronic renal disease', Circulation, 119 (13), 1785-94; de Nooijer, R., et al. (2009), 'Leukocyte cathepsin S is a potent regulator of both cell and matrix turnover in advanced atherosclerosis', Arterioscler Thromb Vasc Biol, 29 (2), 188-94; Rodgers, K. J., et al. (2006), 'Destabilizing role of cathepsin S in murine atherosclerotic plaques', Arterioscler Thromb Vasc Biol, 26 (4), 851-6; Sukhova, G. K., et al. (2003), 'Deficiency of cathepsin S reduces atherosclerosis in LDL receptor-deficient mice', J Clin Invest, 111 (6), 897-906). This suggests a potential inhibitor of Cathepsin S would stabilise atherosclerotic plaque by reducing extracellular matrix breakdown, by reducing the proinflammatory state and by reducing accelerated calcification and subsequently its clinical manifestations.

These phenotypes described in atherosclerosis models are in agreement with known cellular functions of Cathepsin S. Firstly, Cathepsin S is involved in the degradation of extracellular matrix that stabilises the plaque. In particular, Cathepsin S has potent elastinolytic activity and can exert this at neutral pH, a feature that distinguishes Cathepsin S from all other Cathepsins. Secondly, Cathepsin S is the major protease involved in antigen processing, in particular cleavage of the invariant chain in antigen presenting cells, resulting in reduced contribution of Tcells to the chronic inflammation of the atherosclerotic tissue. Elevated inflammation results in further oxidative and proteolytic tissue damage and subsequently plaque destabilisation (Cheng, X. W., et al. (2004), 'Increased expression of elastolytic cysteine proteases, cathepsins S and K, in the neointima of balloon-injured rat carotid arteries', Am J Pathol, 164 (1), 243-51; Driessen, C., et al. (1999), 'Cathepsin S controls the trafficking and maturation of MEW class II molecules in dendritic cells', J Cell Biol, 147 (4), 775-90; Rudensky, A. and Beers, C. (2006), 'Lysosomal cysteine proteases and antigen presentation', Ernst Schering Res Found Workshop, (56), 81-95).

The anti-inflammatory and anti-elastinolytic properties of a Cat S inhibitor make it also a prominent target for chronic obstructive pulmonary disease (Williams, A. S., et al. (2009), 'Role of cathepsin S in ozone-induced airway hyperresponsiveness and inflammation', Pulm Pharmacol Ther, 22 (1), 27-32). Furthermore due to its extracellular functions in matrix degradation, inhibition of cathepsin S will impact neointima formation and angiogenesis (Burns-Kurtis, C. L., et al. (2004), 'Cathepsin S expression is up-regulated following balloon angioplasty in the hypercholesterolemic rabbit', Cardiovasc Res, 62 (3), 610-20; Cheng, X. W., et al. (2004), 'Increased expression of elastolytic cysteine proteases, cathepsins S and K, in the neointima of balloon-injured rat carotid arteries', Am J Pathol, 164 (1), 243-51; Shi, G. P., et al. (2003), 'Deficiency of the cysteine protease cathepsin S impairs microvessel growth', Circ Res, 92 (5), 493-500; Wang, B., et al. (2006), 'Cathepsin S controls angiogenesis and tumor growth via matrix-derived angiogenic factors', J Biol Chem, 281 (9), 6020-9). An inhibitor of Cathepsin S might therefore be useful in several different disease settings.

Cathepsin S plays also a role in the reduction of tumor growth and tumor cell invasion as described by Roberta E. Burden in Clin Cancer Res 2009; 15(19). In addition, nephrectomized Cathepsin S knock out mice showed a significant reduction of arterial calcification when compared to nephrectomized wild type mice. This indicates that inhibition of Cathepsin S may have a beneficial effect on the reduction of cardiovascular events in chronic kidney disease patients (Elena Aikawa, Circulation, 2009, 1785-1794).

In the present description the term "alkyl", alone or in combination, signifies a straight-chain or branched-chain alkyl group with 1 to 8 carbon atoms, particularly a straight or branched-chain alkyl group with 1 to 6 carbon atoms and more particularly a straight or branched-chain alkyl group with 1 to 4 carbon atoms. Examples of straight-chain and branched-chain C1-C8 alkyl groups are methyl, ethyl, propyl, isopropyl, butyl, isobutyl, tert.-butyl, the isomeric pentyls, the isomeric hexyls, the isomeric heptyls and the isomeric octyls, particularly methyl, ethyl, propyl, butyl and pentyl. Particular examples of alkyl are methyl, ethyl and propyl.

The term "alkoxy", alone or in combination, signifies a group of the formula alkyl-O— in which the term "alkyl" has the previously given significance, such as methoxy, ethoxy, n-propoxy, isopropoxy, n-butoxy, isobutoxy, sec-butoxy and tert.-butoxy. A particular "alkoxy" is methoxy.

The terms "halogen" or "halo", alone or in combination, signifies fluorine, chlorine, bromine or iodine and particularly fluorine, chlorine or bromine, more particularly fluorine and chlorine, and more particularly chlorine. The term "halo", in combination with another group, denotes the substitution of said group with at least one halogen, particularly substituted with one to five halogens, particularly one to three halogens, i.e. one, two or three halogens. A particular "haloalkyl" is trifluoromethyl.

The terms "hydroxyl" and "hydroxy", alone or in combination, signify the —OH group.

The term "sulfonyl", alone or in combination, signifies the —SO$_2$— group.

The term "amino", alone or in combination, signifies the primary amino group (—NH$_2$), the secondary amino group (—NH—) or the tertiary amino group (—N—).

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid, particularly hydrochloric acid, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein. In addition these salts may be prepared form addition of an inorganic base or an organic base to the free acid. Salts derived from an inorganic base include, but are not limited to, the sodium, potassium, lithium, ammonium, calcium, magnesium salts. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyamine resins. The compound of formula (I) can also be present in the form of zwitterions. Particularly preferred pharmaceutically acceptable salts of compounds of formula (I) are the salts of hydrochloric acid, hydrobromic acid, sulfuric acid, phosphoric acid and methanesulfonic acid.

"Pharmaceutically acceptable esters" means that the compound of general formula (I) may be derivatised at functional groups to provide derivatives which are capable of conversion back to the parent compounds in vivo. Examples of such compounds include physiologically acceptable and metabolically labile ester derivatives, such as methoxymethyl esters, methylthiomethyl esters and pivaloyloxymethyl esters. Additionally, any physiologically acceptable equivalents of the compound of general formula (I), similar to the metabolically labile esters, which are capable of producing the parent compound of general formula (I) in vivo, are within the scope of this invention.

If one of the starting materials or compounds of formula (I) contain one or more functional groups which are not stable or are reactive under the reaction conditions of one or more reaction steps, appropriate protecting groups (as described e.g. in "Protective Groups in Organic Chemistry" by T. W. Greene and P. G. M. Wuts, 3$^{rd}$ Ed 1999, Wiley, New York) can be introduced before the critical step applying methods well known in the art. Such protecting groups can be removed at a later stage of the synthesis using standard methods described in the literature. Examples of protecting groups are tert-butoxycarbonyl (Boc), 9-fluorenylmethyl carbamate (Fmoc), 2-trimethylsilylethyl carbamate (Teoc), carbobenzyloxy (Cbz) and p-methoxybenzyloxycarbonyl (Moz).

The compound of formula (I) can contain several asymmetric centers and can be present in the form of optically pure enantiomers, mixtures of enantiomers such as, for example, racemates, mixtures of diastereoisomers, diastereoisomeric racemates or mixtures of diastereoisomeric racemates.

The term "asymmetric carbon atom" means a carbon atom with four different substituents. According to the Cahn-Ingold-Prelog Convention an asymmetric carbon atom can be of the "R" or "S" configuration.

In the definition of heterocycle in $A^1$, it is preferred that 1H-imidazolyl is not unsubstituted. And it is further preferred that substituted 1H-imidazolyl is alkyl-1H-imidazolyl or dialkyl-1H-imidazolyl, preferably methyl-1H-imidazolyl or dimethyl-1H-imidazolyl. Alkyl-1H-imidazolyl and methyl-1H-imidazolyl are in that case particularly preferred.

The invention relates in particular to:

A compound of formula (I) wherein $R^1$ is haloalkylsulfonyl, haloalkyl or alkylsulfonyl;

A compound of formula (I) wherein $R^1$ is trifluoromethylsulfonyl, trifluoromethyl or methyl sulfonyl;

A compound of formula (I) wherein $R^2$ is hydrogen or chloro;

A compound of formula (I) wherein $R^4$ is hydrogen;

A compound of formula (I) wherein $A^1$ is alkylthiazolyl, heterocyclyl or substituted heterocyclyl, wherein heterocyclyl is 1H-imidazolyl, 1H-[1,2,4]triazolyl, oxazolyl or 1H-pyrazolyl and wherein substituted heterocyclyl is heterocyclyl substituted with one or two substituents independently selected from alkyl, phenyl, phenylalkyl and alkoxyalkyl;

A compound of formula (I) wherein $A^1$ is alkyl-1H-imidazolyl or dialkyl-1H-imidazolyl;

A compound of formula (I) wherein $A^1$ is methyl-1H-imidazolyl, propyl-1H-imidazolyl or dimethyl-1H-imidazolyl;

A compound of formula (I) wherein $A^2$ is oxodihydroquinazolinyl, alkyloxodihydrobenzoimidazolyl, (alkylpyrrolidinyl)oxodihydrobenzoimidazolyl or 1H-pyrrolopyridine; and A compound of formula (I) wherein $A^2$ is oxodihydroquinazolinyl, methyloxodihydrobenzoimidazolyl, (methylpyrrolidinyl)oxodihydrobenzoimidazolyl or 1H-pyrrolopyridine.

The invention furthermore relates to a compound of formula (I) selected from

3-{1-[5-Methyl-2-(4-trifluoromethanesulfonyl-phenyl)-1H-imidazol-4-ylmethyl]-piperidin-4-yl}-3,4-dihydro-1H-quinazolin-2-one;

1-Methyl-3-{1-[5-methyl-2-(4-trifluoromethanesulfonyl-phenyl)-1H-imidazol-4-ylmethyl]-piperidin-4-yl}-1,3-dihydro-benzoimidazol-2-one;

3-{1-[2-(3-Chloro-4-trifluoromethyl-phenyl)-5-methyl-1H-imidazol-4-ylmethyl]-piperidin-4-yl}-3,4-dihydro-1H-quinazolin-2-one;

3-{1-[1,5-Dimethyl-2-(4-trifluoromethyl-phenyl)-1H-imidazol-4-ylmethyl]-piperidin-4-yl}-3,4-dihydro-1H-quinazolin-2-one;

3-{1-[2-(4-Methanesulfonyl-phenyl)-5-methyl-1H-imidazol-4-ylmethyl]-piperidin-4-yl}-3,4-dihydro-1H-quinazolin-2-one;

3-{1-[5-Methyl-2-(4-phenylmethanesulfonyl-phenyl)-1H-imidazol-4-ylmethyl]-piperidin-4-yl}-3,4-dihydro-1H-quinazolin-2-one;

3-{1-[2-(3-Chloro-4-trifluoromethyl-phenyl)-5-methyl-1H-imidazol-4-ylmethyl]-piperidin-4-yl}-7-fluoro-3,4-dihydro-1H-quinazolin-2-one;

(6-Chloro-3-{1-[5-methyl-2-(4-trifluoromethyl-phenyl)-1H-imidazol-4-ylmethyl]-piperidin-4-yl}-2-oxo-2,3-dihydro-benzoimidazol-1-yl)-acetic acid methyl ester;

1-(2-Methoxy-ethyl)-3-{1-[5-methyl-2-(4-trifluoromethyl-phenyl)-1H-imidazol-4-ylmethyl]-piperidin-4-yl}-3,4-dihydro-1H-quinazolin-2-one;

1-Methyl-3-{1-[5-methyl-2-(4-trifluoromethyl-phenyl)-1H-imidazol-4-ylmethyl]-piperidin-4-yl}-3,4-dihydro-1H-quinazolin-2-one;

3-{1-[2-(3-Fluoro-4-trifluoromethyl-phenyl)-5-methyl-1H-imidazol-4-ylmethyl]-piperidin-4-yl}-3,4-dihydro-1H-quinazolin-2-one;

5-Chloro-3-ethyl-1-{1-[5-methyl-2-(4-trifluoromethyl-phenyl)-1H-imidazol-4-ylmethyl]-piperidin-4-yl}-1,3-dihydro-benzoimidazol-2-one;

3-{1-[5-Methyl-2-(4-trifluoromethanesulfonyl-phenyl)-1H-imidazol-4-ylmethyl]-piperidin-4-yl}-1H-pyrrolo[3,2-c]pyridine;

1-Methyl-3-{1-[5-methyl-2-(4-phenylmethanesulfonyl-phenyl)-1H-imidazol-4-ylmethyl]-piperidin-4-yl}-1,3-dihydro-benzoimidazol-2-one;

1-{1-[2-(4-Methanesulfonyl-phenyl)-5-methyl-1H-imidazol-4-ylmethyl]-piperidin-4-yl}-3-methyl-1,3-dihydro-benzoimidazol-2-one;

7-Fluoro-3-{1-[5-methyl-2-(4-trifluoromethyl-phenyl)-1H-imidazol-4-ylmethyl]-piperidin-4-yl}-3,4-dihydro-1H-quinazolin-2-one;

1-{1-[5-Methyl-2-(4-trifluoromethyl-phenyl)-1H-imidazol-4-ylmethyl]-piperidin-4-yl}-6-pyrrolidin-1-yl-1,3-dihydro-benzoimidazol-2-one;

3-{1-[5-Methyl-2-(4-trifluoromethyl-phenyl)-1H-imidazol-4-ylmethyl]-piperidin-4-yl}-3,4-dihydro-1H-quinazolin-2-one;

5-Chloro-3-methyl-1-{1-[5-methyl-2-(4-trifluoromethyl-phenyl)-1H-imidazol-4-ylmethyl]-piperidin-4-yl}-1,3-dihydro-benzoimidazol-2-one;

6-Bromo-3-[1-[[2-[4-(trifluoromethyl)phenyl]-1H-imidazol-5-yl]methyl]-4-piperidyl]-1,4-dihydroquinazolin-2-one;

5-Chloro-3-(2-methoxy-ethyl)-1-{1-[5-methyl-2-(4-trifluoromethyl-phenyl)-1H-imidazol-4-ylmethyl]-piperidin-4-yl}-1,3-dihydro-benzoimidazol-2-one;

3-{1-[5-Benzyl-2-(4-trifluoromethyl-phenyl)-1H-imidazol-4-ylmethyl]-piperidin-4-yl}-3,4-dihydro-1H-quinazolin-2-one;

5-Chloro-3-(2-hydroxy-ethyl)-1-{1-[5-methyl-2-(4-trifluoromethyl-phenyl)-1H-imidazol-4-ylmethyl]-piperidin-4-yl}-1,3-dihydro-benzoimidazol-2-one;

1-{1-[2-(3-Chloro-4-trifluoromethyl-phenyl)-5-methyl-1H-imidazol-4-ylmethyl]-piperidin-4-yl}-3-methyl-1,3-dihydro-benzoimidazol-2-one;

5-Chloro-1-{1-[5-methyl-2-(4-trifluoromethyl-phenyl)-1H-imidazol-4-ylmethyl]-piperidin-4-yl}-1,3-dihydro-benzoimidazol-2-one;

1-{1-[1,5-Dimethyl-2-(4-trifluoromethyl-phenyl)-1H-imidazol-4-ylmethyl]-piperidin-4-yl}-3-methyl-1,3-dihydro-benzoimidazol-2-one;

5-Chloro-3-(2-methanesulfonyl-ethyl)-1-{1-[5-methyl-2-(4-trifluoromethyl-phenyl)-1H-imidazol-4-ylmethyl]-piperidin-4-yl}-1,3-dihydro-benzoimidazol-2-one;

Acetic acid 2-(6-chloro-3-{1-[5-methyl-2-(4-trifluoromethyl-phenyl)-1H-imidazol-4-ylmethyl]-piperidin-4-yl}-2-oxo-2,3-dihydro-benzoimidazol-1-yl)-ethyl ester;

1-Methyl-3-{1-[5-methyl-2-(4-trifluoromethyl-phenyl)-1H-imidazol-4-ylmethyl]-piperidin-4-yl}-1,3-dihydro-benzoimidazol-2-one;

3-{1-[2-(2-Chloro-4-trifluoromethyl-phenyl)-5-methyl-1H-imidazol-4-ylmethyl]-piperidin-4-yl}-3,4-dihydro-1H-quinazolin-2-one;

1-{1-[5-Methyl-2-(4-trifluoromethyl-phenyl)-1H-imidazol-4-ylmethyl]-piperidin-4-yl}-6-morpholin-4-yl-1,3-dihydro-benzoimidazol-2-one;

3-{1-[2-(3,4-Dichloro-phenyl)-5-methyl-1H-imidazol-4-ylmethyl]-piperidin-4-yl}-3,4-dihydro-1H-quinazolin-2-one;

3-{1-[5-Propyl-2-(4-trifluoromethyl-phenyl)-1H-imidazol-4-ylmethyl]-piperidin-4-yl}-3,4-dihydro-1H-quinazolin-2-one;

3-{1-[2-(3-Chloro-4-trifluoromethyl-phenyl)-5-methyl-1H-imidazol-4-ylmethyl]-piperidin-4-yl}-1H-pyrrolo[2,3-b]pyridine;

2-(6-Chloro-3-{1-[5-methyl-2-(4-trifluoromethyl-phenyl)-1H-imidazol-4-ylmethyl]-piperidin-4-yl}-2-oxo-2,3-dihydro-benzoimidazol-1-yl)-acetamide;

3-{1-[1-(2-Methoxy-ethyl)-5-methyl-2-(4-trifluoromethyl-phenyl)-1H-imidazol-4-ylmethyl]-piperidin-4-yl}-3,4-dihydro-1H-quinazolin-2-one;

2-(6-Chloro-3-{1-[5-methyl-2-(4-trifluoromethyl-phenyl)-1H-imidazol-4-ylmethyl]-piperidin-4-yl}-2-oxo-2,3-dihydro-benzoimidazol-1-yl)-N-methyl-acetamide;

3-{1-[5-(2-Methoxy-ethyl)-2-(4-trifluoromethyl-phenyl)-1H-imidazol-4-ylmethyl]-piperidin-4-yl}-3,4-dihydro-1H-quinazolin-2-one;

1-{1-[2-(3-Fluoro-4-trifluoromethyl-phenyl)-5-methyl-1H-imidazol-4-ylmethyl]-piperidin-4-yl}-3-methyl-1,3-dihydro-benzoimidazol-2-one;

1-{1-[5-Methyl-2-(4-trifluoromethyl-phenyl)-1H-imidazol-4-ylmethyl]-piperidin-4-yl}-1,3-dihydro-benzoimidazol-2-one;

5-Chloro-1-{1-[5-methyl-2-(4-trifluoromethyl-phenyl)-1H-imidazol-4-ylmethyl]-piperidin-4-yl}-1,3-dihydro-indol-2-one;

3-{1-[1-Methyl-5-(4-trifluoromethyl-phenyl)-1H-[1,2,4]triazol-3-ylmethyl]-piperidin-4-yl}-3,4-dihydro-1H-quinazolin-2-one;

1-{1-[5-Methyl-2-(4-trifluoromethyl-phenyl)-1H-imidazol-4-ylmethyl]-piperidin-4-yl}-1H-benzoimidazole;

3-{1-[2-(3,4-Dichloro-phenyl)-5-methyl-1H-imidazol-4-ylmethyl]-piperidin-4-yl}-7-fluoro-3,4-dihydro-1H-quinazolin-2-one;

6-(4-Methyl-piperazin-1-yl)-1-{1-[5-methyl-2-(4-trifluoromethyl-phenyl)-1H-imidazol-4-ylmethyl]-piperidin-4-yl}-1,3-dihydro-benzoimidazol-2-one;

4-{1-[5-Methyl-2-(4-trifluoromethyl-phenyl)-1H-imidazol-4-ylmethyl]-piperidin-4-yl}-4H-benzo[1,4]oxazin-3-one;

3-{1-[5-Methyl-2-(4-trifluoromethyl-phenyl)-1H-imidazol-4-ylmethyl]-piperidin-4-yl}-1H-pyrrolo[2,3-b]pyridine;

1-Methyl-3-{1-[2-methyl-5-(4-trifluoromethyl-phenyl)-2H-[1,2,4]triazol-3-ylmethyl]-piperidin-4-yl}-1,3-dihydro-benzoimidazol-2-one;

5-(4-Bromophenyl)-3-[1-[[4-methyl-2-[4-(trifluoromethyl)phenyl]-1H-imidazol-5-yl]methyl]-4-piperidyl]-1H-imidazol-2-one;

6-Fluoro-3-{1-[5-methyl-2-(4-trifluoromethyl-phenyl)-1H-imidazol-4-ylmethyl]-piperidin-4-yl}-benzo[d]isoxazole;

3-{1-[2-(4-Chloro-3-fluoro-phenyl)-5-methyl-1H-imidazol-4-ylmethyl]-piperidin-4-yl}-3,4-dihydro-1H-quinazolin-2-one;

3-{1-[4-Methyl-1-(4-trifluoromethyl-phenyl)-1H-pyrazol-3-ylmethyl]-piperidin-4-yl}-3,4-dihydro-1H-quinazolin-2-one;

3-{1-[5-Methyl-2-(4-trifluoromethyl-phenyl)-1H-imidazol-4-ylmethyl]-piperidin-4-yl}-1H-pyrrolo[3,2-c]pyridine;

3-{1-[5-Methyl-2-(4-trifluoromethyl-phenyl)-1H-imidazol-4-ylmethyl]-piperidin-4-yl}-1H-indole;

1-{1-[5-Methyl-2-(4-trifluoromethyl-phenyl)-1H-imidazol-4-ylmethyl]-piperidin-4-yl}-1,3-dihydro-indol-2-one;

1-{1-[2-(3,4-Dichloro-phenyl)-5-methyl-1H-imidazol-4-ylmethyl]-piperidin-4-yl}-3-methyl-1,3-dihydro-benzoimidazol-2-one;

1-{1-[2-(2-Chloro-4-trifluoromethyl-phenyl)-5-methyl-1H-imidazol-4-ylmethyl]-piperidin-4-yl}-3-methyl-1,3-dihydro-benzoimidazol-2-one;

1-Methyl-3-{1-[5-propyl-2-(4-trifluoromethyl-phenyl)-1H-imidazol-4-ylmethyl]-piperidin-4-yl}-1,3-dihydro-benzoimidazol-2-one;

Sodium; (6-chloro-3-{1-[5-methyl-2-(4-trifluoromethyl-phenyl)-1H-imidazol-4-ylmethyl]-piperidin-4-yl}-2-oxo-2,3-dihydro-benzoimidazol-1-yl)-acetate;

1-Methyl-3-{1-[5-phenyl-2-(4-trifluoromethyl-phenyl)-1H-imidazol-4-ylmethyl]-piperidin-4-yl}-1,3-dihydro-benzoimidazol-2-one;

3-{1-[2-(2,4-Dichloro-phenyl)-5-methyl-1H-imidazol-4-ylmethyl]-piperidin-4-yl}-3,4-dihydro-1H-quinazolin-2-one;

5-Chloro-1-{1-[2-(3-chloro-4-methyl-phenyl)-5-methyl-1H-imidazol-4-ylmethyl]-piperidin-4-yl}-1,3-dihydro-benzoimidazol-2-one;

5-Chloro-1-{1-[2-(4-chloro-phenyl)-5-methyl-1H-imidazol-4-ylmethyl]-piperidin-4-yl}-1,3-dihydro-benzoimidazol-2-one;

3-(1-{5-Methyl-2-[4-(2-methyl-propane-1-sulfonyl)-phenyl]-1H-imidazol-4-ylmethyl}-piperidin-4-yl)-3,4-dihydro-1H-quinazolin-2-one;

3-{1-[2-(3,4-Dichloro-phenyl)-5-methyl-1H-imidazol-4-ylmethyl]-piperidin-4-yl}-1H-pyrrolo[2,3-b]pyridine;

3-{1-[3-Methyl-1-(4-trifluoromethyl-phenyl)-1H-pyrazol-4-ylmethyl]-piperidin-4-yl}-3,4-dihydro-1H-quinazolin-2-one;

1-Methyl-3-{1-[1-methyl-5-(4-trifluoromethyl-phenyl)-1H-[1,2,4]triazol-3-ylmethyl]-piperidin-4-yl}-1,3-dihydro-benzoimidazol-2-one;

5-(4-Bromophenyl)-2-[1-[[2-[4-(trifluoromethyl)phenyl]-1H-imidazol-5-yl]methyl]-4-piperidyl]-4H-1,2,4-triazol-3-one;

1-Methyl-3-{1-[4-methyl-1-(4-trifluoromethyl-phenyl)-1H-pyrazol-3-ylmethyl]-piperidin-4-yl}-1,3-dihydro-benzoimidazol-2-one;

1-{1-[2-(4-Chloro-3-fluoro-phenyl)-5-methyl-1H-imidazol-4-ylmethyl]-piperidin-4-yl}-3-methyl-1,3-dihydro-benzoimidazol-2-one;

3-{1-[5-(2-Methoxy-ethyl)-2-(4-trifluoromethyl-phenyl)-1H-imidazol-4-ylmethyl]-piperidin-4-yl}-1H-pyrrolo[3,2-c]pyridine;

5-Chloro-1-{1-[2-(3-fluoro-4-methyl-phenyl)-5-methyl-1H-imidazol-4-ylmethyl]-piperidin-4-yl}-1,3-dihydro-benzoimidazol-2-one;

1-Methyl-3-{1-[5-methyl-2-(4-trifluoromethyl-phenyl)-thiazol-4-ylmethyl]-piperidin-4-yl}-1,3-dihydro-benzoimidazol-2-one;

1-Methyl-3-{1-[5-methyl-2-(4-trifluoromethyl-phenyl)-oxazol-4-ylmethyl]-piperidin-4-yl}-1,3-dihydro-benzoimidazol-2-one;

1-[1-[[4-Methyl-2-[4-(trifluoromethyl)phenyl]-1H-imidazol-5-yl]methyl]-4-piperidyl]-5H-imidazo[4,5-c]pyridin-4-one;

1-Methyl-3-(1-{5-methyl-2-[4-(2-methyl-propane-1-sulfonyl)-phenyl]-1H-imidazol-4-ylmethyl}-piperidin-4-yl)-1,3-dihydro-benzoimidazol-2-one;

1-[1-[[4-Methyl-2-[4-(trifluoromethyl)phenyl]-1H-imidazol-5-yl]methyl]-4-piperidyl]piperidin-2-one;

1-{1-[2-(2,4-Dichloro-phenyl)-5-methyl-1H-imidazol-4-yl-methyl]-piperidin-4-yl}-3-methyl-1,3-dihydro-benzoimidazol-2-one;

5-Chloro-1-[1-(5-methyl-2-p-tolyl-1H-imidazol-4-ylmethyl)-piperidin-4-yl]-1,3-dihydro-benzoimidazol-2-one;

1-[1-[[2-[4-(Trifluoromethyl)phenyl]-1H-imidazol-5-yl]methyl]-4-piperidyl]-5H-imidazo[4,5-c]pyridin-4-one; and 5-(4-Bromophenyl)-3-[1-[[2-[4-(trifluoromethyl)phenyl]-1H-imidazol-5-yl]methyl]-4-piperidyl]-1H-imidazol-2-one.

The invention also relates in particular to a compound of formula (I) selected from 3-{1-[5-Methyl-2-(4-trifluoromethanesulfonyl-phenyl)-1H-imidazol-4-ylmethyl]-piperidin-4-yl}-3,4-dihydro-1H-quinazolin-2-one;

1-Methyl-3-{1-[5-methyl-2-(4-trifluoromethanesulfonyl-phenyl)-1H-imidazol-4-ylmethyl]-piperidin-4-yl}-1,3-dihydro-benzoimidazol-2-one;

3-{1-[2-(3-Chloro-4-trifluoromethyl-phenyl)-5-methyl-1H-imidazol-4-ylmethyl]-piperidin-4-yl}-3,4-dihydro-1H-quinazolin-2-one;

3-{1-[1,5-Dimethyl-2-(4-trifluoromethyl-phenyl)-1H-imidazol-4-ylmethyl]-piperidin-4-yl}-3,4-dihydro-1H-quinazolin-2-one;

3-{1-[2-(4-Methanesulfonyl-phenyl)-5-methyl-1H-imidazol-4-ylmethyl]-piperidin-4-yl}-3,4-dihydro-1H-quinazolin-2-one;

3-{1-[5-Methyl-2-(4-trifluoromethanesulfonyl-phenyl)-1H-imidazol-4-ylmethyl]-piperidin-4-yl}-1H-pyrrolo[3,2-c]pyridine;

1-{1-[2-(4-Methanesulfonyl-phenyl)-5-methyl-1H-imidazol-4-ylmethyl]-piperidin-4-yl}-3-methyl-1,3-dihydro-benzoimidazol-2-one;

3-{1-[5-Propyl-2-(4-trifluoromethyl-phenyl)-1H-imidazol-4-ylmethyl]-piperidin-4-yl}-3,4-dihydro-1H-quinazolin-2-one;

6-(4-Methyl-piperazin-1-yl)-1-{1-[5-methyl-2-(4-trifluoromethyl-phenyl)-1H-imidazol-4-ylmethyl]-piperidin-4-yl}-1,3-dihydro-benzoimidazol-2-one; and 3-{1-[5-Methyl-2-(4-trifluoromethyl-phenyl)-1H-imidazol-4-ylmethyl]-piperidin-4-yl}-1H-pyrrolo[3,2-c]pyridine.

The further invention relates in particular to a compound of formula (I) wherein $A^1$ is $A^{11}$, $A^{12}$, $A^{13}$, $A^{14}$, $A^{15}$ or $A^{16}$;

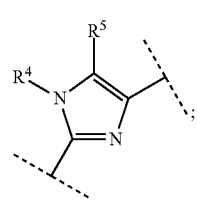

(A$^{11}$)

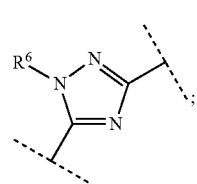

(A$^{12}$)

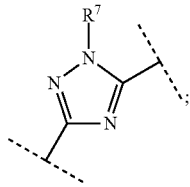

(A$^{13}$)

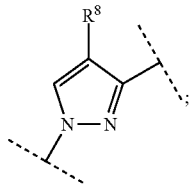

(A$^{14}$)

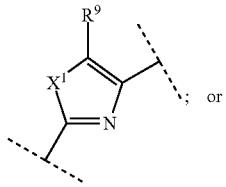

(A$^{15}$)

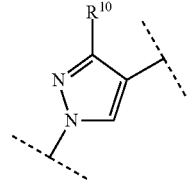

(A$^{16}$)

$X^1$ is oxygen or sulfur;

$R^4$ is hydrogen, alkyl or alkoxyalkyl;

$R^5$ is hydrogen, alkyl, phenyl, phenylalkyl or alkoxyalkyl;

$R^6$ is alkyl;

$R^7$ is alkyl;

$R^8$ is alkyl;

$R^9$ is alkyl; and $R^{10}$ is alkyl.

The invention relates in particular to a compound of formula (I) wherein $R^4$ is hydrogen, methyl or methoxyethyl.

The invention relates in particular to a compound of formula (I) wherein $R^5$ is hydrogen, methyl, propyl, phenyl, phenylmethyl or methoxyethyl.

The invention relates in particular to a compound of formula (I) wherein $R^6$ is methyl.

The invention relates in particular to a compound of formula (I) wherein $R^7$ is methyl.

The invention relates in particular to a compound of formula (I) wherein $R^8$ is methyl.

The invention relates in particular to a compound of formula (I) wherein $R^9$ is methyl.

The invention relates in particular to a compound of formula (I) wherein $R^{10}$ is methyl.

The invention relates in particular to a compound of formula (I) wherein $A^{12}$ is

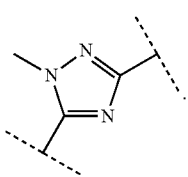

The invention relates in particular to a compound of formula (I) wherein $A^{13}$ is

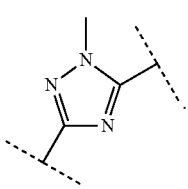

The invention relates in particular to a compound of formula (I) wherein $A^{14}$ is

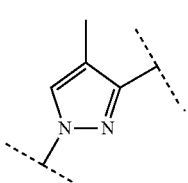

The invention relates in particular to a compound of formula (I) wherein $A^{15}$ is

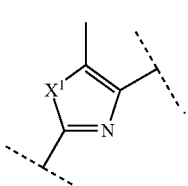

The invention relates in particular to a compound of formula (I) wherein $A^{16}$ is

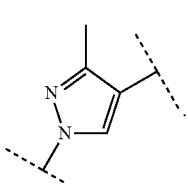

The invention relates in particular to a compound of formula (I) wherein
$A^2$ is $A^{21}$, $A^{22}$, $A^{23}$, $A^{24}$, $A^{25}$; $A^{26}$; $A^{27}$; $A^{28}$ or $A^{29}$;

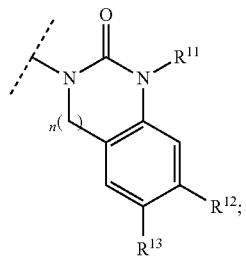
(A$^{21}$)

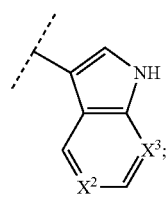
(A$^{22}$)

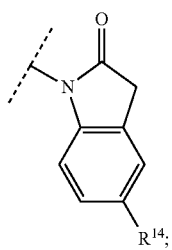
(A$^{23}$)

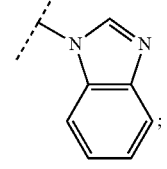
(A$^{24}$)

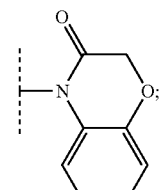
(A$^{25}$)

(A$^{26}$)

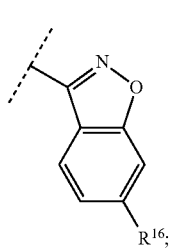
(A$^{27}$)

-continued

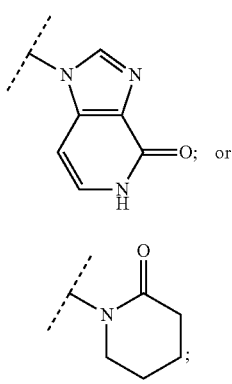
(A²⁸)

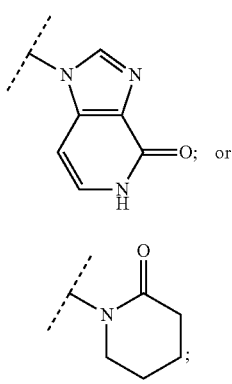
(A²⁹)

one of $X^2$ and $X^3$ is nitrogen and the other one is —CH—; or $X^2$ and $X^3$ are both —CH— at the same time;
$X^4$ is nitrogen or —CH—;
$R^{11}$ is hydrogen, methyl, alkoxycarbonylalkyl, alkoxyalkyl, hydroxyalkyl,
alkylsulfonylalkyl, alkylcarbonyloxyalkyl, aminocarbonyl alkyl,
alkylaminocarbonylalkyl or carboxyalkyl;
$R^{12}$ is hydrogen or halogen;
$R^{13}$ is hydrogen, morpholinyl, pyrrolidinyl or methylpiperazinyl;
$R^{14}$ is hydrogen or halogen;
$R^{15}$ is halophenyl;
$R^{16}$ is halogen; and
n is 0 or 1.

The invention relates in particular to a compound of formula (I) wherein $R^{11}$ is hydrogen, methyl, ethyl, methoxycarbonylmethyl, methoxmethyl, hydroxyethyl, methylsulfonylethyl, methylcarbonyloxyethyl, aminocarbonylmethyl, methylaminocarbonylmethyl or carboxymethyl.

The invention relates in particular to a compound of formula (I) wherein $R^{12}$ is hydrogen, chloro or fluoro.

The invention relates in particular to a compound of formula (I) wherein $R^{14}$ is hydrogen or chloro.

The invention relates in particular to a compound of formula (I) wherein $R^{15}$ is bromophenyl.

The invention relates in particular to a compound of formula (I) wherein $R^{16}$ is fluoro.

The following abbreviations are used in the present text:
DCM=Dichloromethane
DMA=N,N-Dimethylacetamide
DMF=N,N-Dimethylformamide
DMSO=Dimethylsulfoxide
EtOAc=Ethyl acetate
EtOH=Ethanol
MeOH=Methanol
RT=Room temperature
TFA=Trifluoroacetic acid
THF=Tetrahydrofuran The compound of formula (I) can be prepared by the methods given below, by the methods given in the examples or by analogous methods. Appropriate reaction conditions for the individual reaction steps are known to the person skilled in the art. Starting materials are either commercially available or can be prepared by methods analogous to the methods given below or in the examples or by methods known in the art. Unless otherwise specified, $R^1$-$R^1$, $A^1$, $A^2$ and n have the same meaning as defined above.

The compound of formula (I) may be prepared as illustrated in scheme 1.

Scheme 1

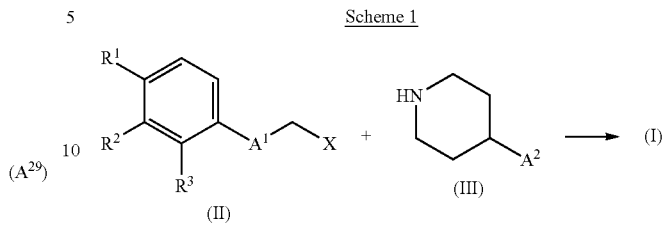

(II)      (III)

Formula (II) derivatives, wherein X is Cl, Br, I or —OSO₂R (R is methyl or p-toluyl), can be reacted with piperidine derivatives (III) in the presence of a base such as calcium hydroxide, potassium or cesium carbonate, diisopropylethyl amine or triethylamine in a solvent such as DMF, DMA, MeOH or EtOH at temperatures between RT and reflux temperature of the corresponding solvent, to obtain the compound of formula (I).

Alternatively, the compound of formula (I) can be obtained by reductive amination as illustrated in scheme 2.

Scheme 2

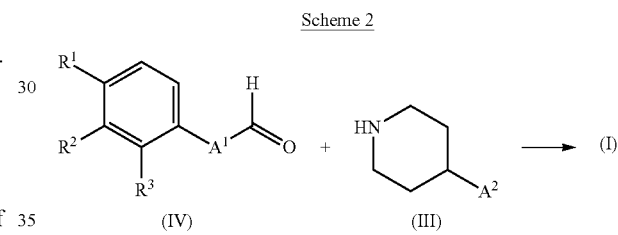

(IV)      (III)

Aldehyde derivatives (IV) can be reacted with piperidine derivatives (III) in the presence of a reducing agent such as sodium triacetoxyborohydride, sodium cyanoborohydride or sodium borohydride in solvents such as DCM, dichloroethane or MeOH to obtain the compound of formula (I).

Derivatives (II), wherein $A^1$ is $A^{11}$ may be prepared according to scheme 3.

Scheme 3

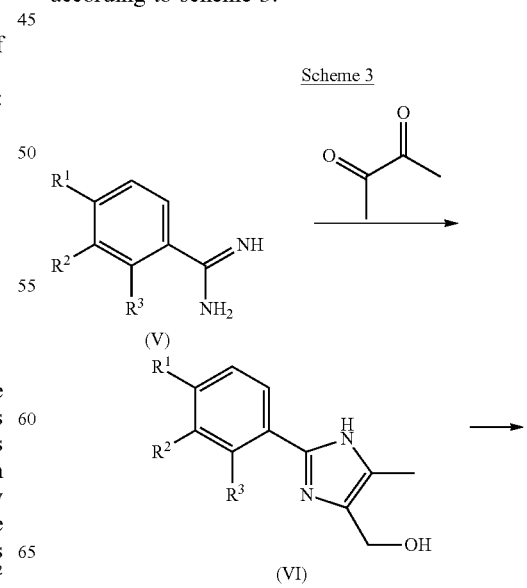

(V)

(VI)

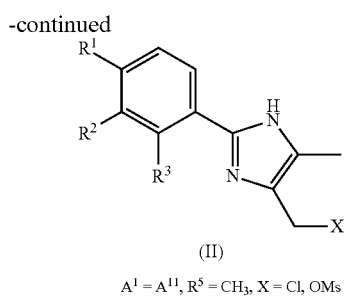

(II)

$A^1 = A^{11}, R^5 = CH_3, X = Cl, OMs$

Reaction of amidine derivatives (V) with first 2,3-butanedione in iso-propanol or sodium hydroxide solution as a solvent and secondly with HCl in water can afford imidazole derivatives (VI). Compounds (VI) can be converted into derivatives (II) by reaction with thionylchloride or by reaction with mesyl chloride in presence of triethylamine.

An alternative route to prepare derivatives (II), wherein $A^1$ is $A^{11}$ is illustrated in scheme 4.

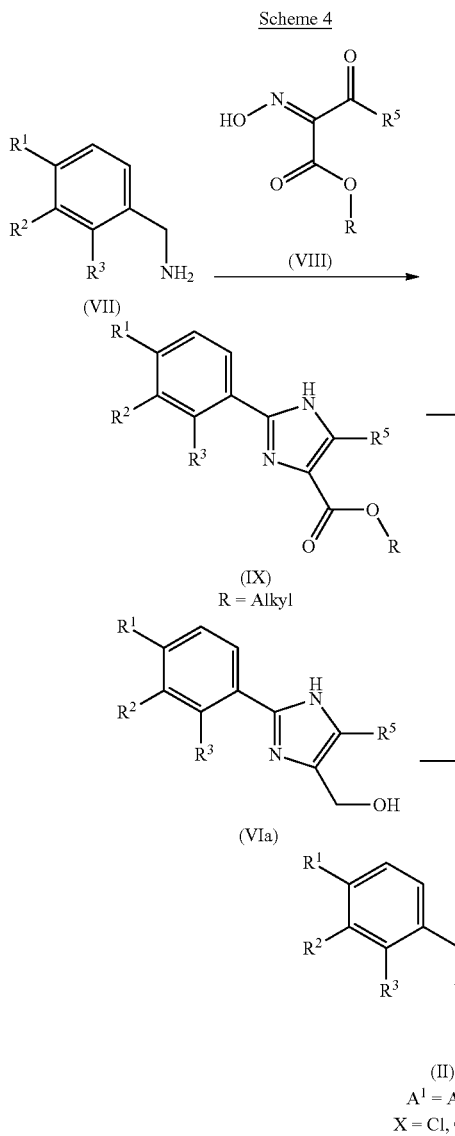

Formula (IX) compounds can be obtained by reaction of b-ketoester derivatives (VIII) with benzylamines (VII) in acetonitrile at reflux temperature. Transformation of formula (IX) compounds into derivatives (II) can be accomplished with a reducing agent such as lithium aluminum hydride to obtain formula (VIa) compounds that can be converted to (II) by reaction with thionylchloride or by reaction with mesyl chloride in presence of triethylamine.

Formula (IX) compounds can also be reacted with iodo or bromo derivatives $R^4$—I or $R^4$—Br in the presence of a base such as potassium tert-butoxide or sodium hydride before conversion to the corresponding derivatives (II) as indicated in scheme 5.

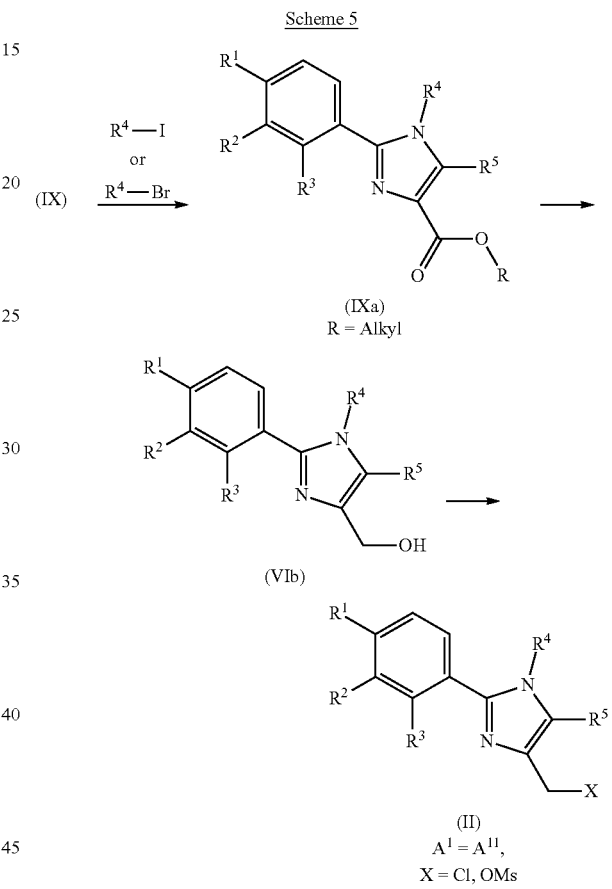

Derivatives (II), wherein $A^1$ is $A^{11}$ may also be prepared according to scheme 6. Reaction of amidine derivatives (V) with dihydroxyacetone in ammonia solution provides imidazole derivatives (VIc) that can be converted to formula (II) compounds as described above.

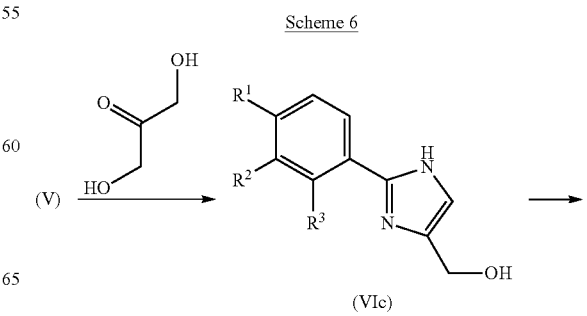

-continued

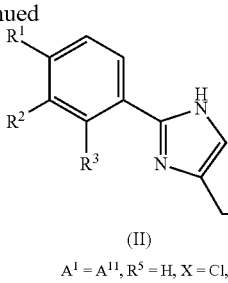

(II)

A$^1$ = A$^{11}$, R$^5$ = H, X = Cl, OMs

Derivatives (II), wherein A$^1$ is A$^{15}$ may be prepared according to scheme 7. Reaction of a thiobenzamide derivative (X) with 3-chloro-2-butanone provides thiazole derivatives (XI) which can be converted into formula (II) compounds by reaction with N-bromosuccinimide in the presence of 2,2'-azobis(2-methylpropionitrile) in acetonitrile.

Scheme 7

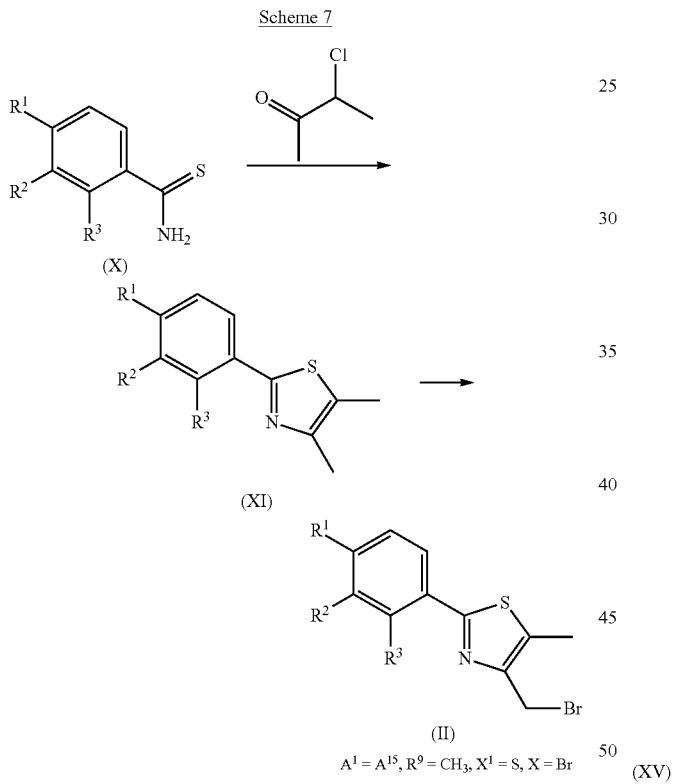

(II)

A$^1$ = A$^{15}$, R$^9$ = CH$_3$, X$^1$ = S, X = Br

Derivatives (II), wherein A$^1$ is A$^{12}$ or A$^{13}$ may be prepared according to scheme 8. By reaction of nitrile derivatives (XII) with protected 2-hydroxyacetohydrazide (XIII) in presence of potassium tert-butoxide in MeOH at reflux temperature, triazole derivatives (XIV) can be obtained. A suitable protecting group of the 2-hydroxyacetohydrazide might be a benzyl moiety. Reaction of derivatives (XIV) with alkyl iodides in the presence of a base such as potassium hydroxide provides formula (XV) and (XVI) compounds. Derivatives (XV) and (XVI) can be converted into formula (II) compounds by cleavage of the protecting group and subsequent reaction with thionylchloride or by reaction with mesyl chloride in presence of triethylamine. The deprotection step might be accomplished by hydrogenation if the protecting group is a benzyl moiety.

Scheme 8

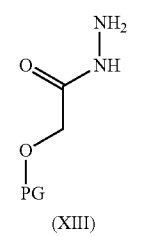

(XII)

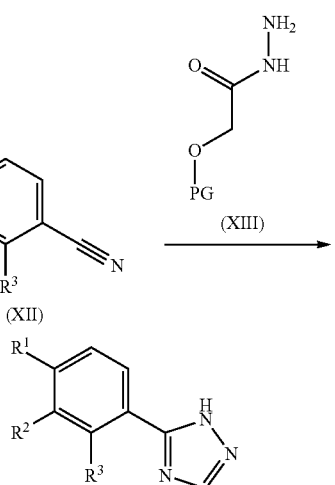

(XIV)

(XV)

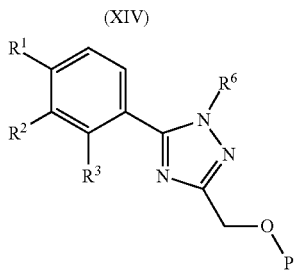

(XVI)

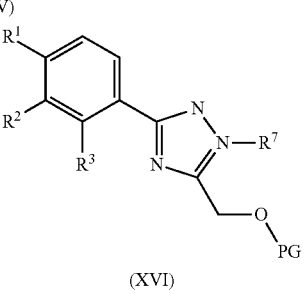

(XVII)

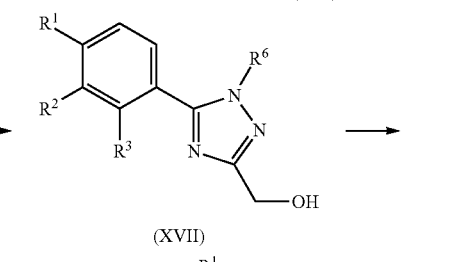

(II)

A$^1$ = A$^{13}$, X = Cl, OMs

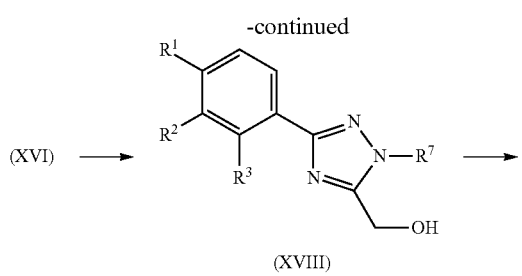

(XVIII)

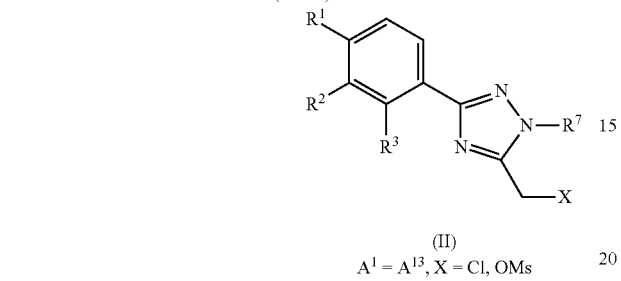

(II)
$A^1 = A^{13}, X = Cl, OMs$

PG = protecting group

Formula (IV) compounds, wherein $A^1$ is $A^{16}$ can be prepared according to scheme 9. Reaction of boronic acid derivatives (XIX) with pyrazoles (XX) in the presence of pyridine and anhydrous cupric(II)acetate provides compounds of formula (XXI). Derivatives (XXI) can be converted into formula (IV) compounds by formylation reaction that can for example be accomplished with phosphorus oxychloride and DMF.

compounds into pyrazole derivatives (XXIII) can be achieved by reaction with 4-[prop-1-enyl]morpholine in the presence of triethylamine and treatment of the initial reaction product with HCl in dioxane. Derivatives (XXIII) can be converted into formula (II) compounds in two steps. The first step can be accomplished with a reducing agent such as lithium aluminum hydride to obtain formula (XXIV) compounds that can be converted to (II) by reaction with thionylchloride or by reaction with mesyl chloride in presence of triethylamine.

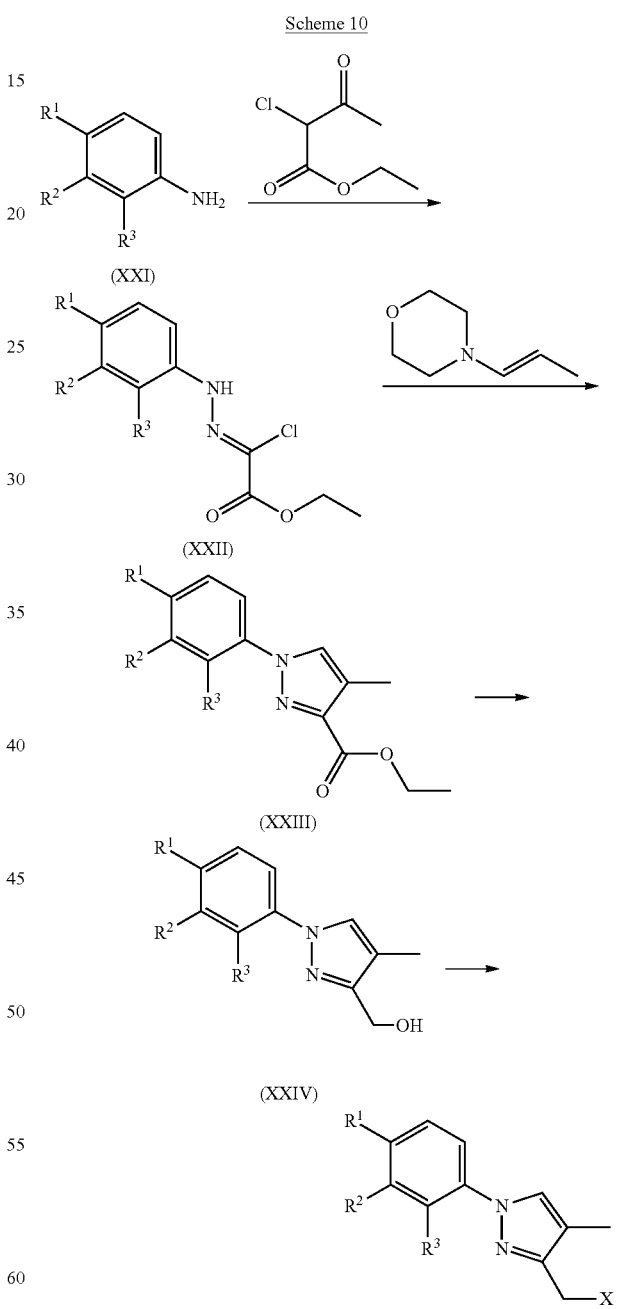

Derivatives (II), wherein $A^1$ is $A^{14}$ may be prepared according to scheme 10. Aniline derivatives (XXI) can be reacted with sodium nitrite in the presence of HCl and subsequently with ethyl-2-chloroacetoacetate to obtain formula (XXII) compounds. Transformation of formula (XXII)

Derivatives (III), wherein $A^2$ is $A^{21}$ may be prepared according to scheme 11. Formula (XXV) compounds can be deprotonated using a base such as sodium hydride in a solvent such as DMF and can subsequently be reacted with iodo or bromo derivatives or $R^{11}$—Br (See below) to obtain derivatives (XXVI). Suitable protecting groups (PG) for this type of transformations are for example benzyl or Boc groups which can be easily removed in the subsequent step either by hydrogenation in the presence of a catalyst such as palladium on carbon or by hydrolysis involving acids such as TFA or HCl.

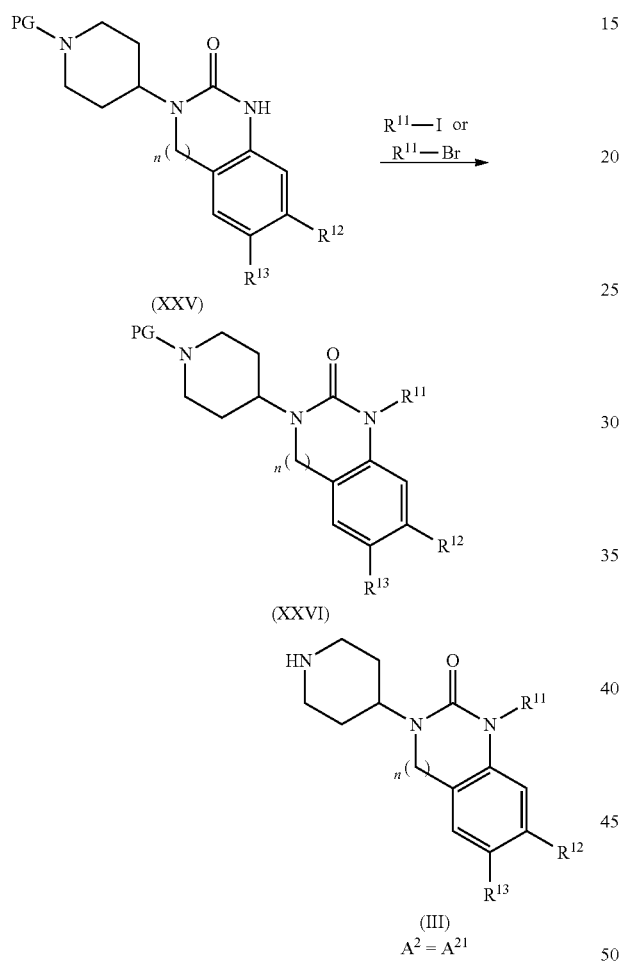

PG = protecting group

Derivatives (III), wherein $A^2$ is $A^{21}$ may also be prepared according to scheme 12. By reductive amination reaction of aldehyde derivatives (XXVIII) with protected (PG=protecting group) 4-aminopiperidines (XXVII) using reducing agents such as sodium borohydride, derivatives (XXIX) can be obtained. Conversion of nitro derivatives (XXIX) into aniline compounds (XXX) can be accomplished by reaction with ammonium chloride in the presence of zinc dust in MeOH as a solvent. Reaction of formula (XXX) compounds with carbonyldiimidazole provides derivatives (XXV) which can be converted into formula (III) compounds as described for scheme 11 by cleavage of the protecting group.

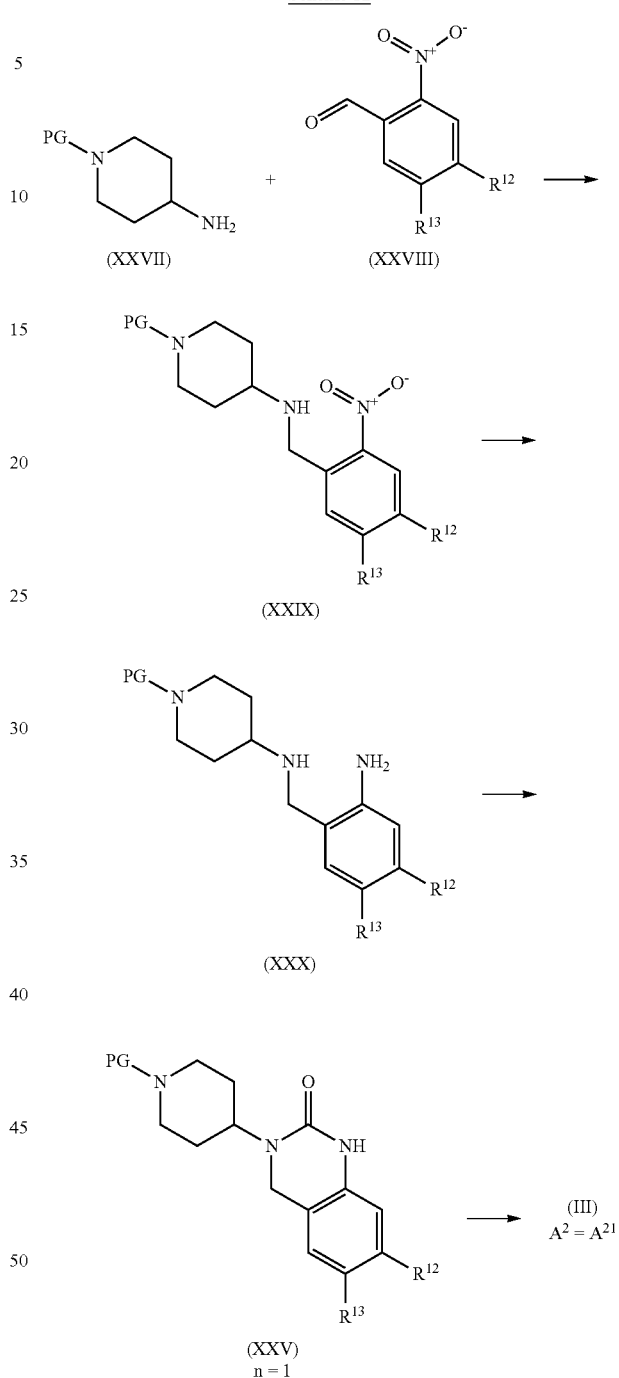

Aniline derivatives (XXX) can be prepared alternatively as illustrated in scheme 13. Amide coupling reaction between carboxylic acid derivatives (XXXI) and protected 4-aminopiperidines (XXVII), using coupling reagents such as N-(3-dimethylaminopropyl)-N'-ethylcarbodiimide and 1-hydroxybenzotriazole, provides amide derivatives (XXXII) which can subsequently be converted into formula (XXX) compounds by reaction with lithium aluminum hydride.

Scheme 13

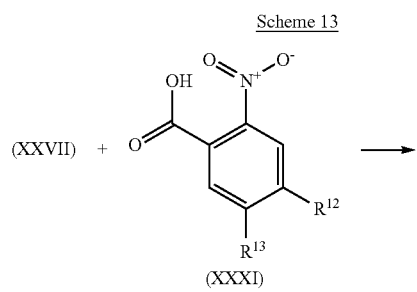
(XXVII) + (XXXI)

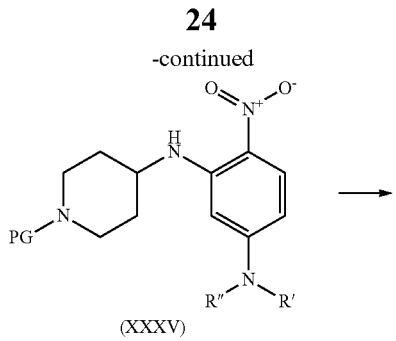
(XXXV)

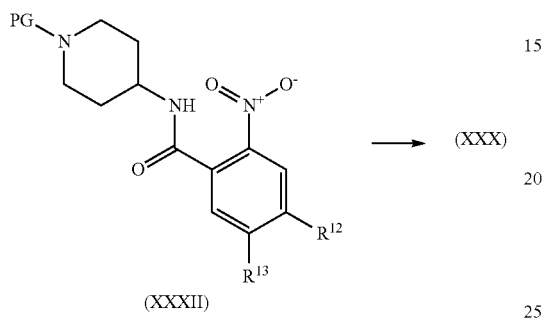
(XXXII) → (XXX)

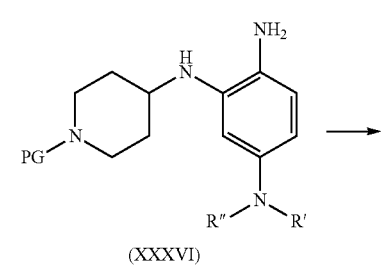
(XXXVI)

A possible preparation of formula (III) compounds, wherein $A^2$ is $A^{21}$, n=0 and $R^{11}$ is an amino substituent, is illustrated in scheme 14. Protected 4-aminopiperidines (XXVII) can be reacted with 2,4-dichloro-1-nitro-benzene in the presence of a base such as potassium carbonate to obtain formula (XXXIII) compounds. Reaction of derivatives (XXXIII) with amine derivatives (XXXIV) delivers formula (XXXV) compounds which can be subjected to catalytic hydrogenation conditions to obtain aniline derivatives (XXXVI). Conversion of derivatives (XXXVII) to the corresponding formula (III) compounds can be accomplished by reaction with carbonyldiimidazole and subsequent cleavage of the protecting group as described for scheme 12.

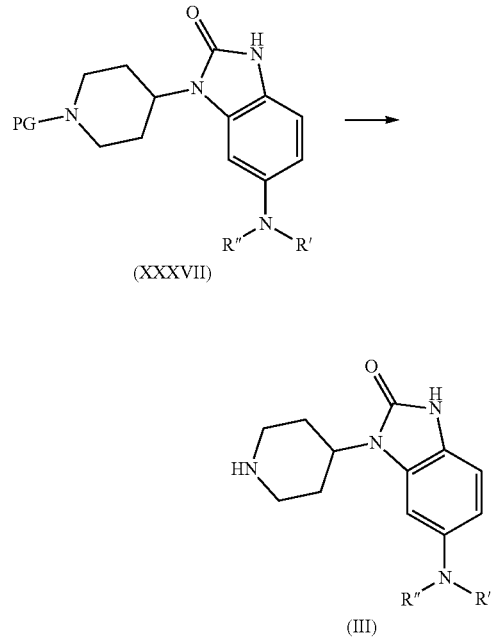
(XXXVII)

(III)

$A^1 = A^{21}$, n = 0, $R^{13}$ = NR'R''

Scheme 14

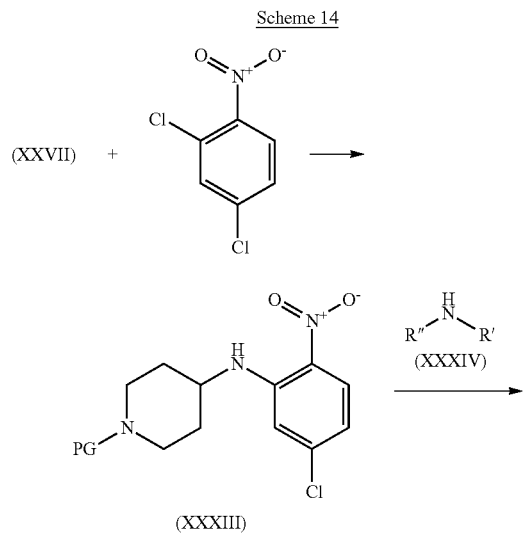

NR'R'' represents $R^{13}$ with $R^{13}$=morpholinyl, pyrrolidinyl or methylpiperazinyl.

Derivatives (III), wherein $A^2$ is $A^{22}$ may be prepared according to scheme 15. Reaction of a protected piperidone derivative (XXXVIII) with formula (XXXIX) compounds in the presence of potassium hydroxide in MeOH at elevated temperatures delivers derivatives (XL) which can be subjected to hydrogenation in the presence of platinum oxide as a catalyst to obtain formula (XLI) compounds. A possible protecting group (PG) for this reaction sequence might be a Boc group. Cleavage of the protecting group delivers formula (II) compounds.

Scheme 15

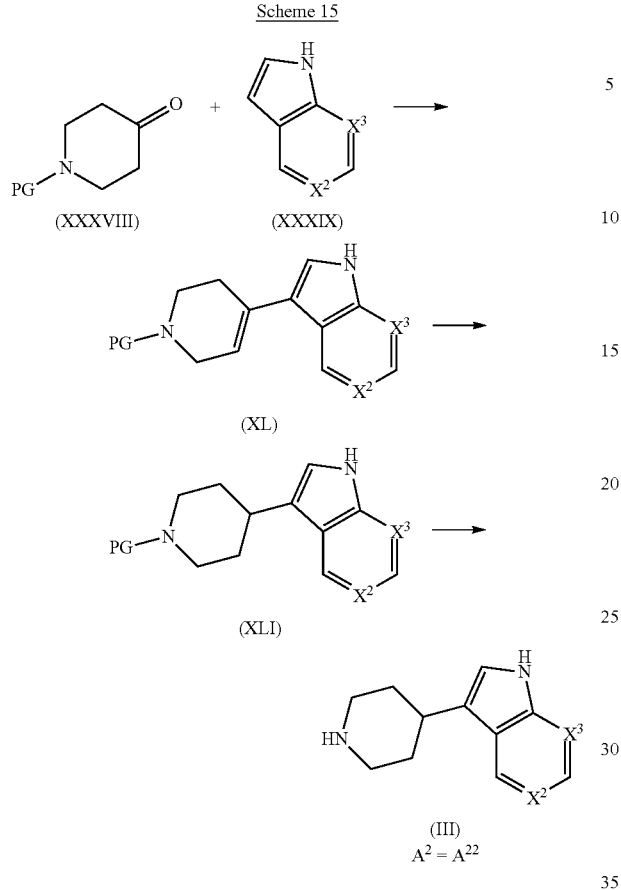

Derivatives (III), wherein $A^2$ is $A^{23}$ may be prepared according to scheme 16. Deprotonation of diethyl malonate and reaction of this anion with chloro-nitro benzene derivatives (XLII) delivers formula (XLIII) compounds which can be subjected to a decarbalkoxylation reaction using lithium chloride and water in DMSO as a solvent at elevated temperature to obtain formula (XLIV) compounds. Reduction of the nitro group using hydrogen in the presence of platinum oxide as a catalyst and subsequent reaction of the resulting formula (XLV) compounds with derivatives (XXXVIII) in the presence of a reducing agent such as sodium triacetoxyborohydride delivers formula (XLVI) compounds. A suitable protecting (PG) group for this reaction sequence might be a Boc group which can be cleaved with acids such as TFA or HCl to obtain formula (III) compounds.

Scheme 16

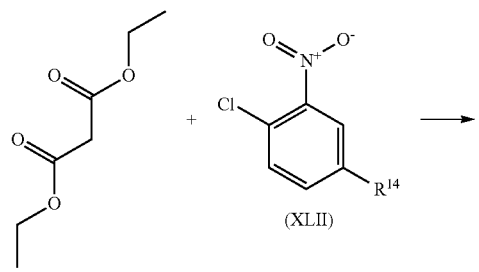

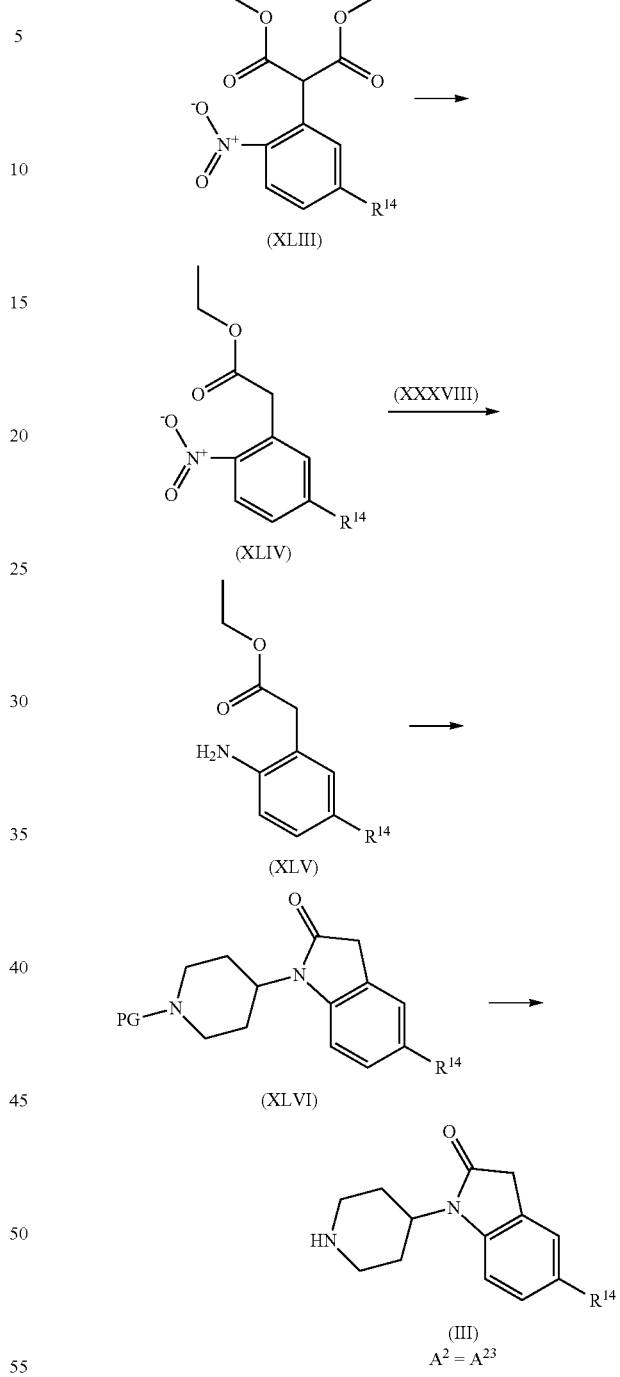

Derivatives (III), wherein $A^2$ is $A^{26}$ and $X^4$=CH may be prepared according to scheme 17. Reaction of bromomethyl ketone derivatives (XLVII) with protected 4-aminopiperidines (XXVII) and subsequent reaction with sodium cyanate delivers derivatives (XLVIII) which can be converted into formula (III) compounds by a final deprotection step. A suitable protecting (PG) group for this reaction sequence might be a Boc group which can be cleaved with acids such as TFA or HCl.

Scheme 17

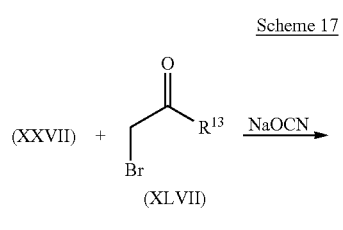

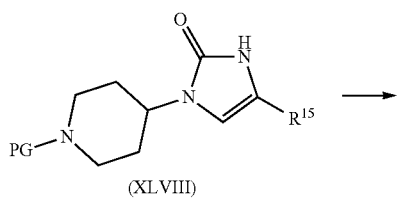

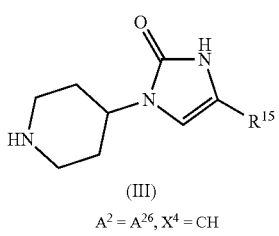

(III)
$A^2 = A^{26}, X^4 = CH$

A possible route to derivatives (III), wherein $A^2$ is $A^{26}$ and $X^4=N$ is illustrated in scheme 18. Reaction of protected piperidone derivative (XXXVIII) with hydrazine provides hydrazone derivatives which can be reacted with reducing agents such as sodium borohydride to obtain hydrazine derivatives (XLIX). By reaction of formula (XLIX) compounds with derivatives (L) in the presence of a base such as diisopropylethyl amine formula (LI) compounds can be obtained. A suitable protecting (PG) group for this reaction sequence might be a Boc group which can be cleaved with acids such as TFA or HCl in a final step to obtain derivatives (III)

Scheme 18

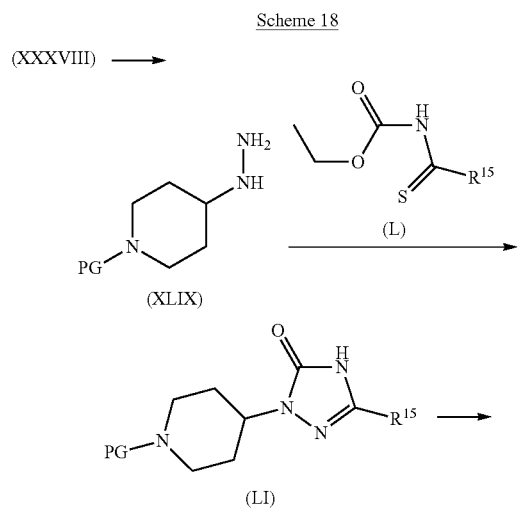

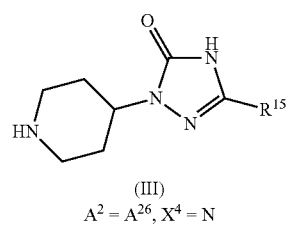

(III)
$A^2 = A^{26}, X^4 = N$

Derivative (III), wherein $A^2$ is $A^{28}$ might be obtained using a synthetic route according to scheme 19. Reaction of Boc-protected 4-aminopiperidine with 4-chloro-3-nitro-pyridine in the presence of triethylamine provides derivative (LII) which can be subjected to a hydrogenation reaction using palladium on carbon as a catalyst to obtain derivative (LIII). Derivative (LIII) can be treated with triethylorthoformate in the presence of catalytic amounts of 4-toluene sulfonic acid to obtain compound (LIV) which was converted to (LV) upon oxidation with 3-chloroperbenzoic acid. Treatment of (LV) with acetic anhydride and subsequent reaction with HCl delivers derivative (III) wherein $A^1$ is $A^{28}$.

Scheme 19

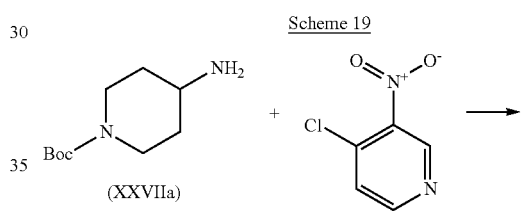

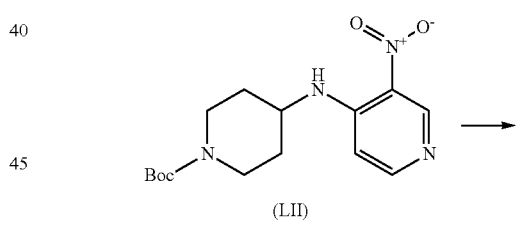

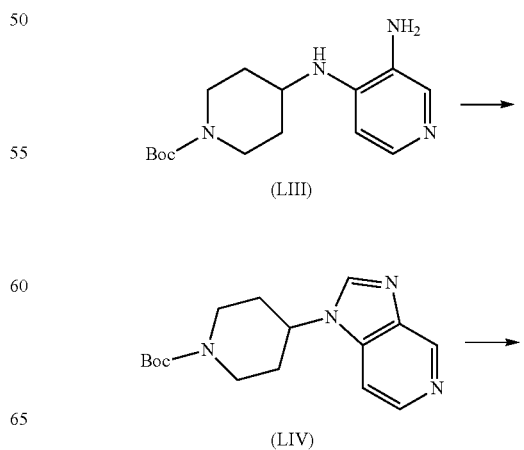

-continued

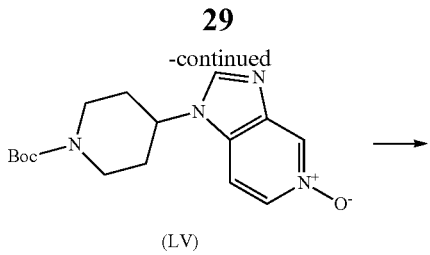

(LV)

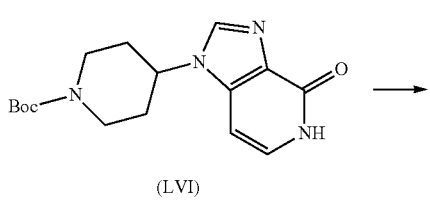

(LVI)

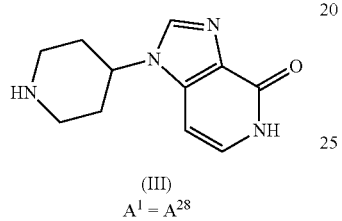

(III)
A¹ = A²⁸

The invention thus also relates to a process for the manufacture of a compound of formula (I) comprising one of the following steps:

(a) the reaction of a compound of formula (II)

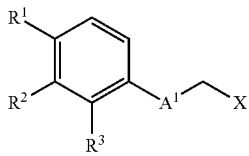

(II)

in the presence of a compound of formula (III)

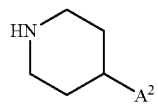

(III)

and a base; or (b) the reaction of a compound of formula (IV)

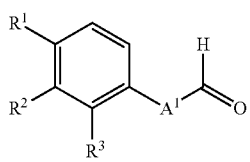

(IV)

in the presence of a compound of formula (III) as defined above and a reducing agent;

wherein X is Cl, Br, I or —OSO₂R, R is methyl or p-toluyl and A¹, A², R¹ to R³ are as defined above.

In step (a) the base is for example calcium hydroxide, potassium or cesium carbonate, diisopropylethyl amine or triethylamine.

Step (a) can be carried out in a solvent such as DMF, DMA, MeOH or EtOH, at temperatures between RT and reflux temperature of the corresponding solvent In step (b) the reducing agents for example sodium triacetoxyborohydride, sodium cyanoborohydride or sodium borohydride.

Step (b) can be done in a solvent such as DCM, dichloroethane or MeOH.

The invention will now be illustrated by the following examples which have no limiting character.

EXAMPLES

Example 1

1-Methyl-3-{1-[5-methyl-2-(4-trifluoromethyl-phenyl)-1H-imidazol-4-ylmethyl]-piperidin-4-yl}-1,3-dihydro-benzoimidazol-2-one

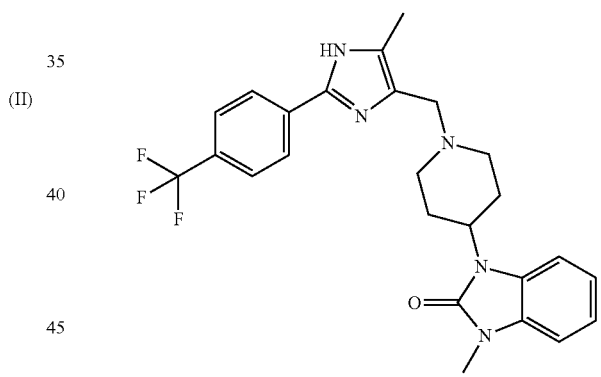

1-Methyl-3-(4-piperidyl)benzimidazol-2-one (CAS 53786-10-0) (100 mg; 0.432 mmol) was dissolved in DMF (1.5 ml) and Ca(OH)₂ (67 mg; 96%; 0.865 mmol) was added. The suspension was stirred at RT for 15 min, then a solution of 4-(chloromethyl)-5-methyl-2-[4-(trifluoromethyl)phenyl]-1H-imidazole; hydrochloride (intermediate 1) (135 mg; 0.432 mmol) in DMF (1.5 ml) was added dropwise. After the addition, the reaction mixture was stirred at RT overnight. The reaction mixture was diluted with water and extracted with EtOAc. The combined organic layers were washed with diluted NaOH and brine, dried with Na₂SO₄ and evaporated. The remaining residue was purified by column chromatography (20 g silica gel; DCM/MeOH 100:0-90:10) to obtain the title compound as light brown solid (141 mg). MS (ESI): 470.3 (M+H)⁺.

The following examples were prepared in analogy to example 1:

| Ex. | Name | Structure | MS (ESI) | Reagents |
|---|---|---|---|---|
| 2 | 1-{1-[5-Methyl-2-(4-trifluoromethyl-phenyl)-1H-imidazol-4-ylmethyl]-piperidin-4-yl}-1,3-dihydro-indol-2-one | 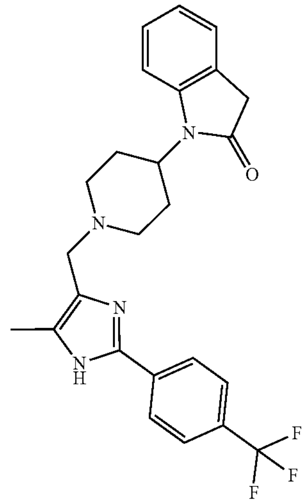 [SMILES: Cc1[nH]c(-c2ccc(C(F)(F)F)cc2)nc1CN1CCC(N2C(=O)Cc3ccccc32)CC1] | 455.2 (M + H)+ | 4-(Chloromethyl)-5-methyl-2-[4-(trifluoromethyl)phenyl]-1H-imidazole; hydrochloride (Intermediate 1)/1-(4-Piperidyl)indolin-2-one (CAS 16223-25-9) |
| 3 | 1-{1-[5-Methyl-2-(4-trifluoromethyl-phenyl)-1H-imidazol-4-ylmethyl]-piperidin-4-yl}-1H-benzoimidazole | 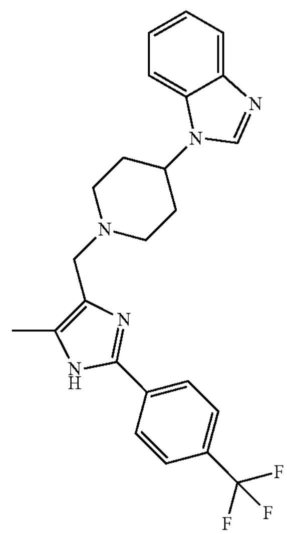 [SMILES: Cc1[nH]c(-c2ccc(C(F)(F)F)cc2)nc1CN1CCC(n2cnc3ccccc32)CC1] | 440.3 (M + H)+ | 4-(Chloromethyl)-5-methyl-2-[4-(trifluoromethyl)phenyl]-1H-imidazole; hydrochloride (Intermediate 1)/1-(4-piperidyl)benzimidazole (CAS 1187174-05-5) |
| 4 | 1-Methyl-3-{1-[5-methyl-2-(4-trifluoromethyl-phenyl)-oxazol-4-ylmethyl]-piperidin-4-yl}-1,3-dihydro-benzoimidazol-2-one | 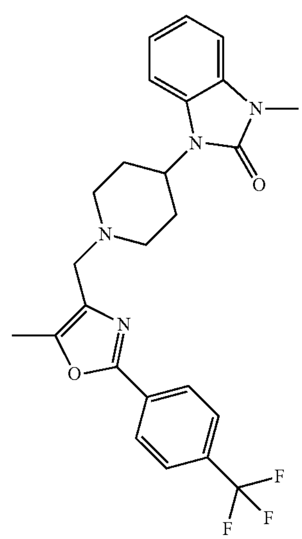 | 471.3 (M + H)+ | 4-(Chloromethyl)-5-methyl-2-[4-(trifluoromethyl)phenyl]oxazole (CAS 174258-39-0)/1-Methyl-3-(4-piperidyl)benzimidazol-2-one (CAS 53786-10-0) |

-continued

| Ex. | Name | Structure | MS (ESI) | Reagents |
|---|---|---|---|---|
| 5 | 1-Methyl-3-{1-[5-methyl-2-(4-trifluoromethyl-phenyl)-thiazol-4-ylmethyl]-piperidin-4-yl}-1,3-dihydro-benzoimidazol-2-one | 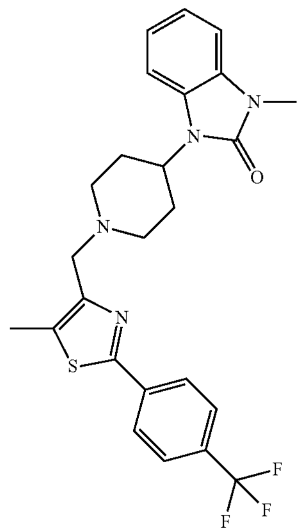 | 487.4 (M + H)+ | 4-(Bromomethyl)-5-methyl-2-[4-(trifluoromethyl)phenyl]thiazole (Intermediate 28)/Methyl-3-(4-piperidyl)benzimidazol-2-one (CAS 53786-10-0) |
| 6 | 1-{1-[5-Methyl-2-(4-trifluoromethyl-phenyl)-1H-imidazol-4-ylmethyl]-piperidin-4-yl}-1,3-dihydro-benzoimidazol-2-one | 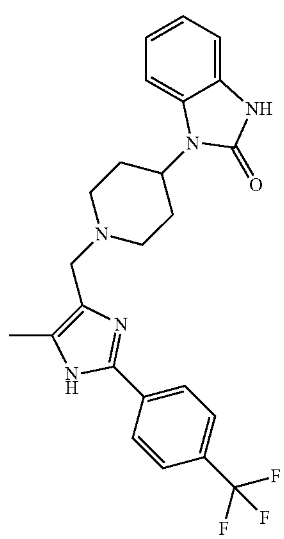 [SMILES: Cc1[nH]c(-c2ccc(C(F)(F)F)cc2)nc1CN1CCC(n2c(=O)[nH]c3ccccc32)CC1] | 456.3 (M + H)+ | 4-(Chloromethyl)-5-methyl-2-[4-(trifluoromethyl)phenyl]-1H-imidazole; hydrochloride (Intermediate 1)/3-(4-Piperidyl)-1H-benzimidazol-2-one (CAS 20662-53-7) |

-continued

| Ex. | Name | Structure | MS (ESI) | Reagents |
|---|---|---|---|---|
| 7 | 5-Chloro-1-{1-[5-methyl-2-(4-trifluoromethyl-phenyl)-1H-imidazol-4-ylmethyl]-piperidin-4-yl}-1,3-dihydro-benzoimidazol-2-one | 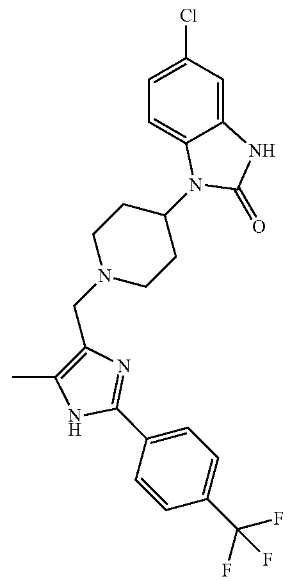 [SMILES: Cc1[nH]c(-c2ccc(C(F)(F)F)cc2)nc1CN1CCC(n2c(=O)[nH]c3cc(Cl)ccc32)CC1] | 490.2 (M + H)+ | 4-(Chloromethyl)-5-methyl-2-[4-(trifluoromethyl)phenyl]-1H-imidazole; hydrochloride (Intermediate 1)/6-Chloro-3-(4-piperidyl)-1H-benzimidazol-2-one (CAS 53786-28-0) |
| 8 | 1-[1-[[4-Methyl-2-[4-(trifluoromethyl)phenyl]-1H-imidazol-5-yl]methyl]-4-piperidyl]piperidin-2-one | 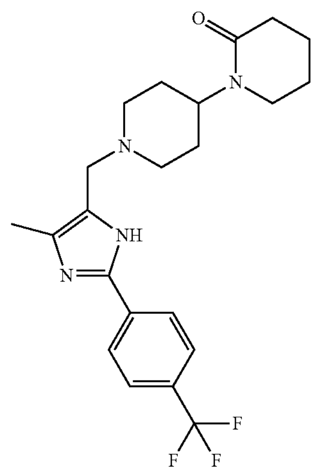 [SMILES: Cc1nc(-c2ccc(C(F)(F)F)cc2)[nH]c1CN1CCC(N2CCCCC2=O)CC1] | 421.2 (M + H)+ | 4-(Chloromethyl)-5-methyl-2-[4-(trifluoromethyl)phenyl]-1H-imidazole; hydrochloride (Intermediate 1)/1-(4-Piperidyl)piperidin-2-one (CAS 841200-67-7) |
| 9 | 1-{1-[5-Methyl-2-(4-trifluoromethyl-phenyl)-1H-imidazol-4-ylmethyl]-piperidin-4-yl}-6-pyrrolidin-1-yl-1,3-dihydro-benzoimidazol-2-one | 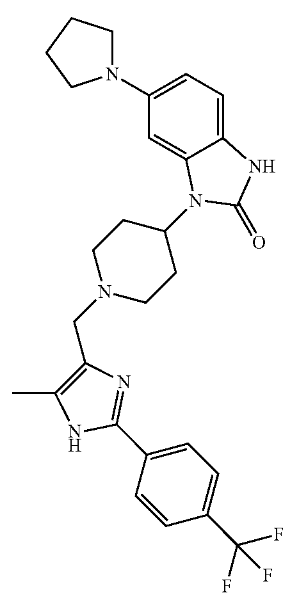 [SMILES: Cc1[nH]c(-c2ccc(C(F)(F)F)cc2)nc1CN1CCC(n2c(=O)[nH]c3ccc(N4CCCC4)cc32)CC1] | 525.4 (M + H)+ | 4-(Chloromethyl)-5-methyl-2-[4-(trifluoromethyl)phenyl]-1H-imidazole; hydrochloride (Intermediate 1)/3-(4-Piperidyl)-5-pyrrolidin-1-yl-1H-benzimidazol-2-one; hydrochloride (Intermediate 46) |

-continued

| Ex. | Name | Structure | MS (ESI) | Reagents |
|---|---|---|---|---|
| 10 | 1-{1-[5-Methyl-2-(4-trifluoromethyl-phenyl)-1H-imidazol-4-ylmethyl]-piperidin-4-yl}-6-morpholin-4-yl-1,3-dihydro-benzoimidazol-2-one | 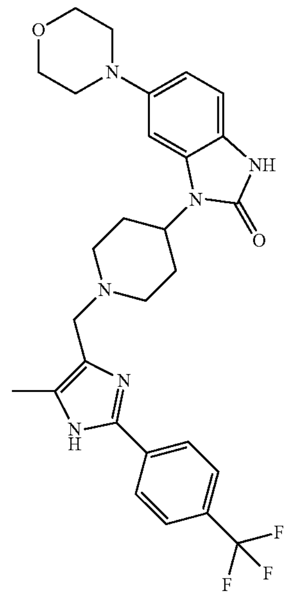 [SMILES: Cc1[nH]c(-c2ccc(C(F)(F)F)cc2)nc1CN1CCC(n2c(=O)[nH]c3ccc(N4CCOCC4)cc32)CC1] | 541.4 (M + H)+ | 4-(Chloromethyl)-5-methyl-2-[4-(trifluoromethyl)phenyl]-1H-imidazole; hydrochloride (Intermediate 1)/5-Morpholino-3-(4-piperidyl)-1H-benzimidazol-2-one; hydrochloride (Intermediate 47) |
| 11 | 6-(4-Methyl-piperazin-1-yl)-1-{1-[5-methyl-2-(4-trifluoromethyl-phenyl)-1H-imidazol-4-ylmethyl]-piperidin-4-yl}-1,3-dihydro-benzoimidazol-2-one | 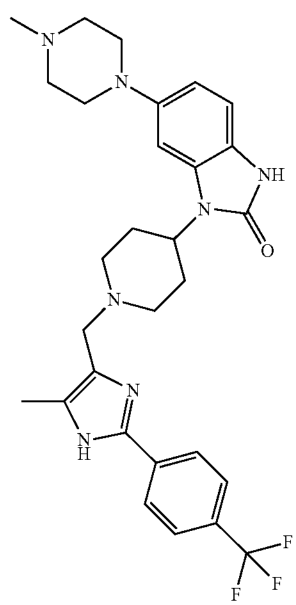 [SMILES: Cc1[nH]c(-c2ccc(C(F)(F)F)cc2)nc1CN1CCC(n2c(=O)[nH]c3ccc(N4CCN(C)CC4)cc32)CC1] | 554.4 (M + H)+ | 4-(Chloromethyl)-5-methyl-2-[4-(trifluoromethyl)phenyl]-1H-imidazole; hydrochloride (Intermediate 1)/5-(4-Methylpiperazin-1-yl)-3-(4-piperidyl)-1H-benzimidazol-2-one; dihydrochloride (Intermediate 48) |

-continued

| Ex. | Name | Structure | MS (ESI) | Reagents |
|---|---|---|---|---|
| 18 | 5-Chloro-3-methyl-1-{1-[5-methyl-2-(4-trifluoromethyl-phenyl)-1H-imidazol-4-ylmethyl]-piperidin-4-yl}-1,3-dihydro-benzoimidazol-2-one | 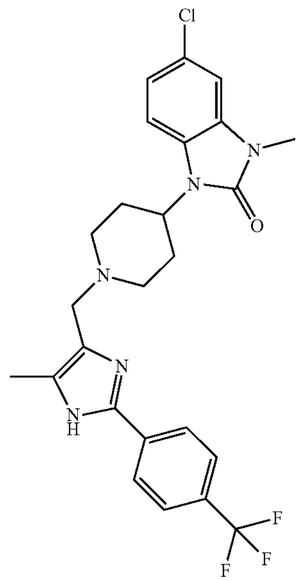 | 504.2 (M + H)+ | 4-(Chloromethyl)-5-methyl-2-[4-(trifluoromethyl)phenyl]-1H-imidazole; hydrochloride (Intermediate 1)/5-Chloro-3-methyl-1-(4-piperidyl)benzimidazol-2-one (Intermediate 29) |
| 19 | 4-{1-[5-Methyl-2-(4-trifluoromethyl-phenyl)-1H-imidazol-4-ylmethyl]-piperidin-4-yl}-4H-benzo[1,4]oxazin-3-one | 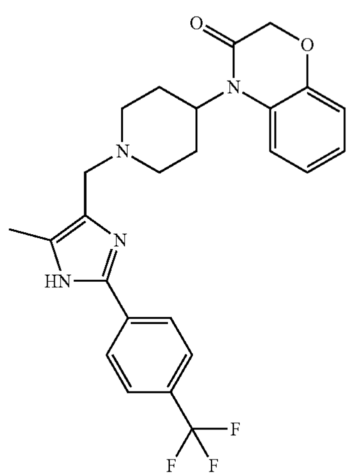 [SMILES: Cc1[nH]c(-c2ccc(C(F)(F)F)cc2)nc1CN1CCC(N2C(=O)COc3ccccc32)CC1] | 471.4 (M + H)+ | 4-(Chloromethyl)-5-methyl-2-[4-(trifluoromethyl)phenyl]-1H-imidazole; hydrochloride (Intermediate 1)/4-(4-Piperidyl)-1,4-benzoxazin-3-one (CAS 356072-48-5) |
| 20 | 5-Chloro-1-{1-[2-(4-chloro-phenyl)-5-methyl-1H-imidazol-4-ylmethyl]-piperidin-4-yl}-1,3-dihydro-benzoimidazol-2-one | 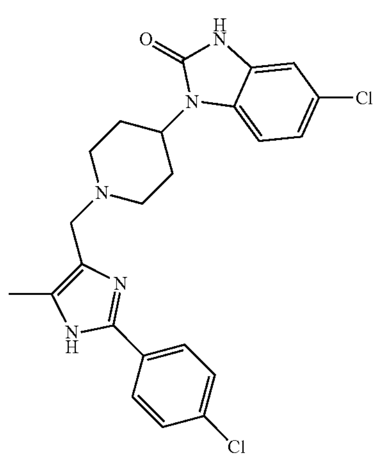 [SMILES: Cc1[nH]c(-c2ccc(Cl)cc2)nc1CN1CCC(n2c(=O)[nH]c3cc(Cl)ccc32)CC1] | 456.4 (M + H)+ | 4-(Chloromethyl)-2-(4-chlorophenyl)-5-methyl-1H-imidazole; hydrochloride (Intermediate 2)/6-Chloro-3-(4-piperidyl)-1H-benzimidazol-2-one (CAS 53786-28-0) |

-continued

| Ex. | Name | Structure | MS (ESI) | Reagents |
|---|---|---|---|---|
| 21 | 5-Chloro-1-[1-(5-methyl-2-p-tolyl-1H-imidazol-4-ylmethyl)-piperidin-4-yl]-1,3-dihydro-benzoimidazol-2-one | 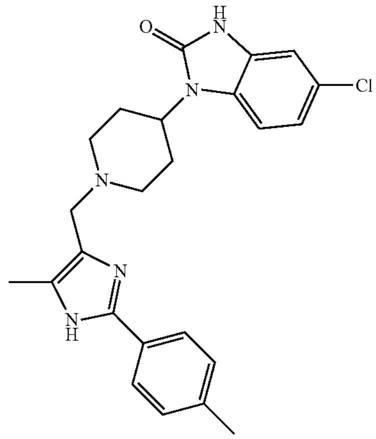 [SMILES: Cc1ccc(-c2nc(CN3CCC(n4c(=O)[nH]c5cc(Cl)ccc54)CC3)c(C)[nH]2)cc1] | 436.3 (M + H)$^+$ | 4-(Chloromethyl)-5-methyl-2-(p-tolyl)-1H-imidazole; hydrochloride (Intermediate 3)/6-Chloro-3-(4-piperidyl)-1H-benzimidazol-2-one (CAS 53786-28-0) |
| 22 | 5-Chloro-1-{1-[2-(3-fluoro-4-methyl-phenyl)-5-methyl-1H-imidazol-4-ylmethyl]-piperidin-4-yl}-1,3-dihydro-benzoimidazol-2-one | 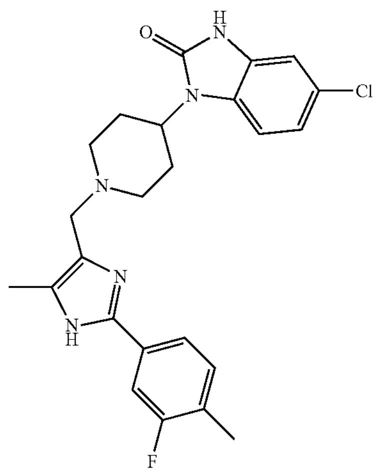 | 454.3 (M + H)$^+$ | 4-(Chloromethyl)-2-(3-fluoro-4-methyl-phenyl)-5-methyl-1H-imidazole; hydrochloride (Intermediate 4)/6-Chloro-3-(4-piperidyl)-1H-benzimidazol-2-one (CAS 53786-28-0) |
| 23 | 5-Chloro-1-{1-[2-(3-chloro-4-methyl-phenyl)-5-methyl-1H-imidazol-4-ylmethyl]-piperidin-4-yl}-1,3-dihydro-benzoimidazol-2-one | 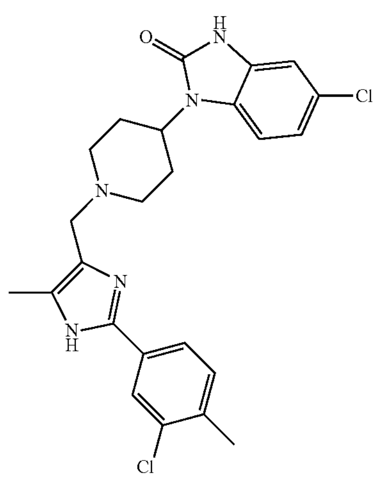 [SMILES: Cc1ccc(-c2nc(CN3CCC(n4c(=O)[nH]c5cc(Cl)ccc54)CC3)c(C)[nH]2)cc1Cl] | 470.1 (M + H)$^+$ | 4-(Chloromethyl)-2-(3-chloro-4-methyl-phenyl)-5-methyl-1H-imidazole; hydrochloride (Intermediate 5)/6-Chloro-3-(4-piperidyl)-1H-benzimidazol-2-one (CAS 53786-28-0) |

-continued

| Ex. | Name | Structure | MS (ESI) | Reagents |
|---|---|---|---|---|
| 24 | 1-Methyl-3-{1-[5-phenyl-2-(4-trifluoromethyl-phenyl)-1H-imidazol-4-ylmethyl]-piperidin-4-yl}-1,3-dihydro-benzoimidazol-2-one | 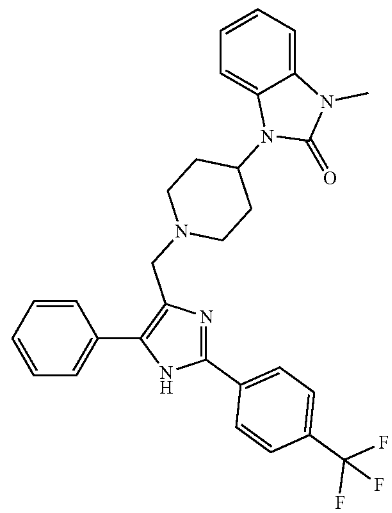 [SMILES: Cn1c(=O)n(C2CCN(Cc3nc(-c4ccc(C(F)(F)F)cc4)[nH]c3-c3ccccc3)CC2)c2ccccc21] | 531.0 (M + H)$^+$ | 4-(Chloromethyl)-5-phenyl-2-[4-(trifluoromethyl)phenyl]-1H-imidazole; hydrochloride (Intermediate 16)/1-Methyl-3-(4-piperidyl)benzimidazol-2-one (CAS 53786-10-0) |
| 25 | 7-Fluoro-3-{1-[5-methyl-2-(4-trifluoromethyl-phenyl)-1H-imidazol-4-ylmethyl]-piperidin-4-yl}-3,4-dihydro-1H-quinazolin-2-one | 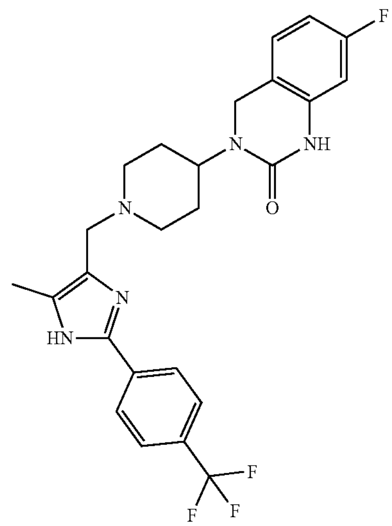 [SMILES: Cc1[nH]c(-c2ccc(C(F)(F)F)cc2)nc1CN1CCC(N2Cc3ccc(F)cc3NC2=O)CC1] | 488.3 (M + H)$^+$ | 4-(Chloromethyl)-5-methyl-2-[4-(trifluoromethyl)phenyl]-1H-imidazole; hydrochloride (Intermediate 1)/7-Fluoro-3-(4-piperidyl)-1,4-dihydroquinazolin-2-one (Intermediate 39) |
| 26 | 5-Chloro-3-ethyl-1-{1-[5-methyl-2-(4-trifluoromethyl-phenyl)-1H-imidazol-4-ylmethyl]-piperidin-4-yl}-1,3-dihydro-benzoimidazol-2-one | 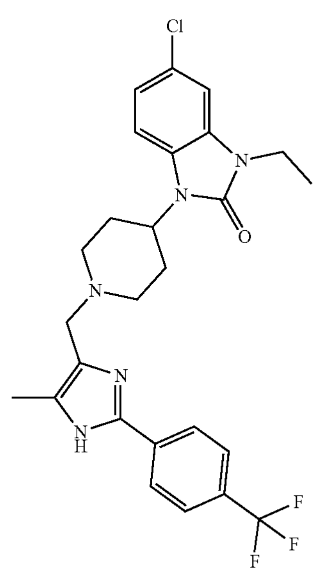 [SMILES: CCn1c(=O)n(C2CCN(Cc3nc(-c4ccc(C(F)(F)F)cc4)[nH]c3C)CC2)c2ccc(Cl)cc21] | 517.8 (M + H)$^+$ | 4-(Chloromethyl)-5-methyl-2-[4-(trifluoromethyl)phenyl]-1H-imidazole; hydrochloride (Intermediate 1)/5-Chloro-3-ethyl-1-(4-piperidyl)benzimidazol-2-one (Intermediate 30) |

-continued

| Ex. | Name | Structure | MS (ESI) | Reagents |
|---|---|---|---|---|
| 27 | 5-Chloro-3-(2-methoxy-ethyl)-1-{1-[5-methyl-2-(4-trifluoromethyl-phenyl)-1H-imidazol-4-ylmethyl]-piperidin-4-yl}-1,3-dihydro-benzoimidazol-2-one | 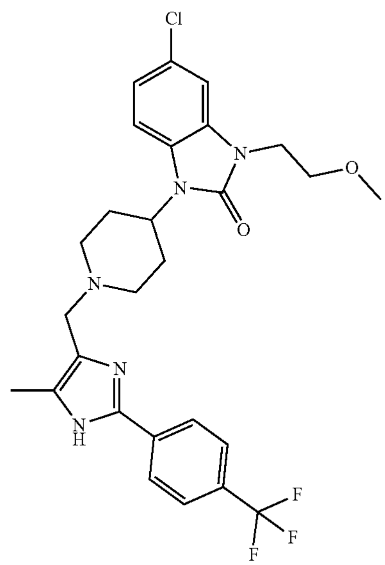 | 548.5 (M + H)+ | 4-(Chloromethyl)-5-methyl-2-[4-(trifluoromethyl)phenyl]-1H-imidazole; hydrochloride (Intermediate 1)/5-Chloro-3-(2-methoxyethyl)-1-(4-piperidyl)benzimidazol-2-one (Intermediate 31) |
| 28 | 3-{1-[5-Methyl-2-(4-trifluoromethyl-phenyl)-1H-imidazol-4-ylmethyl]-piperidin-4-yl}-3,4-dihydro-1H-quinazolin-2-one | 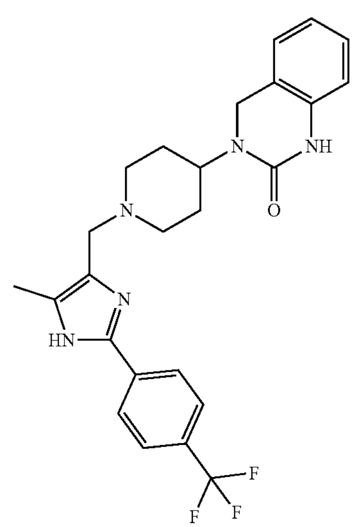 [SMILES: Cc1[nH]c(-c2ccc(C(F)(F)F)cc2)nc1CN1CCC(N2Cc3ccccc3NC2=O)CC1] | 470.4 (M + H)+ | 4-(Chloromethyl)-5-methyl-2-[4-(trifluoromethyl)phenyl]-1H-imidazole; hydrochloride (Intermediate 1)/3-(4-Piperidyl)-1,4-dihydroquinazolin-2-one (CAS 79098-75-2) |

-continued

| Ex. | Name | Structure | MS (ESI) | Reagents |
|---|---|---|---|---|
| 29 | Acetic acid 2-(6-chloro-3-{1-[5-methyl-2-(4-trifluoromethyl-phenyl)-1H-imidazol-4-ylmethyl]-piperidin-4-yl}-2-oxo-2,3-dihydro-benzoimidazol-1-yl)-ethyl ester | 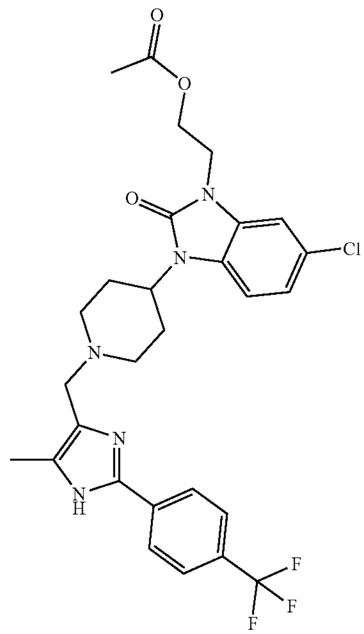 [SMILES: CC(=O)OCCn1c(=O)n(C2CCN(Cc3nc(-c4ccc(C(F)(F)F)cc4)[nH]c3C)CC2)c2ccc(Cl)cc21] | 575.8 (M + H)+ | 4-(Chloromethyl)-5-methyl-2-[4-(trifluoromethyl)phenyl]-1H-imidazole; hydrochloride (Intermediate 1)/2-[6-Chloro-2-oxo-3-(4-piperidyl)benzimidazol-1-yl]ethylacetate (Intermediate 32) |
| 31 | 2-(6-Chloro-3-{1-[5-methyl-2-(4-trifluoromethyl-phenyl)-1H-imidazol-4-ylmethyl]-piperidin-4-yl}-2-oxo-2,3-dihydro-benzoimidazol-1-yl)-acetamide | 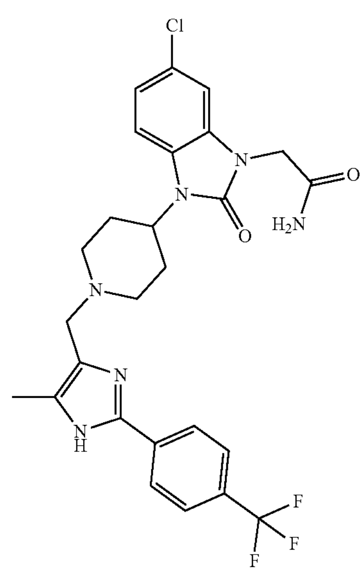 [SMILES: Cc1[nH]c(-c2ccc(C(F)(F)F)cc2)nc1CN1CCC(n2c(=O)n(CC(N)=O)c3cc(Cl)ccc32)CC1] | 547.3 (M + H)+ | 4-(Chloromethyl)-5-methyl-2-[4-(trifluoromethyl)phenyl]-1H-imidazole; hydrochloride (Intermediate 1)/2-[6-Chloro-2-oxo-3-(4-piperidyl)benzimidazol-1-yl]acetamide (Intermediate 33) |

| Ex. | Name | Structure | MS (ESI) | Reagents |
|---|---|---|---|---|
| 32 | 2-(6-Chloro-3-{1-[5-methyl-2-(4-trifluoromethyl-phenyl)-1H-imidazol-4-ylmethyl]-piperidin-4-yl}-2-oxo-2,3-dihydro-benzoimidazol-1-yl)-N-methyl-acetamide | 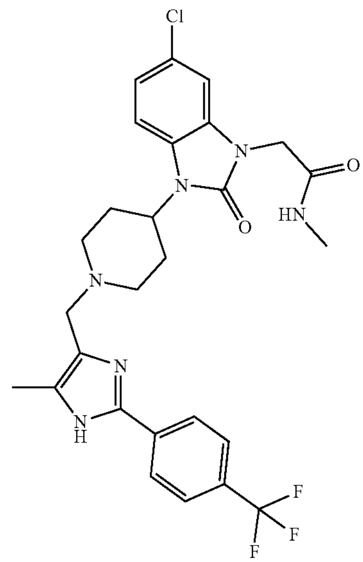 [SMILES: CNC(=O)Cn1c(=O)n(C2CCN(Cc3nc(-c4ccc(C(F)(F)F)cc4)[nH]c3C)CC2)c2ccc(Cl)cc21] | 561.1 (M + H)+ | 4-(Chloromethyl)-5-methyl-2-[4-(trifluoromethyl)phenyl]-1H-imidazole; hydrochloride (Intermediate 1)/2-[6-Chloro-2-oxo-3-(4-piperidyl)benzimidazol-1-yl]-N-methyl-acetamide (Intermediate 34) |
| 33 | (6-Chloro-3-{1-[5-methyl-2-(4-trifluoromethyl-phenyl)-1H-imidazol-4-ylmethyl]-piperidin-4-yl}-2-oxo-2,3-dihydro-benzoimidazol-1-yl)-acetic acid methyl ester | 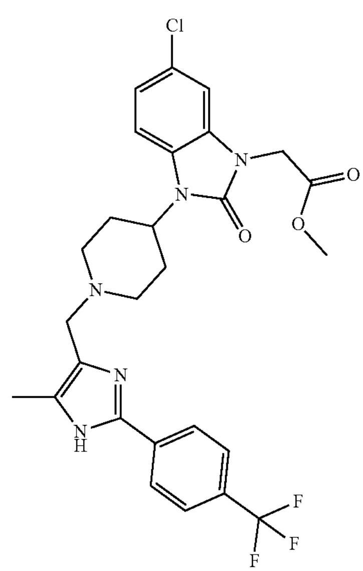 [SMILES: COC(=O)Cn1c(=O)n(C2CCN(Cc3nc(-c4ccc(C(F)(F)F)cc4)[nH]c3C)CC2)c2ccc(Cl)cc21] | 562.3 (M + H)+ | 4-(Chloromethyl)-5-methyl-2-[4-(trifluoromethyl)phenyl]-1H-imidazole; hydrochloride (Intermediate 1)/Methyl 2-[6-chloro-2-oxo-3-(4-piperidyl)benzimidazol-1-yl]acetate (Intermediate 35) |

-continued

| Ex. | Name | Structure | MS (ESI) | Reagents |
|---|---|---|---|---|
| 35 | 5-Chloro-3-(2-methanesulfonyl-ethyl)-1-{1-[5-methyl-2-(4-trifluoromethyl-phenyl)-1H-imidazol-4-ylmethyl]-piperidin-4-yl}-1,3-dihydro-benzoimidazol-2-one | 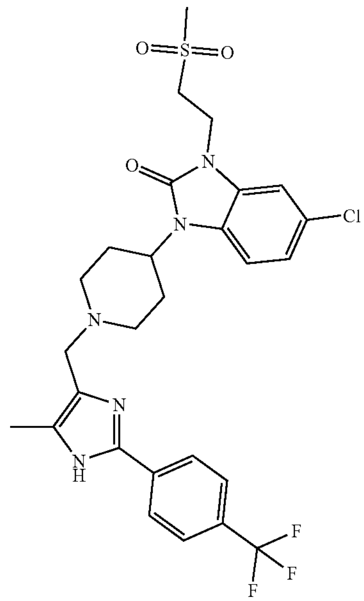 [SMILES: Cc1[nH]c(-c2ccc(C(F)(F)F)cc2)nc1CN1CCC(n2c(=O)n(CCS(C)(=O)=O)c3cc(Cl)ccc32)CC1] | 596.3 (M + H)+ | 4-(Chloromethyl)-5-methyl-2-[4-(trifluoromethyl)phenyl]-1H-imidazole; hydrochloride (Intermediate 1)/5-Chloro-3-(2-methylsulfonylethyl)-1-(4-piperidyl)benzimidazol-2-one (Intermediate 36) |
| 36 | 3-{1-[5-Methyl-2-(4-trifluoromethyl-phenyl)-1H-imidazol-4-ylmethyl]-piperidin-4-yl}-1H-indole | 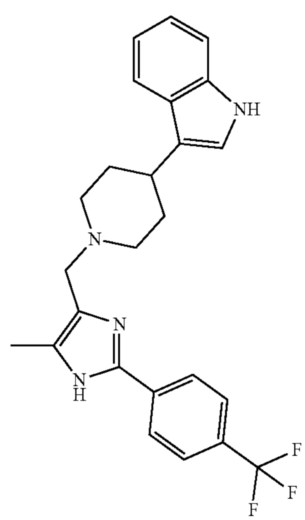 [SMILES: Cc1[nH]c(-c2ccc(C(F)(F)F)cc2)nc1CN1CCC(c2c[nH]c3ccccc23)CC1] | 439.2 (M + H)+ | 4-(Chloromethyl)-5-methyl-2-[4-(trifluoromethyl)phenyl]-1H-imidazole; hydrochloride (Intermediate 1)/3-(4-Piperidyl)-1H-indole (CAS 17403-09-7) |

-continued

| Ex. | Name | Structure | MS (ESI) | Reagents |
|---|---|---|---|---|
| 37 | 6-Fluoro-3-{1-[5-methyl-2-(4-trifluoromethyl-phenyl)-1H-imidazol-4-ylmethyl]-piperidin-4-yl}-benzo[d]isoxazole | 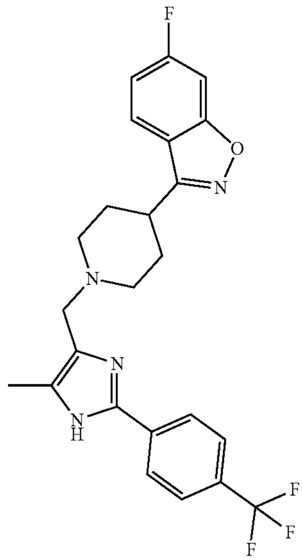 [SMILES: Cc1[nH]c(-c2ccc(C(F)(F)F)cc2)nc1CN1CCC(c2noc3cc(F)ccc23)CC1] | 459.3 (M + H)+ | 4-(Chloromethyl)-5-methyl-2-[4-(trifluoromethyl)phenyl]-1H-imidazole; hydrochloride (Intermediate 1)/6-Fluoro-3-(4-piperidyl)-1,2-benzoxazole (CAS 84163-77-9) |
| 38 | 3-{1-[5-Methyl-2-(4-trifluoromethyl-phenyl)-1H-imidazol-4-ylmethyl]-piperidin-4-yl}-1H-pyrrolo [2,3-b]pyridine | 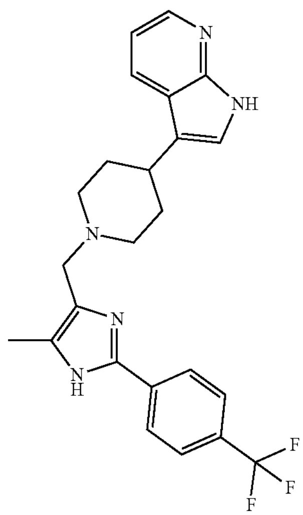 [SMILES: Cc1[nH]c(-c2ccc(C(F)(F)F)cc2)nc1CN1CCC(c2c[nH]c3ncccc23)CC1] | 440.2 (M + H)+ | 4-(Chloromethyl)-5-methyl-2-[4-(trifluoromethyl)phenyl]-1H-imidazole; hydrochloride (Intermediate 1)/3-(4-Piperidyl)-1H-pyrrolo[2,3-b]pyridine (CAS 14692-82-0) |
| 39 | 1-{1-[2-(3-Chloro-4-trifluoromethyl-phenyl)-5-methyl-1H-imidazol-4-ylmethyl]-piperidin-4-yl}-3-methyl-1,3-dihydro-benzoimidazol-2-one | 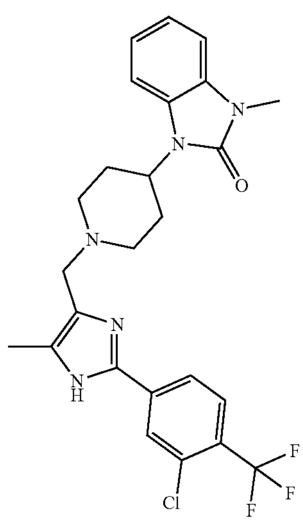 [SMILES: Cc1[nH]c(-c2ccc(C(F)(F)F)c(Cl)c2)nc1CN1CCC(n2c(=O)n(C)c3ccccc32)CC1] | 504.2 (M + H)+ | 4-(Chloromethyl)-2-[3-chloro-4-(trifluoromethyl)phenyl]-5-methyl-1H-imidazole; hydrochloride (Intermediate 6)/1-Methyl-3-(4-piperidyl)benzimidazol-2-one (CAS 53786-10-0) |

-continued

| Ex. | Name | Structure | MS (ESI) | Reagents |
|---|---|---|---|---|
| 40 | 3-{1-[2-(3-Chloro-4-trifluoromethyl-phenyl)-5-methyl-1H-imidazol-4-ylmethyl]-piperidin-4-yl}-3,4-dihydro-1H-quinazolin-2-one | 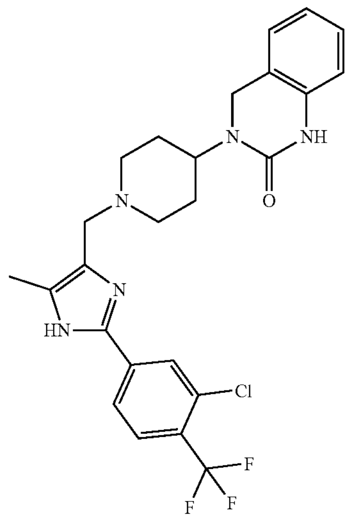 [SMILES: Cc1[nH]c(-c2ccc(C(F)(F)F)c(Cl)c2)nc1CN1CCC(N2Cc3ccccc3NC2=O)CC1] | 503.9 (M + H)+ | 4-(Chloromethyl)-2-[3-chloro-4-(trifluoromethyl)phenyl]-5-methyl-1H-imidazole; hydrochloride (Intermediate 6)/3-(4-Piperidyl)-1,4-dihydroquinazolin-2-one (CAS 79098-75-2) |
| 41 | 1-{1-[2-(3,4-Dichloro-phenyl)-5-methyl-1H-imidazol-4-ylmethyl]-piperidin-4-yl}-3-methyl-1,3-dihydro-benzoimidazol-2-one | 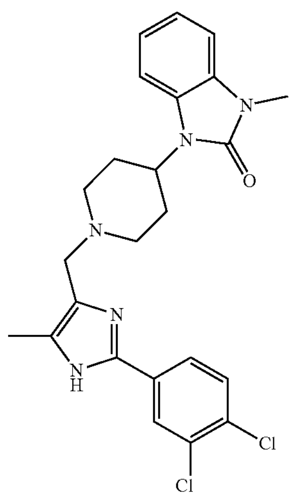 | 470.4 (M + H)+ | 4-(Chloromethyl)-2-(3,4-dichlorophenyl)-5-methyl-1H-imidazole; hydrochloride (Intermediate 7)/1-Methyl-3-(4-piperidyl)benzimidazol-2-one (CAS 53786-10-0) |
| 42 | 3-{1-[2-(3,4-Dichloro-phenyl)-5-methyl-1H-imidazol-4-ylmethyl]-piperidin-4-yl}-3,4-dihydro-1H-quinazolin-2-one | 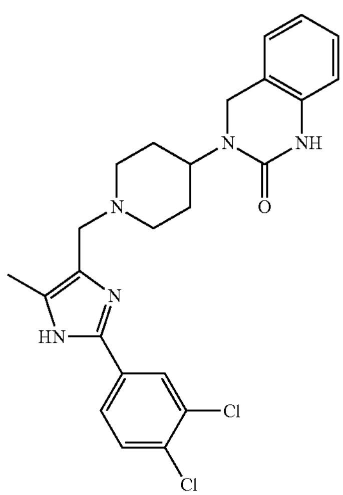 [SMILES: Cc1[nH]c(-c2ccc(Cl)c(Cl)c2)nc1CN1CCC(N2Cc3ccccc3NC2=O)CC1] | 470.4 (M + H)+ | 4-(Chloromethyl)-2-(3,4-dichlorophenyl)-5-methyl-1H-imidazole; hydrochloride (Intermediate 7)/3-(4-Piperidyl)-1,4-dihydroquinazolin-2-one (CAS 79098-75-2) |

-continued

| Ex. | Name | Structure | MS (ESI) | Reagents |
|---|---|---|---|---|
| 43 | 5-Chloro-1-{1-[5-methyl-2-(4-trifluoromethyl-phenyl)-1H-imidazol-4-ylmethyl]-piperidin-4-yl}-1,3-dihydro-indol-2-one | 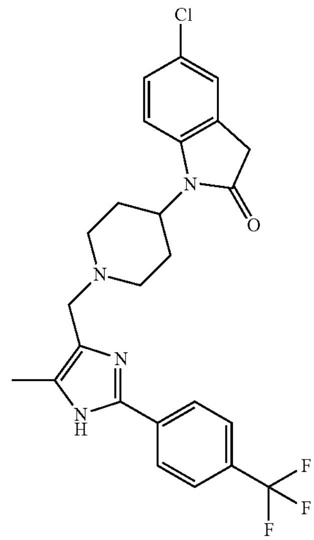 [SMILES: Cc1[nH]c(-c2ccc(C(F)(F)F)cc2)nc1CN1CCC(N2C(=O)Cc3cc(Cl)ccc32)CC1] | 489.0 (M + H)+ | 4-(Chloromethyl)-5-methyl-2-[4-(trifluoromethyl)phenyl]-1H-imidazole; hydrochloride (Intermediate 1)/5-Chloro-1-(4-piperidyl)indolin-2-one (Intermediate 41) |
| 44 | 1-{1-[2-(3-Fluoro-4-trifluoromethyl-phenyl)-5-methyl-1H-imidazol-4-ylmethyl]-piperidin-4-yl}-3-methyl-1,3-dihydro-benzoimidazol-2-one | 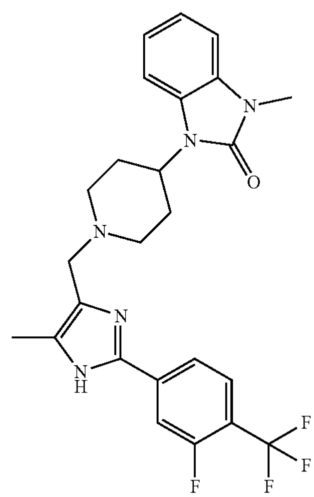 [SMILES: Cc1[nH]c(-c2ccc(C(F)(F)F)c(F)c2)nc1CN1CCC(n2c(=O)n(C)c3ccccc32)CC1] | 488.0 (M + H)+ | 4-(Chloromethyl)-2-[3-fluoro-4-(trifluoromethyl)phenyl]-5-methyl-1H-imidazole; hydrochloride (Intermediate 8)/1-Methyl-3-(4-piperidyl)benzimidazol-2-one (CAS 53786-10-0) |
| 45 | 3-{1-[2-(3-Chloro-4-trifluoromethyl-phenyl)-5-methyl-1H-imidazol-4-ylmethyl]-piperidin-4-yl}-7-fluoro-3,4-dihydro-1H-quinazolin-2-one | 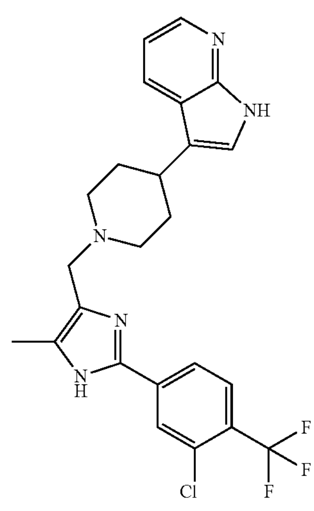 | 522.0 (M + H)+ | 4-(Chloromethyl)-2-[3-chloro-4-(trifluoromethyl)phenyl]-5-methyl-1H-imidazole; hydrochloride (Intermediate 6)/7-Fluoro-3-(4-piperidyl)-1,4-dihydroquinazolin-2-one (Intermediate 39) |

| Ex. | Name | Structure | MS (ESI) | Reagents |
|---|---|---|---|---|
| 46 | 3-{1-[2-(3-Chloro-4-trifluoromethyl-phenyl)-5-methyl-1H-imidazol-4-ylmethyl]-piperidin-4-yl}-1H-pyrrolo[2,3-b]pyridine | 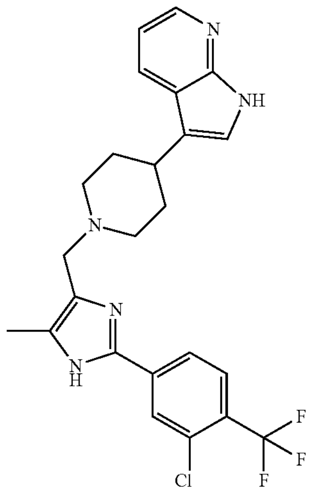 [SMILES: Cc1[nH]c(-c2ccc(C(F)(F)F)c(Cl)c2)nc1CN1CCC(c2c[nH]c3ncccc23)CC1] | 474.0 (M + H)+ | 4-(Chloromethyl)-2-[3-chloro-4-(trifluoromethyl)phenyl]-5-methyl-1H-imidazole; hydrochloride (Intermediate 6)/3-(4-Piperidyl)-1H-pyrrolo[2,3-b]pyridine (CAS 14692-82-0) |
| 47 | 3-{1-[2-(3-Fluoro-4-trifluoromethyl-phenyl)-5-methyl-1H-imidazol-4-ylmethyl]-piperidin-4-yl}-3,4-dihydro-1H-quinazolin-2-one | 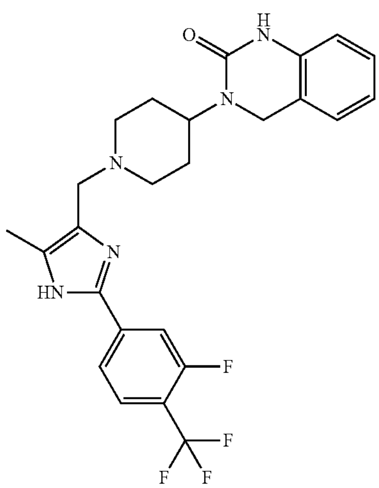 [SMILES: Cc1[nH]c(-c2ccc(C(F)(F)F)c(F)c2)nc1CN1CCC(N2Cc3ccccc3NC2=O)CC1] | 488.2 (M + H)+ | 4-(Chloromethyl)-2-[3-fluoro-4-(trifluoromethyl)phenyl]-5-methyl-1H-imidazole; hydrochloride (Intermediate 8)/3-(4-Piperidyl)-1,4-dihydroquinazolin-2-one (CAS 79098-75-2) |
| 48 | 3-{1-[2-(3,4-Dichloro-phenyl)-5-methyl-1H-imidazol-4-ylmethyl]-piperidin-4-yl}-7-fluoro-3,4-dihydro-1H-quinazolin-2-one | 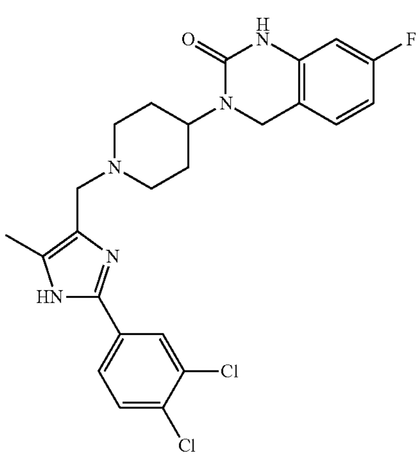 [SMILES: Cc1[nH]c(-c2ccc(Cl)c(Cl)c2)nc1CN1CCC(N2Cc3ccc(F)cc3NC2=O)CC1] | 488.2 (M + H)+ | 4-(Chloromethyl)-2-(3,4-dichlorophenyl)-5-methyl-1H-imidazole; hydrochloride (Intermediate 7)/7-Fluoro-3-(4-piperidyl)-1,4-dihydroquinazolin-2-one (Intermediate 39) |

-continued

| Ex. | Name | Structure | MS (ESI) | Reagents |
|---|---|---|---|---|
| 49 | 3-{1-[2-(3,4-Dichloro-phenyl)-5-methyl-1H-imidazol-4-ylmethyl]-piperidin-4-yl}-1H-pyrrolo[2,3-b]pyridine | 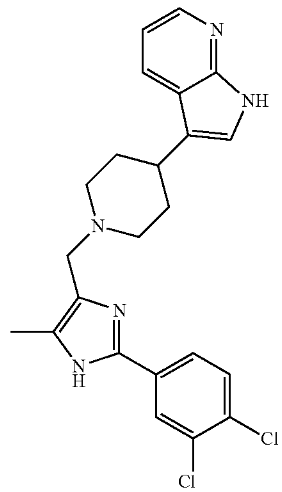 [SMILES: Cc1[nH]c(-c2ccc(Cl)c(Cl)c2)nc1CN1CCC(c2c[nH]c3ncccc23)CC1] | 440.2 (M + H)⁺ | 4-(Chloromethyl)-2-(3,4-dichlorophenyl)-5-methyl-1H-imidazole; hydrochloride (Intermediate 7)/3-(4-Piperidyl)-1H-pyrrolo[2,3-b]pyridine (CAS 14692-82-0) |
| 50 | 3-{1-[2-(4-Chloro-3-fluoro-phenyl)-5-methyl-1H-imidazol-4-ylmethyl]-piperidin-4-yl}-3,4-dihydro-1H-quinazolin-2-one | 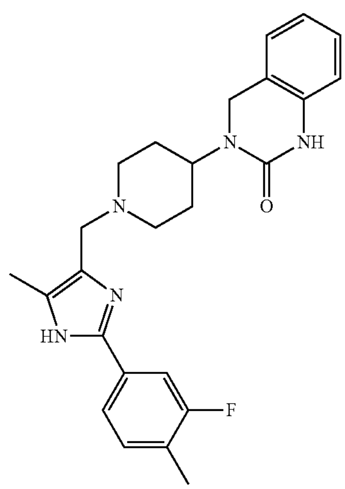 | 454.1 (M + H)⁺ | 2-(4-Chloro-3-fluoro-phenyl)-4-(chloromethyl)-5-methyl-1H-imidazole; hydrochloride (Intermediate 9)/3-(4-Piperidyl)-1,4-dihydroquinazolin-2-one (CAS 79098-75-2) |
| 51 | 1-{1-[2-(4-Chloro-3-fluoro-phenyl)-5-methyl-1H-imidazol-4-ylmethyl]-piperidin-4-yl}-3-methyl-1,3-dihydro-benzoimidazol-2-one | 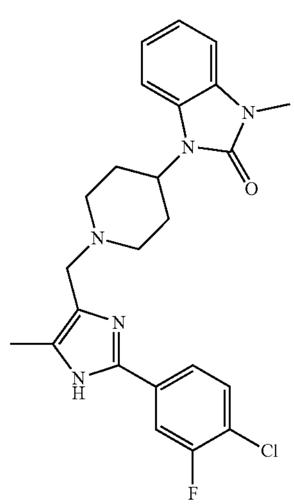 | 454.2 (M + H)⁺ | 2-(4-Chloro-3-fluoro-phenyl)-4-(chloromethyl)-5-methyl-1H-imidazole; hydrochloride (Intermediate 9)/1-Methyl-3-(4-piperidyl)benzimidazol-2-one (CAS 53786-10-0) |

| Ex. | Name | Structure | MS (ESI) | Reagents |
|---|---|---|---|---|
| 53 | 1-Methyl-3-{1-[5-methyl-2-(4-trifluoromethyl-phenyl)-1H-imidazol-4-ylmethyl]-piperidin-4-yl}-3,4-dihydro-1H-quinazolin-2-one | 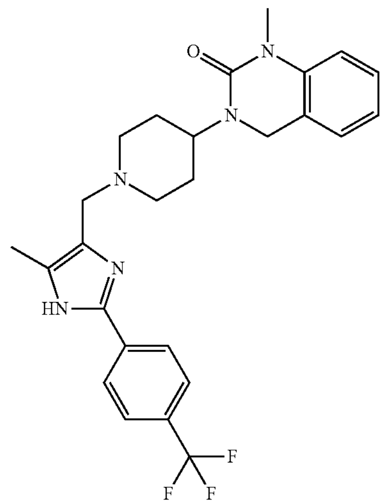 [SMILES: Cc1[nH]c(-c2ccc(C(F)(F)F)cc2)nc1CN1CCC(N2Cc3ccccc3N(C)C2=O)CC1] | 484.5 (M + H)+ | 4-(Chloromethyl)-5-methyl-2-[4-(trifluoromethyl)phenyl]-1H-imidazole; hydrochloride (Intermediate 1)/1-Methyl-3-(4-piperidyl)-4H-quinazolin-2-one (Intermediate 37) |
| 54 | 1-(2-Methoxy-ethyl)-3-{1-[5-methyl-2-(4-trifluoromethyl-phenyl)-1H-imidazol-4-ylmethyl]-piperidin-4-yl}-3,4-dihydro-1H-quinazolin-2-one | 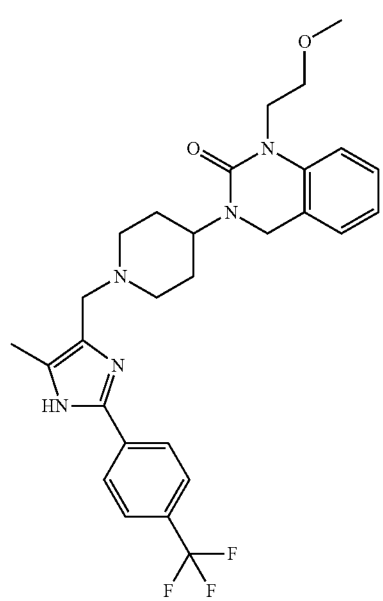 [SMILES: COCCN1C(=O)N(C2CCN(Cc3nc(-c4ccc(C(F)(F)F)cc4)[nH]c3C)CC2)Cc2ccccc21] | 528.3 (M + H)+ | 4-(Chloromethyl)-5-methyl-2-[4-(trifluoromethyl)phenyl]-1H-imidazole; hydrochloride (Intermediate 1)/1-(2-Methoxyethyl)-3-(4-piperidyl)-4H-quinazolin-2-one (Intermediate 38) |

| Ex. | Name | Structure | MS (ESI) | Reagents |
|---|---|---|---|---|
| 55 | 3-{1-[5-(2-Methoxy-ethyl)-2-(4-trifluoromethyl-phenyl)-1H-imidazol-4-ylmethyl]-piperidin-4-yl}-3,4-dihydro-1H-quinazolin-2-one | 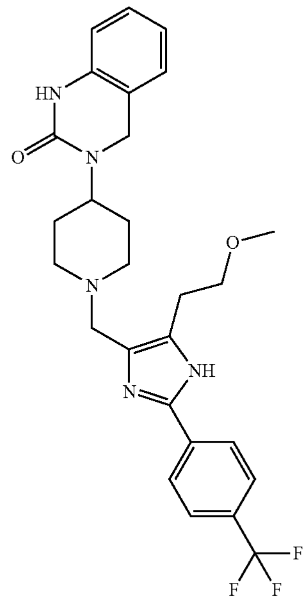 [SMILES: COCCc1[nH]c(-c2ccc(C(F)(F)F)cc2)nc1CN1CCC(N2Cc3ccccc3NC2=O)CC1] | 514.4 (M + H)+ | 4-(Chloromethyl)-5-(2-methoxyethyl)-2-[4-(trifluoromethyl)phenyl]-1H-imidazole; hydrochloride (Intermediate 17)/3-(4-Piperidyl)-1,4-dihydroquinazolin-2-one (CAS 79098-75-2) |
| 56 | 3-{1-[5-Benzyl-2-(4-trifluoromethyl-phenyl)-1H-imidazol-4-ylmethyl]-piperidin-4-yl}-3,4-dihydro-1H-quinazolin-2-one | 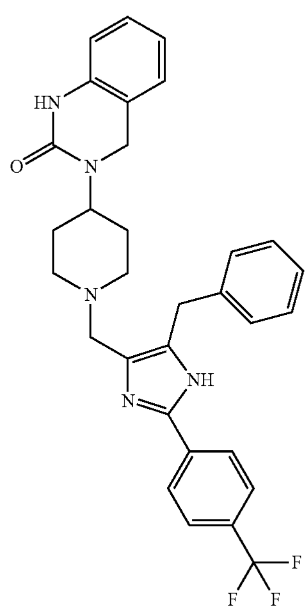 [SMILES: O=C1Nc2ccccc2CN1C1CCN(Cc2nc(-c3ccc(C(F)(F)F)cc3)[nH]c2Cc2ccccc2)CC1] | 546.2 (M + H)+ | 5-Benzyl-4-(chloromethyl)-2-[4-(trifluoromethyl)phenyl]-1H-imidazole; hydrochloride (Intermediate 19)/3-(4-Piperidyl)-1,4-dihydroquinazolin-2-one (CAS 79098-75-2) |

-continued

| Ex. | Name | Structure | MS (ESI) | Reagents |
|---|---|---|---|---|
| 57 | 3-{1-[2-(2,4-Dichloro-phenyl)-5-methyl-1H-imidazol-4-ylmethyl]-piperidin-4-yl}-3,4-dihydro-1H-quinazolin-2-one | 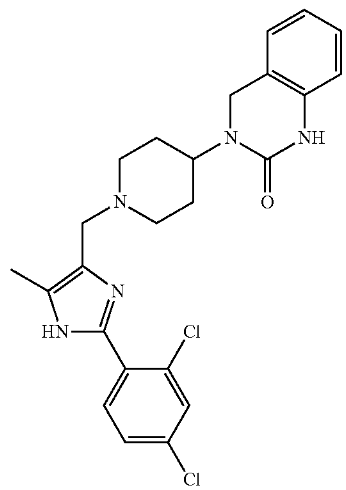 [SMILES: Cc1[nH]c(-c2ccc(Cl)cc2Cl)nc1CN1CCC(N2Cc3ccccc3NC2=O)CC1] | 470.3 (M + H)+ | 4-(Chloromethyl)-2-(2,4-dichlorophenyl)-5-methyl-1H-imidazole; hydrochloride (Intermediate 10)/3-(4-Piperidyl)-1,4-dihydroquinazolin-2-one (CAS 79098-75-2) |
| 58 | 1-{1-[2-(2,4-Dichloro-phenyl)-5-methyl-1H-imidazol-4-ylmethyl]-piperidin-4-yl}-3-methyl-1,3-dihydro-benzoimidazol-2-one | 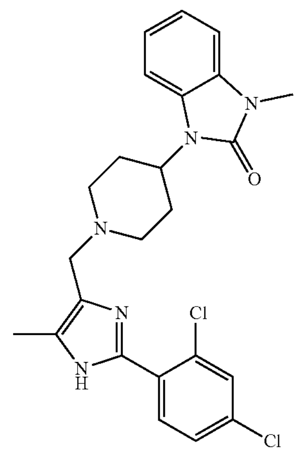 | 470.3 (M + H)+ | 4-(Chloromethyl)-2-(2,4-dichlorophenyl)-5-methyl-1H-imidazole; hydrochloride (Intermediate 10)/1-Methyl-3-(4-piperidyl)benzimidazol-2-one (CAS 53786-10-0) |
| 59 | 3-{1-[2-(2-Chloro-4-trifluoromethyl-phenyl)-5-methyl-1H-imidazol-4-ylmethyl]-piperidin-4-yl}-3,4-dihydro-1H-quinazolin-2-one | 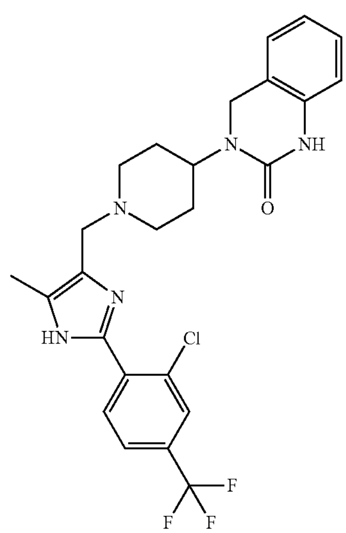 [SMILES: Cc1[nH]c(-c2ccc(C(F)(F)F)cc2Cl)nc1CN1CCC(N2Cc3ccccc3NC2=O)CC1] | 504.1 (M + H)+ | 4-(Chloromethyl)-2-[2-chloro-4-(trifluoromethyl)phenyl]-5-methyl-1H-imidazole; hydrochloride (Intermediate 11)/3-(4-Piperidyl)-1,4-dihydroquinazolin-2-one (CAS 79098-75-2) |

| Ex. | Name | Structure | MS (ESI) | Reagents |
|---|---|---|---|---|
| 60 | 1-{1-[2-(2-Chloro-4-trifluoromethyl-phenyl)-5-methyl-1H-imidazol-4-ylmethyl]-piperidin-4-yl}-3-methyl-1,3-dihydro-benzoimidazol-2-one | 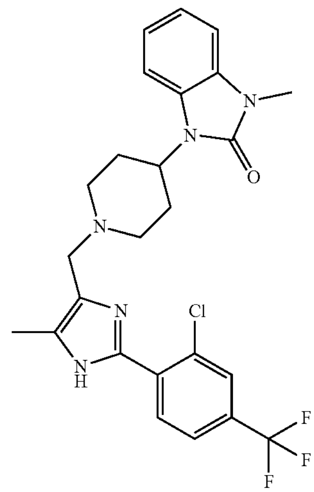 [SMILES: Cc1[nH]c(-c2ccc(C(F)(F)F)cc2Cl)nc1CN1CCC(n2c(=O)n(C)c3ccccc32)CC1] | 504.1 (M + H)+ | 4-(Chloromethyl)-2-[2-chloro-4-(trifluoromethyl)phenyl]-5-methyl-1H-imidazole; hydrochloride (Intermediate 11)/1-Methyl-3-(4-piperidyl)benzimidazol-2-one (CAS 53786-10-0) |
| 61 | 3-{1-[5-(2-Methoxy-ethyl)-2-(4-trifluoromethyl-phenyl)-1H-imidazol-4-ylmethyl]-piperidin-4-yl}-1H-pyrrolo[3,2-c]pyridine | 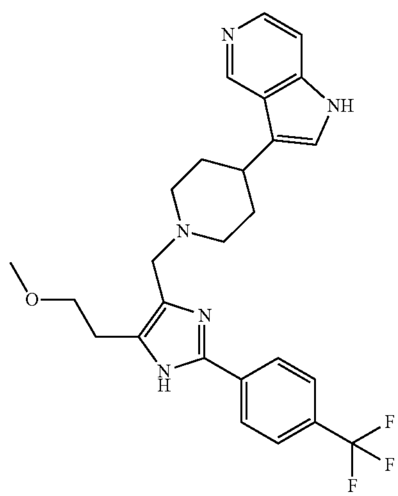 [SMILES: COCCc1[nH]c(-c2ccc(C(F)(F)F)cc2)nc1CN1CCC(c2c[nH]c3ccncc23)CC1] | 482.5 (M − H)− | 4-(Chloromethyl)-5-(2-methoxyethyl)-2-[4-(trifluoromethyl)phenyl]-1H-imidazole; hydrochloride (Intermediate 17)/3-(4-Piperidyl)-1H-pyrrolo[3,2-c]pyridine (Intermediate 40) |
| 62 | 3-{1-[5-Propyl-2-(4-trifluoromethyl-phenyl)-1H-imidazol-4-ylmethyl]-piperidin-4-yl}-3,4-dihydro-1H-quinazolin-2-one | 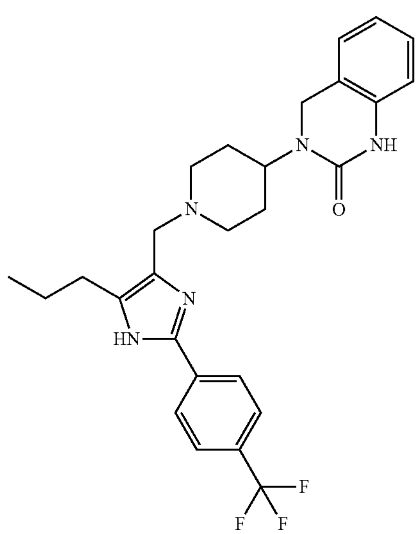 [SMILES: CCCc1[nH]c(-c2ccc(C(F)(F)F)cc2)nc1CN1CCC(N2Cc3ccccc3NC2=O)CC1] | 498.5 (M + H)+ | 4-(Chloromethyl)-5-propyl-2-[4-(trifluoromethyl)phenyl]-1H-imidazole; hydrochloride (Intermediate 18)/3-(4-Piperidyl)-1,4-dihydroquinazolin-2-one (CAS 79098-75-2) |

-continued

| Ex. | Name | Structure | MS (ESI) | Reagents |
|---|---|---|---|---|
| 63 | 3-{1-[5-Methyl-2-(4-trifluoromethyl-phenyl)-1H-imidazol-4-ylmethyl]-piperidin-4-yl}-1H-pyrrolo[3,2-c]pyridine | 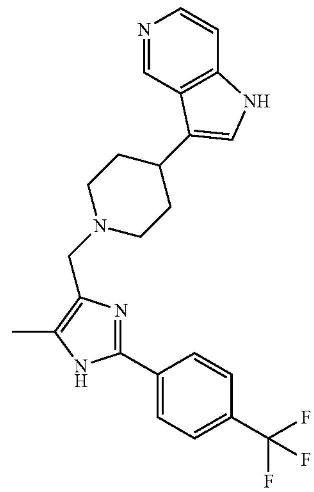 [SMILES: Cc1[nH]c(-c2ccc(C(F)(F)F)cc2)nc1CN1CCC(c2c[nH]c3ccncc23)CC1] | 438.4 (M − H)⁻ | 4-(Chloromethyl)-5-methyl-2-[4-(trifluoromethyl)phenyl]-1H-imidazole; hydrochloride (Intermediate 1)/3-(4-Piperidyl)-1H-pyrrolo[3,2-c]pyridine (Intermediate 40) |
| 64 | 1-Methyl-3-{1-[5-propyl-2-(4-trifluoromethyl-phenyl)-1H-imidazol-4-ylmethyl]-piperidin-4-yl}-1,3-dihydro-benzoimidazol-2-one | 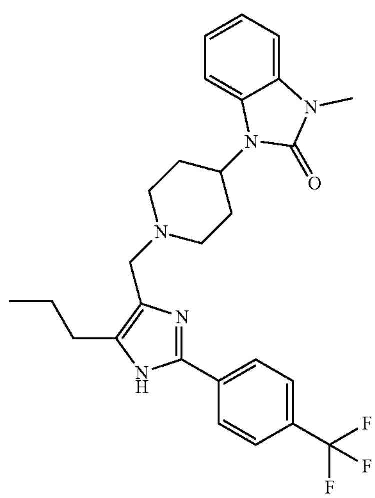 [SMILES: CCCc1[nH]c(-c2ccc(C(F)(F)F)cc2)nc1CN1CCC(n2c(=O)n(C)c3ccccc32)CC1] | 498.3 (M + H)⁺ | 4-(Chloromethyl)-5-propyl-2-[4-(trifluoromethyl)phenyl]-1H-imidazole; hydrochloride (Intermediate 18)/1-Methyl-3-(4-piperidyl)benzimidazol-2-one (CAS 53786-10-0) |
| 65 | 1-Methyl-3-{1-[2-methyl-5-(4-trifluoromethyl-phenyl)-2H-[1,2,4]triazol-3-ylmethyl]-piperidin-4-yl}-1,3-dihydro-benzoimidazol-2-one | 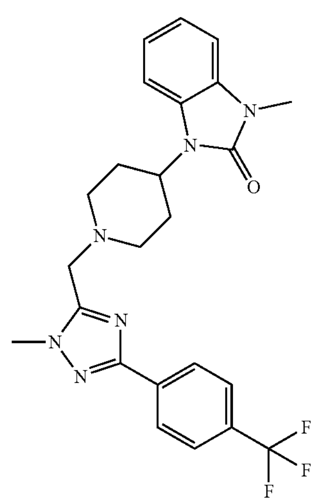 [SMILES: Cn1nc(-c2ccc(C(F)(F)F)cc2)nc1CN1CCC(n2c(=O)n(C)c3ccccc32)CC1] | 471.2 (M + H)⁺ | 5-(Chloromethyl)-1-methyl-3-[4-(trifluoromethyl)phenyl]-1,2,4-triazole (Intermediate 22)/1-Methyl-3-(4-piperidyl)benzimidazol-2-one (CAS 53786-10-0) |

| Ex. | Name | Structure | MS (ESI) | Reagents |
|---|---|---|---|---|
| 66 | 3-{1-[1-Methyl-5-(4-trifluoromethyl-phenyl)-1H-[1,2,4]triazol-3-ylmethyl]-piperidin-4-yl}-3,4-dihydro-1H-quinazolin-2-one | 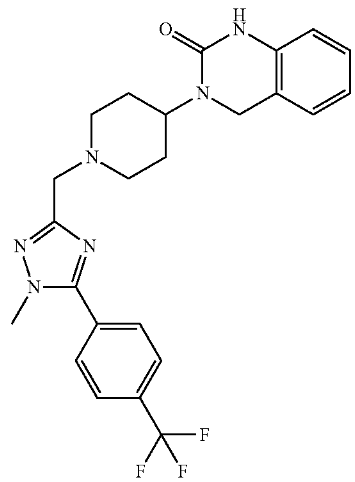 [SMILES: Cn1nc(CN2CCC(N3Cc4ccccc4NC3=O)CC2)nc1-c1ccc(C(F)(F)F)cc1] | 471.2 (M + H)$^+$ | 3-(Chloromethyl)-1-methyl-5-[4-(trifluoromethyl)phenyl]-1,2,4-triazole (Intermediate 23)/3-(4-Piperidyl)-1,4-dihydroquinazolin-2-one (CAS 79098-75-2) |
| 67 | 1-Methyl-3-{1-[1-methyl-5-(4-trifluoromethyl-phenyl)-1H-[1,2,4]triazol-3-ylmethyl]-piperidin-4-yl}-1,3-dihydro-benzoimidazol-2-one | 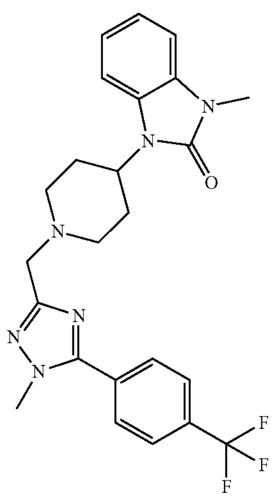 [SMILES: Cn1nc(CN2CCC(n3c(=O)n(C)c4ccccc43)CC2)nc1-c1ccc(C(F)(F)F)cc1] | 471.2 (M + H)$^+$ | 3-(Chloromethyl)-1-methyl-5-[4-(trifluoromethyl)phenyl]-1,2,4-triazole (Intermediate 23)/1-Methyl-3-(4-piperidyl)benzimidazol-2-one (CAS 53786-10-0) |
| 68 | 3-{1-[4-Methyl-1-(4-trifluoromethyl-phenyl)-1H-pyrazol-3-ylmethyl]-piperidin-4-yl}-3,4-dihydro-1H-quinazolin-2-one | 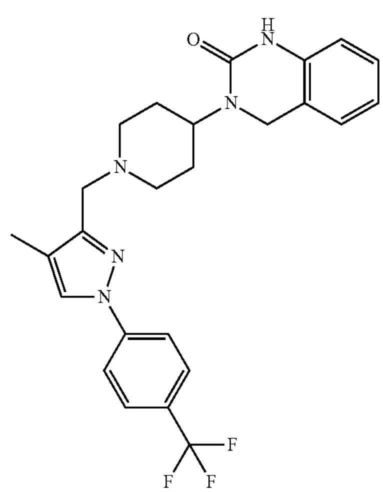 [SMILES: Cc1cn(-c2ccc(C(F)(F)F)cc2)nc1CN1CCC(N2Cc3ccccc3NC2=O)CC1] | 470.3 (M + H)$^+$ | 3-(chloromethyl)-4-methyl-1-[4-(trifluoromethyl)phenyl]pyrazole (Intermediate 24)/3-(4-Piperidyl)-1,4-dihydroquinazolin-2-one (CAS 79098-75-2) |

-continued

| Ex. | Name | Structure | MS (ESI) | Reagents |
|---|---|---|---|---|
| 69 | 1-Methyl-3-{1-[4-methyl-1-(4-trifluoromethyl-phenyl)-1H-pyrazol-3-ylmethyl]-piperidin-4-yl}-1,3-dihydro-benzoimidazol-2-one | 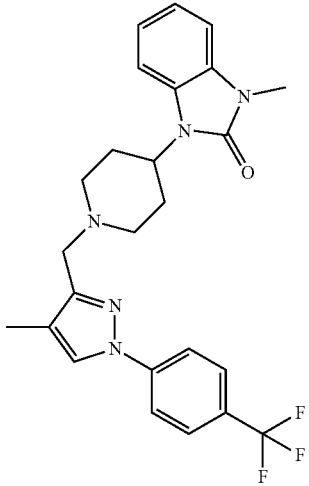 [SMILES: Cc1cn(-c2ccc(C(F)(F)F)cc2)nc1CN1CCC(n2c(=O)n(C)c3ccccc32)CC1] | 470.3 (M + H)+ | 3-(chloromethyl)-4-methyl-1-[4-(trifluoromethyl)phenyl]pyrazole (Intermediate 24)/1-Methyl-3-(4-piperidyl)benzimidazol-2-one (CAS 53786-10-0) |
| 70 | 1-{1-[1,5-Dimethyl-2-(4-trifluoromethyl-phenyl)-1H-imidazol-4-ylmethyl]-piperidin-4-yl}-3-methyl-1,3-dihydro-benzoimidazol-2-one | 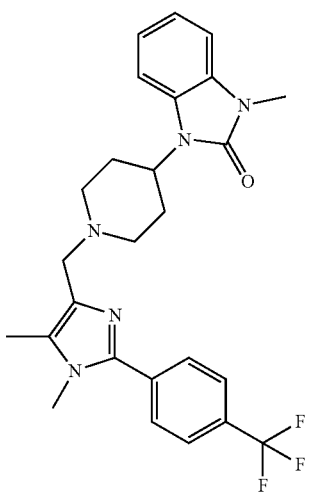 [SMILES: Cc1c(CN2CCC(n3c(=O)n(C)c4ccccc43)CC2)nc(-c2ccc(C(F)(F)F)cc2)n1C] | 484.5 (M + H)+ | 4-(Chloromethyl)-1,5-dimethyl-2-[4-(trifluoromethyl)phenyl]imidazole; hydrochloride (Intermediate 20)/1-Methyl-3-(4-piperidyl)benzimidazol-2-one (CAS 53786-10-0) |
| 71 | 3-{1-[1,5-Dimethyl-2-(4-trifluoromethyl-phenyl)-1H-imidazol-4-ylmethyl]-piperidin-4-yl}-3,4-dihydro-1H-quinazolin-2-on | 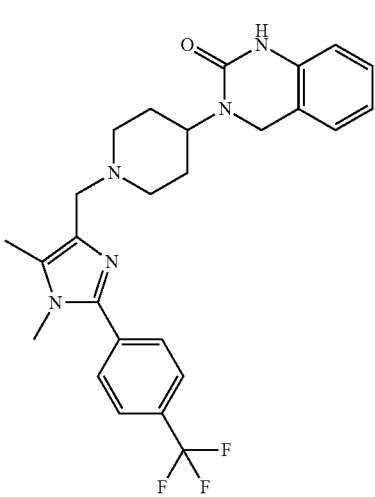 [SMILES: Cc1c(CN2CCC(N3Cc4ccccc4NC3=O)CC2)nc(-c2ccc(C(F)(F)F)cc2)n1C] | 484.5 (M + H)+ | 4-(Chloromethyl)-1,5-dimethyl-2-[4-(trifluoromethyl)phenyl]imidazole; hydrochloride (Intermediate 20)/3-(4-Piperidyl)-1,4-dihydroquinazolin-2-one (CAS 79098-75-2) |

| Ex. | Name | Structure | MS (ESI) | Reagents |
|---|---|---|---|---|
| 72 | 3-{1-[5-Methyl-2-(4-trifluoromethanesulfonyl-phenyl)-1H-imidazol-4-ylmethyl]-piperidin-4-yl}-3,4-dihydro-1H-quinazolin-2-one | 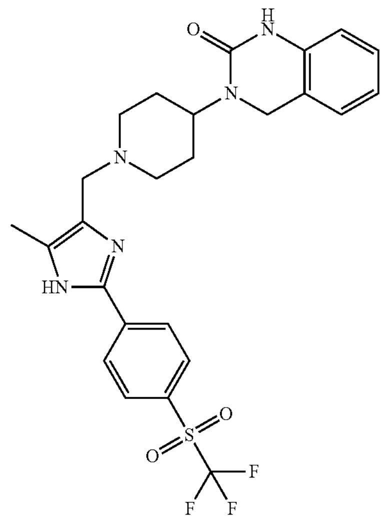 [SMILES: Cc1[nH]c(-c2ccc(S(=O)(=O)C(F)(F)F)cc2)nc1CN1CCC(N2Cc3ccccc3NC2=O)CC1] | 534.3 (M + H)⁺ | 4-(Chloromethyl)-5-methyl-2-[4-(trifluoromethylsulfonyl)phenyl]-1H-imidazole; hydrochloride (Intermediate 13)/3-(4-Piperidyl)-1,4-dihydroquinazolin-2-one (CAS 79098-75-2) |
| 73 | 1-{1-[2-(4-Methanesulfonyl-phenyl)-5-methyl-1H-imidazol-4-ylmethyl]-piperidin-4-yl}-3-methyl-1,3-dihydro-benzoimidazol-2-one | 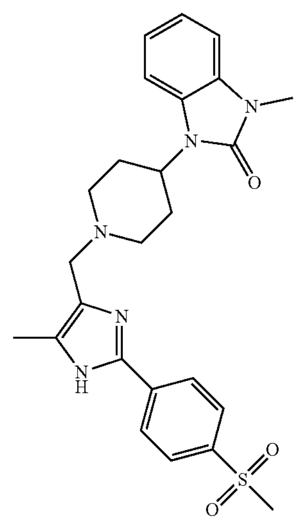 | 480.4 (M + H)⁺ | 4-(Chloromethyl)-5-methyl-2-(4-methylsulfonylphenyl)-1H-imidazole; hydrochloride (Intermediate 12)/1-Methyl-3-(4-piperidyl)benzimidazol-2-one (CAS 53786-10-0) |
| 74 | 3-{1-[2-(4-Methanesulfonyl-phenyl)-5-methyl-1H-imidazol-4-ylmethyl]-piperidin-4-yl}-3,4-dihydro-1H-quinazolin-2-one | 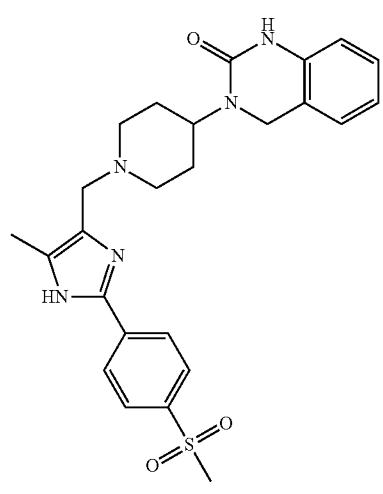 [SMILES: Cc1[nH]c(-c2ccc(S(C)(=O)=O)cc2)nc1CN1CCC(N2Cc3ccccc3NC2=O)CC1] | 480.1 (M + H)⁺ | 4-(Chloromethyl)-5-methyl-2-(4-methylsulfonylphenyl)-1H-imidazole; hydrochloride (Intermediate 12)/3-(4-Piperidyl)-1,4-dihydroquinazolin-2-one (CAS 79098-75-2) |

-continued

| Ex. | Name | Structure | MS (ESI) | Reagents |
|---|---|---|---|---|
| 75 | 1-Methyl-3-{1-[5-methyl-2-(4-trifluoromethanesulfonyl-phenyl)-1H-imidazol-4-ylmethyl]-piperidin-4-yl}-1,3-dihydro-benzoimidazol-2-one | 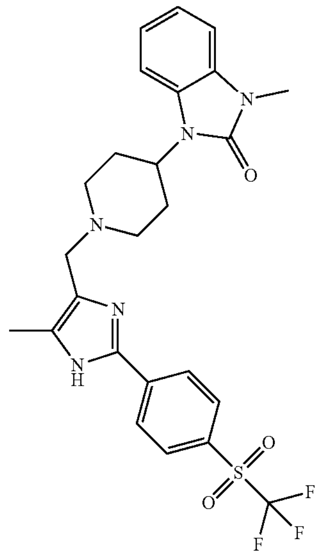 [SMILES: Cc1[nH]c(-c2ccc(S(=O)(=O)C(F)(F)F)cc2)nc1CN1CCC(n2c(=O)n(C)c3ccccc32)CC1] | 534.3 (M + H)+ | 4-(Chloromethyl)-5-methyl-2-[4-(trifluoromethylsulfonyl)phenyl]-1H-imidazole; hydrochloride (Intermediate 13)/1-Methyl-3-(4-piperidyl)benzimidazol-2-one (CAS 53786-10-0) |
| 76 | 3-{1-[1-(2-Methoxy-ethyl)-5-methyl-2-(4-trifluoromethyl-phenyl)-1H-imidazol-4-ylmethyl]-piperidin-4-yl}-3,4-dihydro-1H-quinazolin-2-one | 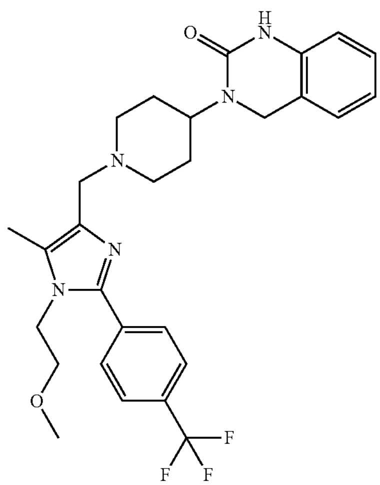 [SMILES: COCCn1c(-c2ccc(C(F)(F)F)cc2)nc(CN2CCC(N3Cc4ccccc4NC3=O)CC2)c1C] | 528.1 (M + H)+ | 4-(Chloromethyl)-1-(2-methoxyethyl)-5-methyl-2-[4-(trifluoromethyl)phenyl]imidazole; hydrochloride (Intermediate 21)/3-(4-Piperidyl)-1,4-dihydroquinazolin-2-one (CAS 79098-75-2) |
| 77 | 3-{1-[5-Methyl-2-(4-trifluoromethanesulfonyl-phenyl)-1H-imidazol-4-ylmethyl]-piperidin-4-yl}-1H-pyrrolo[3,2-c]pyridine | 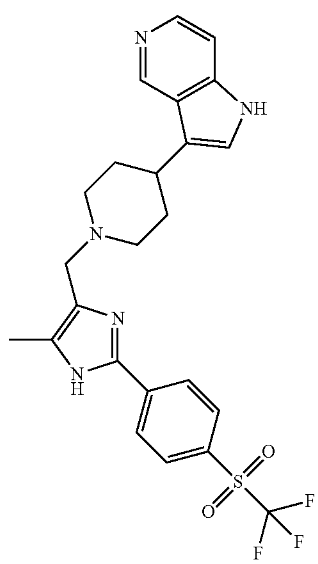 [SMILES: Cc1[nH]c(-c2ccc(S(=O)(=O)C(F)(F)F)cc2)nc1CN1CCC(c2c[nH]c3ccncc23)CC1] | 504.1 (M + H)+ | 4-(Chloromethyl)-5-methyl-2-[4-(trifluoromethylsulfonyl)phenyl]-1H-imidazole; hydrochloride (Intermediate 13)/3-(4-Piperidyl)-1H-pyrrolo[3,2-c]pyridine (Intermediate 40) |

| Ex. | Name | Structure | MS (ESI) | Reagents |
|---|---|---|---|---|
| 78 | 3-(1-{5-Methyl-2-[4-(2-methyl-propane-1-sulfonyl)-phenyl]-1H-imidazol-4-ylmethyl}-piperidin-4-yl)-3,4-dihydro-1H-quinazolin-2-one | 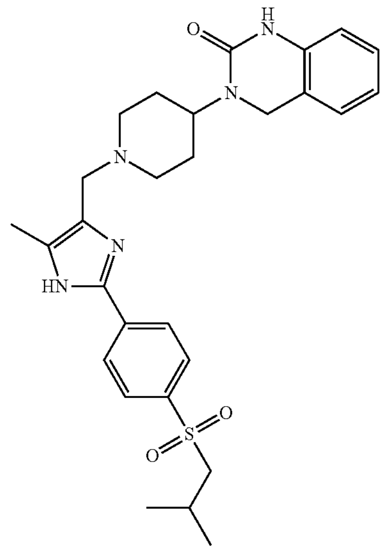 [SMILES: Cc1[nH]c(-c2ccc(S(=O)(=O)CC(C)C)cc2)nc1CN1CCC(N2Cc3ccccc3NC2=O)CC1] | 522.3 (M + H)+ | 4-(Chloromethyl)-2-(4-isobutylsulfonylphenyl)-5-methyl-1H-imidazole; hydrochloride (Intermediate 14)/3-(4-Piperidyl)-1,4-dihydroquinazolin-2-one (CAS 79098-75-2) |
| 79 | 1-Methyl-3-(1-{5-methyl-2-[4-(2-methyl-propane-1-sulfonyl)-phenyl]-1H-imidazol-4-ylmethyl}-piperidin-4-yl)-1,3-dihydro-benzoimidazol-2-one | 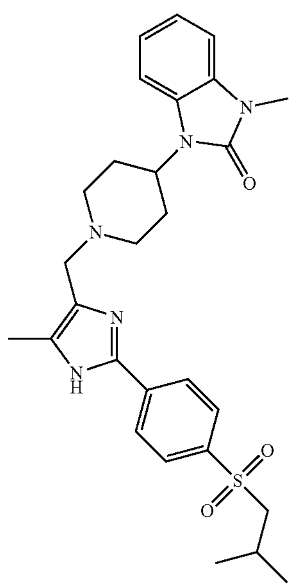 | 522.3 (M + H)+ | 4-(Chloromethyl)-2-(4-isobutylsulfonylphenyl)-5-methyl-1H-imidazole; hydrochloride (Intermediate 14)/1-Methyl-3-(4-piperidyl)benzimidazol-2-one (CAS 53786-10-0) |

-continued

| Ex. | Name | Structure | MS (ESI) | Reagents |
|---|---|---|---|---|
| 80 | 3-{1-[5-Methyl-2-(4-phenylmethanesulfonyl-phenyl)-1H-imidazol-4-ylmethyl]-piperidin-4-yl}-3,4-dihydro-1H-quinazolin-2-one | 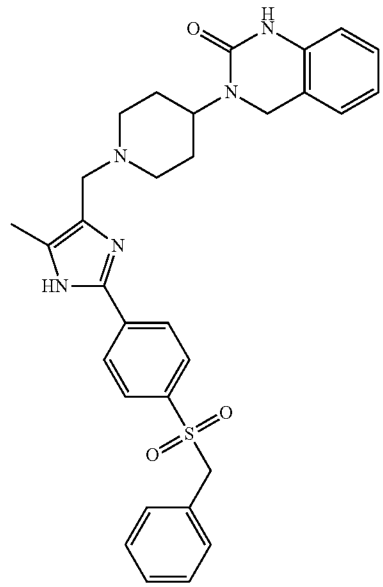 [SMILES: Cc1[nH]c(-c2ccc(S(=O)(=O)Cc3ccccc3)cc2)nc1CN1CCC(N2Cc3ccccc3NC2=O)CC1] | 556.2 (M + H)+ | 2-(4-Benzylsulfonylphenyl)-4-(chloromethyl)-5-methyl-1H-imidazole; hydrochloride (Intermediate 15)/3-(4-Piperidyl)-1,4-dihydroquinazolin-2-one (CAS 79098-75-2) |
| 81 | 1-Methyl-3-{1-[5-methyl-2-(4-phenylmethanesulfonyl-phenyl)-1H-imidazol-4-ylmethyl]-piperidin-4-yl}-1,3-dihydro-benzoimidazol-2-one | 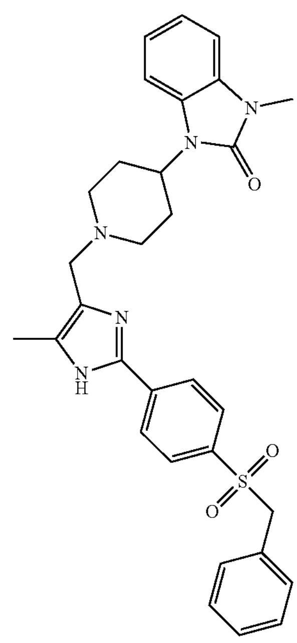 | 556.1 (M + H)+ | 2-(4-Benzylsulfonylphenyl)-4-(chloromethyl)-5-methyl-1H-imidazole; hydrochloride (Intermediate 15)/1-Methyl-3-(4-piperidyl)benzimidazol-2-one (CAS 53786-10-0) |

Example 12

5-(4-Bromophenyl)-3-[1-[[4-methyl-2-[4-(trifluoromethyl)phenyl]-1H-imidazol-5-yl]methyl]-4-piperidyl]-1H-imidazol-2-one

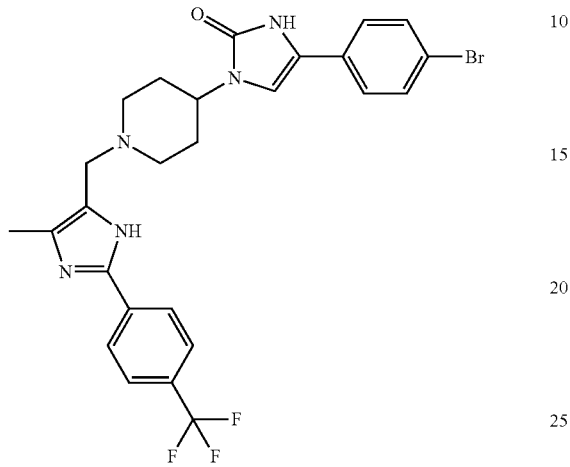

5-(4-Bromophenyl)-3-(4-piperidyl)-1H-imidazol-2-one; trifluoroacetic acid salt (intermediate 42) was dissolved in ethanol and diisopropylethyl amine (6 equivalents) was added at 0° C. Then [5-methyl-2-[4-(trifluoromethyl)phenyl]-1H-imidazol-4-yl]methyl methanesulfonate (intermediate 27) (1 equivalent) was added and the mixture was heated to reflux for 16 h. The solvent was removed in vacuo and the remaining residue was dissolved in EtOAc, washed with water and brine. After removal of the solvent, the remaining residue was purified by column chromatography over silica gel to obtain the title compound. MS (ESI): 559.9 (M+H)$^+$.

The following examples were prepared in analogy to example 12:

| Ex. | Name | Structure | MS (ESI) | Reagents |
|---|---|---|---|---|
| 13 | 1-[1-[[4-Methyl-2-[4-(trifluoromethyl)phenyl]-1H-imidazol-5-yl]methyl]-4-piperidyl]-5H-imidazo[4,5-c]pyridin-4-one | 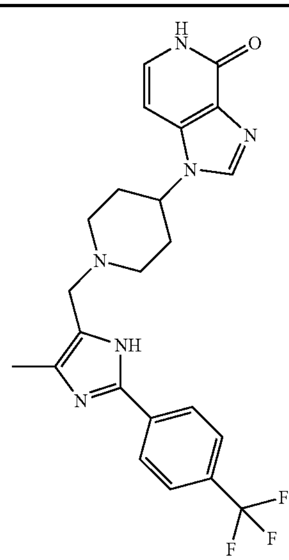 | 457.1 (M + H)$^+$ | [5-Methyl-2-[4-(trifluoromethyl)phenyl]-1H-imidazol-4-yl]methyl methanesulfonate (Intermediate 27)/1-(4-Piperidyl)-5H-imidazo[4,5-c]pyridin-4-one; hydrochloride (Intermediate 45) |

-continued

| Ex. | Name | Structure | MS (ESI) | Reagents |
|---|---|---|---|---|
| 14 | 1-[1-[[2-[4-(Trifluoromethyl)phenyl]-1H-imidazol-5-yl]methyl]-4-piperidyl]-5H-imidazo[4,5-c]pyridin-4-one | 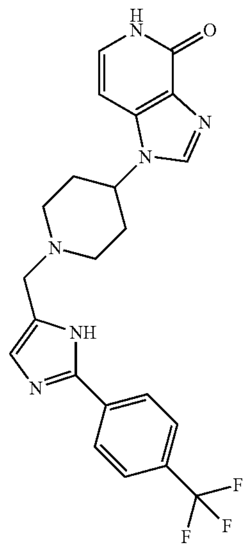 [SMILES: O=c1[nH]ccc2c1ncn2C1CCN(Cc2cnc(-c3ccc(C(F)(F)F)cc3)[nH]2)CC1] | 443.0 (M + H)+ | [2-[4-(Trifluoromethyl)phenyl]-1H-imidazol-4-yl]methyl methanesulfonate (Intermediate 26)/1-(4-Piperidyl)-5H-imidazo[4,5-c]pyridin-4-one; hydrochloride (Intermediate 45) |
| 15 | 5-(4-Bromophenyl)-2-[1-[[2-[4-(trifluoromethyl)phenyl]-1H-imidazol-5-yl]methyl]-4-piperidyl]-4H-1,2,4-triazol-3-one | 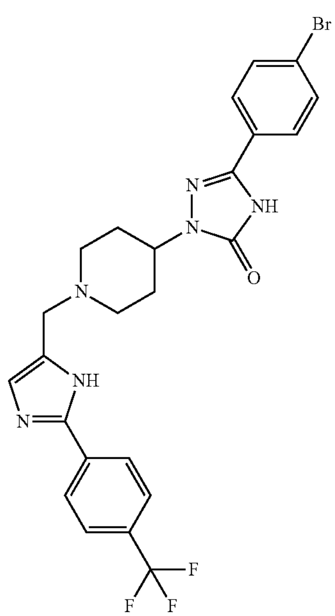 [SMILES: O=c1[nH]c(-c2ccc(Br)cc2)nn1C1CCN(Cc2cnc(-c3ccc(C(F)(F)F)cc3)[nH]2)CC1] | 546.3 (M + H)+ | [2-[4-(Trifluoromethyl)phenyl]-1H-imidazol-4-yl]methyl methanesulfonate (Intermediate 26)/5-(4-Bromophenyl)-3-(4-piperidyl)-1H-imidazol-2-one; trifluoroacetic acid salt (Intermediate 42) |

-continued

| Ex. | Name | Structure | MS (ESI) | Reagents |
|---|---|---|---|---|
| 16 | 5-(4-Bromophenyl)-2-[1-[[2-[4-(trifluoromethyl)phenyl]-1H-imidazol-5-yl]methyl]-4-piperidyl]-4H-1,2,4-triazol-3-one | 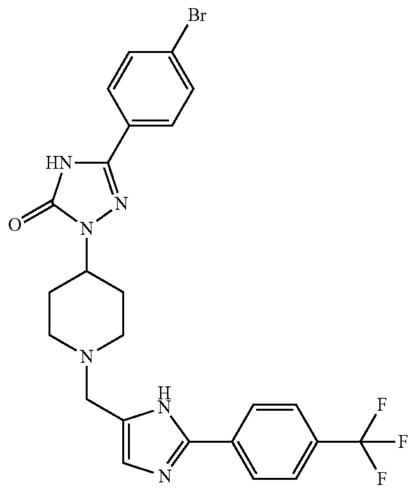 [SMILES: O=c1[nH]c(-c2ccc(Br)cc2)nn1C1CCN(Cc2cnc(-c3ccc(C(F)(F)F)cc3)[nH]2)CC1] | 547.2 (M + H)+ | [2-[4-(Trifluoromethyl)phenyl]-1H-imidazol-4-yl]methyl methanesulfonate (Intermediate 26)/5-(4-Bromophenyl)-2-(4-piperidyl)-4H-1,2,4-triazol-3-one; trifluoroacetic acid salt (Intermediate 43) |
| 17 | 6-Bromo-3-[1-[[2-[4-(trifluoromethyl)phenyl]-1H-imidazol-5-yl]methyl]-4-piperidyl]-1,4-dihydroquinazolin-2-one | 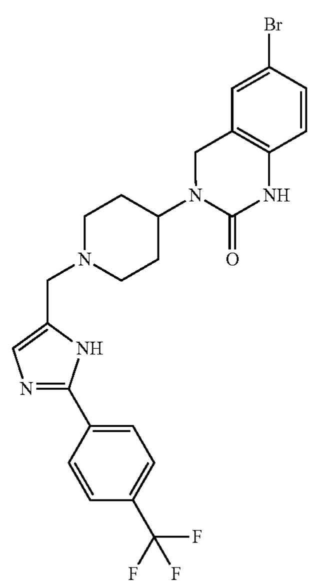 [SMILES: O=C1Nc2ccc(Br)cc2CN1C1CCN(Cc2cnc(-c3ccc(C(F)(F)F)cc3)[nH]2)CC1] | 534.2 (M + H)+ | [2-[4-(Trifluoromethyl)phenyl]-1H-imidazol-4-yl]methyl methanesulfonate (Intermediate 26)/6-Bromo-3-(4-piperidyl)-1,4-dihydroquinazolin-2-one; hydrochloride (Intermediate 44) |

Example 30

5-Chloro-3-(2-hydroxy-ethyl)-1-{1-[5-methyl-2-(4-trifluoromethyl-phenyl)-1H-imidazol-4-ylmethyl]-piperidin-4-yl}-1,3-dihydro-benzoimidazol-2-one

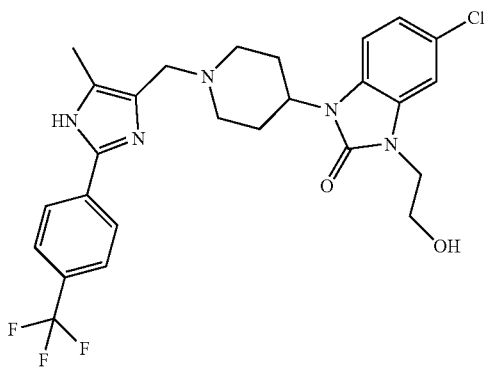 [SMILES: Cc1[nH]c(-c2ccc(C(F)(F)F)cc2)nc1CN1CCC(n2c(=O)n(CCO)c3cc(Cl)ccc32)CC1]

Acetic acid 2-(6-chloro-3-{1-[5-methyl-2-(4-trifluoromethyl-phenyl)-1H-imidazol-4-ylmethyl]-piperidin-4-yl}-2-oxo-2,3-dihydro-benzoimidazol-1-yl)-ethyl ester (example 29) (85 mg; 0.1476 mmol) was dissolved in MeOH (1 ml) and a solution of NaOH (12 mg; 0.295 mmol) in water (300 µl) was added. The yellow solution was stirred at RT for 1.5 h, then the MeOH was removed and water was added. The mixture was extracted with EtOAc and the combined extracts were washed with diluted NaOH solution and brine, dried with $Na_2SO_4$ and evaporated. The remaining crude material was purified by column chromatography (10 g silica gel; DCM/MeOH 100:0-90:10) to obtain the title compound as white solid (60 mg). MS (ESI): 534.2 $(M+H)^+$.

Example 34

(6-Chloro-3-{1-[5-methyl-2-(4-trifluoromethyl-phenyl)-1H-imidazol-4-ylmethyl]-piperidin-4-yl}-2-oxo-2,3-dihydro-benzoimidazol-1-yl)-acetic acid (6-Chloro-3-{1-[5-methyl-2-(4-trifluoromethyl-phenyl)-1H-imidazol-4-ylmethyl]-piperidin-4-yl}-2-oxo-2,3-dihydro-benzoimidazol-1-yl)-acetic acid methyl ester (example 33) (85 mg; 0.1512 mmol) was dissolved in MeOH (1 ml) and a solution of NaOH (12 mg; 0.302 mmol) in water (300 ul) was added. The yellow solution was stirred at RT for 1.5 h and the MeOH was removed. To the remaining residue water and 0.1N HCl (1512 µl) were added. The pH was carefully adjusted to 7 by addition of 0.1N HCl. The precipitate that formed was filtered off, washed with a small amount of water and a small amount of diethyl ether and dried to obtain the title compound as light brown solid (58 mg). MS (ESI): 548.3 $(M+H)^+$.

Example 52

3-{1-[3-Methyl-1-(4-trifluoromethyl-phenyl)-1H-pyrazol-4-ylmethyl]-piperidin-4-yl}-3,4-dihydro-1H-quinazolin-2-one

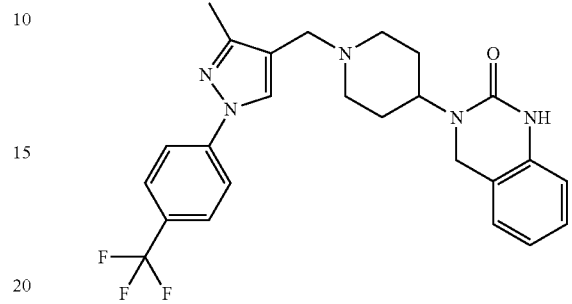

3-Methyl-1-[4-(trifluoromethyl)phenyl]pyrazole-4-carbaldehyde (Intermediate 25) (75 mg) and 3-(4-piperidyl)-1,4-dihydroquinazolin-2-one (CAS 79098-75-2) (68 mg) were dissolved in DCM (4 ml). Then sodium triacetoxyborohydride (94 mg) and AcOH (51 µl) were added and the mixture was stirred for 20 h. Saturated $NaHCO_3$ solution was added and the mixture was extracted with EtOAc. The combined extracts were dried with $Na_2SO_4$ and evaporated. The remaining solid was triturated with EtOAc to obtain the title compound as white solid (103 mg). MS (ESI): 470.3 $(M+H)^+$.

INTERMEDIATES

Intermediate 1

4-(Chloromethyl)-5-methyl-2-[4-(trifluoromethyl)phenyl]-1H-imidazole; hydrochloride

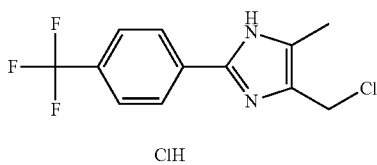 [SMILES: Cc1[nH]c(-c2ccc(C(F)(F)F)cc2)nc1CCl ; Cl]

Step 1:

To a refluxing solution of 4-(trifluoromethyl)-benzamidine; hydrochloride dihydrate (CAS 175278-62-3) (5 g; 19.18 mmol) in isopropanol (70 ml) was added 2,3-butanedione (2.10 ml; 24.0 mmol) and the reaction mixture was heated to reflux for 23 h. The reaction mixture was concentrated to dryness, water (20 ml) and 4N HCl (40 ml) were added and the brown suspension was heated to reflux for 3 h. The mixture was again concentrated to dryness and residual water was removed by co-evaporation with toluene (six times). The remaining [5-methyl-2-[4-(trifluoromethyl)phenyl]-1H-imidazol-4-yl]methanol; hydrochloride (light brown solid, 5.93 g) was used in the next step without further purification.

Step 2:

[5-Methyl-2-[4-(trifluoromethyl)phenyl]-1H-imidazol-4-yl]methanol; hydrochloride obtained in step 1 (930 mg; 3.18 mmol) was suspended in toluene (10 ml). A solution of SOCl$_2$ (2 ml; 28.6 mmol) in toluene (2 ml) was added dropwise at RT. After the addition was complete, the reaction mixture was heated to 65° C. for 5 min, then cooled to RT and stirred at RT for 2 h. Diethyl ether (~50 ml) was added and the light brown precipitate was filtered off, washed with diethyl ether and dried. The title compound (891 mg, off-white solid) was used without further purification. MS (ESI): 239.1 (M+H—HCl)$^+$.

The following intermediates were prepared in analogy to intermediate 1:

| Int. | Name | Structure | MS (ESI) | Starting reagent |
|---|---|---|---|---|
| 2 | 4-(Chloromethyl)-2-(4-chlorophenyl)-5-methyl-1H-imidazole; hydrochloride | 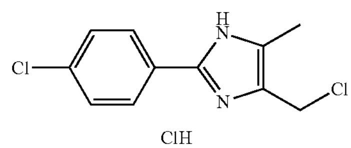 | | 4-Chlorobenzamidine (CAS 19563-04-3) |
| 3 | 4-(Chloromethyl)-5-methyl-2-(p-tolyl)-1H-imidazole; hydrochloride | 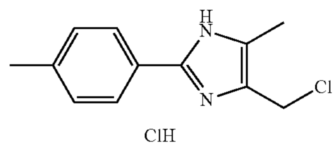 | | 4-Methyl-benzamidine (CAS 18465-11-7) |
| 4 | 4-(Chloromethyl)-2-(3-fluoro-4-methyl-phenyl)-5-methyl-1H-imidazole; hydrochloride | 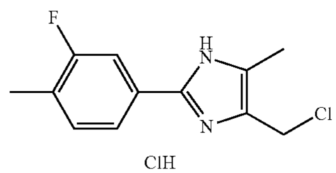 | | 3-Fluoro-4-methyl-benzamidine; hydrochloride (CAS 175277-88-0) |
| 5 | 4-(Chloromethyl)-2-(3-chloro-4-methyl-phenyl)-5-methyl-1H-imidazole; hydrochloride | 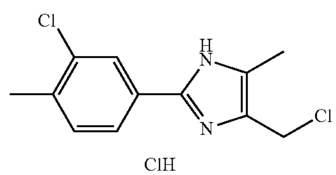 [SMILES: Cc1ccc(-c2nc(CCl)c(C)[nH]2)cc1F ; Cl] | | 3-Chloro-4-methyl-benzamidine (CAS 170735-25-8) |
| 6 | 4-(Chloromethyl)-2-[3-chloro-4-(trifluoromethyl)phenyl]-5-methyl-1H-imidazole; hydrochloride | 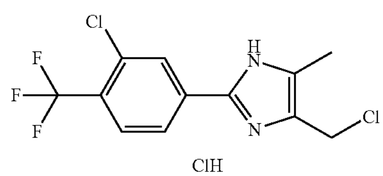 | 273.1 (M + H − HCl)$^+$ | 3-Chloro-4-(trifluoromethyl)benzamidine; hydrochloride (Intermediate 6a) |
| 7 | 4-(Chloromethyl)-2-(3,4-dichlorophenyl)-5-methyl-1H-imidazole; hydrochloride | 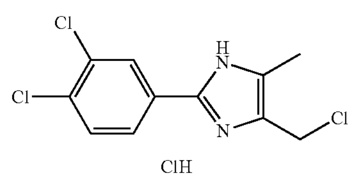 | 238.9 (M + H − HCl)$^+$ | 3,4-Dichlorobenzamidine (CAS 25412-64-0) |
| 8 | 4-(Chloromethyl)-2-[3-fluoro-4-(trifluoromethyl)phenyl]-5-methyl-1H-imidazole; hydrochloride | 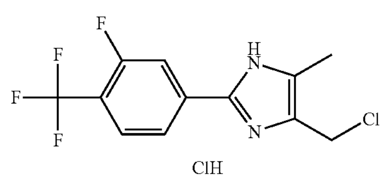 | 257.0 (M + H − HCl)$^+$ | 3-Fluoro-4-(trifluoromethyl)benzamidine; hydrochloride (CAS 910053-57-5) |
| 9 | 2-(4-Chloro-3-fluoro-phenyl)-4-(chloromethyl)-5-methyl-1H-imidazole; hydrochloride | 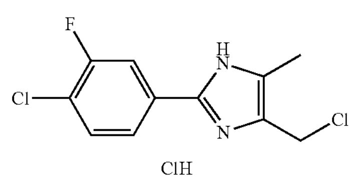 | 223.1 (M + H − HCl)$^+$ | 4-Chloro-3-fluoro-benzamidine; hydrochloride (Intermediate 9a) |

-continued

| Int. | Name | Structure | MS (ESI) | Starting reagent |
|---|---|---|---|---|
| 10 | 4-(Chloromethyl)-2-(2,4-dichlorophenyl)-5-methyl-1H-imidazole; hydrochloride | 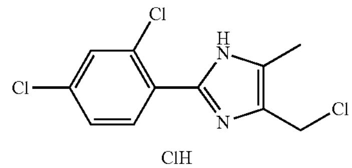 | 238.9 (M + H − HCl)+ | 2,4-Dichlorobenzamidine; hydrochloride (CAS 154505-50-7) |
| 11 | 4-(Chloromethyl)-2-[2-chloro-4-(trifluoromethyl)phenyl]-5-methyl-1H-imidazole; hydrochloride | 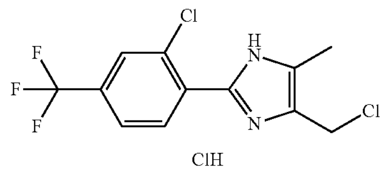 | 273.1 (M + H − HCl)+ | 2-Chloro-4-(trifluoromethyl)benzamidine; hydrochloride (Intermediate 11a) |
| 12 | 4-(Chloromethyl)-5-methyl-2-(4-methylsulfonylphenyl)-1H-imidazole; hydrochloride | 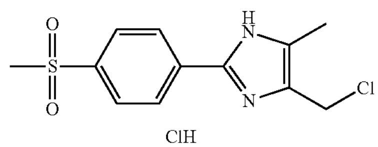 [SMILES: Cc1[nH]c(-c2ccc(S(C)(=O)=O)cc2)nc1CCl ; Cl] | 1H-NMR | 4-Methylsulfonylbenzamidine (CAS 17574-50-4) |
| 13 | 4-(Chloromethyl)-5-methyl-2-[4-(trifluoromethylsulfonyl)phenyl]-1H-imidazole; hydrochloride | 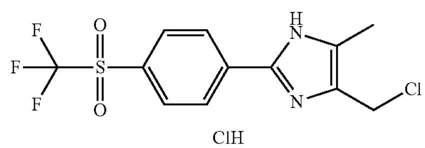 [SMILES: Cc1[nH]c(-c2ccc(S(=O)(=O)C(F)(F)F)cc2)nc1CCl ; Cl] | 1H-NMR | 4-(Trifluoromethylsulfonyl)benzamidine; hydrochloride (Intermediate 13a) |
| 14 | 4-(Chloromethyl)-2-(4-isobutylsulfonylphenyl)-5-methyl-1H-imidazole; hydrochloride | 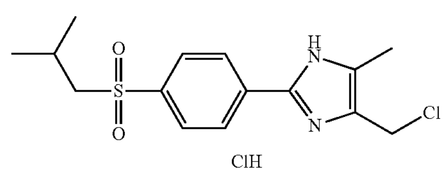 | 291.1 (M + H − HCl)+ | 4-Isobutylsulfonylbenzamidine; hydrochloride (Intermediate 14a) |
| 15 | 2-(4-Benzylsulfonylphenyl)-4-(chloromethyl)-5-methyl-1H-imidazole; hydrochloride | 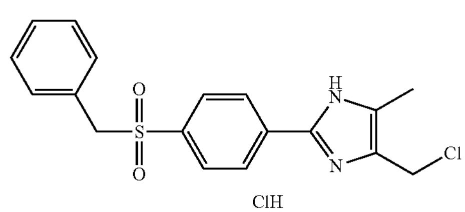 [SMILES: Cc1[nH]c(-c2ccc(S(=O)(=O)Cc3ccccc3)cc2)nc1CCl ; Cl] | 1H-NMR | 4-Benzylsulfonylbenzamidine; hydrochloride (Intermediate 15a) |
| 16 | 4-(Chloromethyl)-5-phenyl-2-[4-(trifluoromethyl)phenyl]-1H-imidazole; hydrochloride | 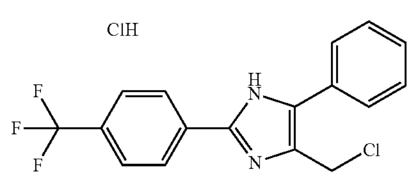 [SMILES: FC(F)(F)c1ccc(-c2nc(CCl)c(-c3ccccc3)[nH]2)cc1 ; Cl] | 1H-NMR | 4-(Trifluoromethyl)benzamidine; hydrochloride dihydrate (CAS 175278-62-3) and 1-phenylpropane-1,2-dione |

Intermediate 12: $^1$H-NMR (DMSO-d$_6$, 300 MHz): δ 2.38 (s, 3H), 3.30 (s, 3H), 4.91 (s, 2H), 8.14 (d, J=8.7 Hz, 2H), 8.24 (d, J=8.7 Hz, 2H).

Intermediate 13: $^1$H-NMR (DMSO-d$_6$, 300 MHz): δ 2.36 (s, 3H), 4.87 (s, 2H), 8.31 (d, J=8.7 Hz, 2H), 8.37 (d, J=8.7 Hz, 2H).

Intermediate 15: $^1$H-NMR (DMSO-d$_6$, 300 MHz): δ 2.40 (s, 3H), 4.79 (s, 2H), 4.94 (s, 2H), 7.17 (m, 2H), 7.30 (m, 3H), 7.93 (d, J=8.4 Hz, 2H), 8.29 (d, J=8.4 Hz, 2H).

Intermediate 16: $^1$H-NMR (DMSO-d$_6$, 300 MHz): δ 4.94 (s, 2H), 7.45 (t, J=7.2 Hz, 1H), 7.56 (t, J=7.2 Hz, 2H), 7.76 (d, J=7.2 Hz, 2H), 7.92 (d, J=8.3 Hz, 2H), 8.30 (d, J=8.3 Hz, 2H).

Intermediate 6a

3-Chloro-4-(trifluoromethyl)benzamidine; hydrochloride

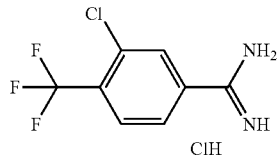

A solution of 3-chloro-4-(trifluoromethyl)-benzonitrile (2 g; 98%; 9.53 mmol) in CHCl$_3$ (16 ml) and MeOH (4 ml) was cooled to 0° C. Then HCl-gas was bubbled through this solution for 45 min. The flask was closed and stored overnight in the fridge. Then argon was bubbled through to remove excess of HCl-gas and all solvents were evaporated. NH$_3$ (2M solution in MeOH; 24 ml; 47.7 mmol) was added and the solution was stirred at RT for 2 h. The reaction mixture was concentrated to dryness. Then again NH$_3$ (2M solution in MeOH; 24 ml; 47.7 mmol) was added and the reaction mixture was stirred at RT overnight. The solvents were removed and the remaining white foamy solid (2.56 g) was used without purification for the next step. MS (ESI): 223.1 (M+H)$^+$.

The following intermediates were prepared in analogy to intermediate 6a:

| Int. | Name | Structure | MS (ESI) | Starting reagent |
|---|---|---|---|---|
| 9a | 4-Chloro-3-fluoro-benzamidine; hydrochloride | 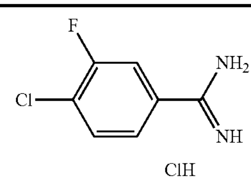 | 173.1 (M + H)$^+$ | 4-Chloro-3-fluoro-benzonitrile (CAS 110888-15-8) |
| 11a | 2-Chloro-4-(trifluoromethyl)benzamidine; hydrochloride | 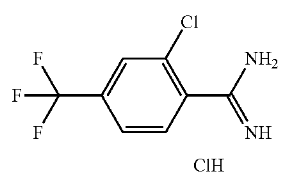 [SMILES: N=C(N)c1ccc(C(F)(F)F)cc1Cl ; Cl] | 223.1 (M + H)$^+$ | 2-Chloro-4-(trifluoromethyl)benzonitrile (CAS 1813-33-8) |

Intermediate 13a 4-(Trifluoromethylsulfonyl)benzamidine; hydrochloride

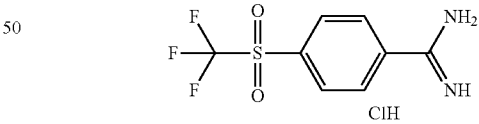

To a suspension of NH$_4$Cl (910 mg, 17 mmol) in toluene (20 ml) was added trimethylaluminum (2M solution in heptane, 8.5 ml, 17 mmol) dropwise at 0° C. Then a solution of 4-(trifluoromethylsulfonyl)benzonitrile (CAS 312-21-0) (800 mg, 3.4 mmol) in toluene (10 ml) was added and the reaction mixture was heated to reflux overnight. The reaction mixture was cooled to RT and was added to a suspension of silica gel (40 g) in DCM (200 ml). This mixture was stirred at RT for 1 h, filtered and the filter cake was washed with DCM/MeOH 4:1 (350 ml). The tile compound was obtained by evaporation of the filtrate as white solid (1.08 g). MS (ESI): 253.3 (M+H)$^+$.

The following intermediates were prepared in analogy to intermediate 13a:

| Int. | Name | Structure | MS (ESI) | Starting reagent |
|---|---|---|---|---|
| 14a | 4-Isobutylsulfonylbenzamidine; hydrochloride | 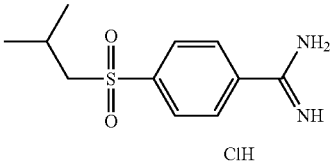 [SMILES: CC(C)CS(=O)(=O)c1ccc(C(=N)N)cc1 ; Cl] | 241.2 (M + H)+ | 4-Isobutylsulfonylbenzonitrile (Intermediate 14b) |
| 15a | 4-Benzylsulfonylbenzamidine; hydrochloride | 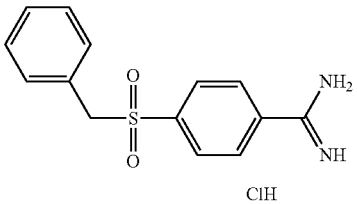 [SMILES: N=C(N)c1ccc(S(=O)(=O)Cc2ccccc2)cc1 ; Cl] | 275.1 (M + H)+ | 4-Benzylsulfonylbenzonitrile (Intermediate 15b) |

Intermediate 14b

4-Isobutylsulfonylbenzonitrile

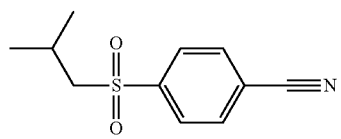

Step 1:

To a solution of 2-methylpropane-1-thiol (1.68 ml, 15.4 mmol) in DMF (20 ml) was added sodium hydride (55% dispersion in oil, 404 mg, 16.8 mmol) portionwise at 0° C. The reaction mixture was stirred at RT for 1 h. Then a solution of 4-fluorobenzonitrile (1.7 g, 14.0 mmol) in DMF (5 ml) was added dropwise. After 4 h 1N NaOH solution was added and the mixture was extracted with diethyl ether. The combined organic extracts were washed three times with brine, dried with $Na_2SO_4$ and evaporated. The remaining residue was purified by column chromatography (50 g silica gel; heptane/DCM 1:1) to obtain 4-isobutylsulfonylbenzonitrile as colorless oil (1.83 g). MS (ESI): 209.1 $(M+NH_4)^+$.

Step 2:

To a solution of 4-isobutylsulfonylbenzonitrile (1.83 g, 9.6 mmol) in MeOH (35 ml) was added a solution of Oxone (10 g) in water (35 ml) dropwise at 0° C. The reaction mixture was stirred at RT for 4 h and the MeOH was removed under vacuum. Water was added and the mixture was extracted with EtOAc. The combined extracts were washed with brine, dried with $Na_2SO_4$ and evaporated to obtain the title compound as white solid (2.23 g). MS (ESI): 282.3 (M+OAc)−.

Intermediate 15b

4-Benzylsulfonylbenzonitrile

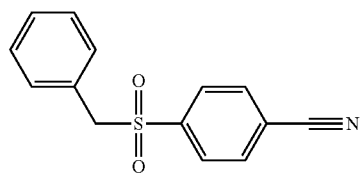 [SMILES: N#Cc1ccc(S(=O)(=O)Cc2ccccc2)cc1]

The title compound was prepared in analogy to intermediate 14b using phenylmethanethiol instead of 2-methylpropane-1-thiol and was obtained as white solid. MS (ESI): 256.3 (M−H)−.

Intermediate 17

4-(Chloromethyl)-5-(2-methoxyethyl)-2-[4-(trifluoromethyl)phenyl]-1H-imidazole; hydrochloride

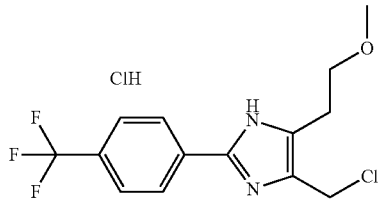 [SMILES: COCCc1[nH]c(-c2ccc(C(F)(F)F)cc2)nc1CCl ; Cl]

Step 1:

To a solution of methyl 5-methoxy-3-oxo-pentanoate (CAS 62462-05-9) (2.0 g, 12 mmol) in AcOH (3.0 ml) was added a solution of $NaNO_2$ (948 mg, 14 mmol) in water (3.5 ml) dropwise at 0° C. The reaction mixture was stirred at RT for 1 h before additional water (10 ml) was added. After another 2 h, the reaction mixture was extracted with EtOAc and the combined extracts were dried with $Na_2SO_4$ and evaporated. Methyl 2-hydroxyimino-5-methoxy-3-oxo-pentanoate (2.23 g) remained as a light brown oil and was used for the next reaction step without purification. MS (ESI): 188.1 (M−H)−.

Step 2:

A solution of [4-(trifluoromethyl)phenyl]methanamine (2.24 g, 12.8 mmol) and methyl 2-hydroxyimino-5-methoxy-3-oxo-pentanoate (2.2 g, 11.6 mmol) in acetonitrile (30 ml) was heated to reflux for 5 h. The reaction mixture was then concentrated and the remaining residue was purified by column chromatography (first with 100 g silica gel; heptane/EtOAc 4:1 to 2:1 and a second time with 50 g silica gel; DCM/EtOAc 2:1). Methyl 5-(2-methoxyethyl)-2-[4-(trifluoromethyl)phenyl]-1H-imidazole-4-carboxylate was obtained as light yellow solid (935 mg). MS (ESI): 327.4 (M−H)−.

Step 3:

To a solution of methyl 5-(2-methoxyethyl)-2-[4-(trifluoromethyl)phenyl]-1H-imidazole-4-carboxylate (100 mg, 0.3 mmol) in THF (4 ml) was added lithium aluminum hydride (28 mg, 0.73 mmol) and the mixture was stirred at RT for 2 h. Saturated NH₄Cl solution was added and the mixture was extracted with EtOAc. The combined organic layers were dried with Na₂SO₄ and concentrated. The remaining solid was triturated with DCM to obtain [5-(2-methoxyethyl)-2-[4-(trifluoromethyl)phenyl]-1H-imidazol-4-yl]methanol (70 mg) as white solid. MS (ESI): 299.4 (M−H)⁻.

Step 4:

To a suspension of [5-(2-methoxyethyl)-2-[4-(trifluoromethyl)phenyl]-1H-imidazol-4-yl]methanol (70 mg, 0.23 mmol) in toluene (3.0 ml) was added thionyl chloride (85 µl) and the mixture was stirred at RT. After completion of the reaction, diethyl ether was added and the precipitate was filtered and washed with diethyl ether. The title compound was obtained as white solid (78 mg). ¹H-NMR (DMSO-d₆, 300 MHz): δ 2.98 (t, J=6.6 Hz, 2H), 3.27 (s, 3H), 3.60 (t, J=6.6 Hz, 2H), 4.88 (s, 2H), 7.95 (d, J=8.1 Hz, 2H), 8.18 (d, J=8.1 Hz, 2H).

The following intermediates were prepared in analogy to intermediate 17:

mixture was then cooled to 0° C. and the precipitate that formed was filtered off, washed with acetonitrile and dried to obtain ethyl 5-methyl-2-[4-(trifluoromethyl)phenyl]-1H-imidazole-4-carboxylate as white solid (3.45 g). MS (ESI): 299.0 (M+H)⁺.

Step 2:

To a suspension of ethyl 5-methyl-2-[4-(trifluoromethyl)phenyl]-1H-imidazole-4-carboxylate (1.0 g, 3.35 mmol) and potassium tert-butoxide (414 mg, 3.69 mmol) in acetonitrile (10 ml) was added methyl iodide (230 ml, 3.69 mmol) and the reaction mixture was stirred at RT overnight. The reaction mixture was concentrated and DCM and saturated NaHCO₃ solution were added. After phase separation, the aqueous was extracted with DCM and the combined organic layers were dried with Na₂SO₄ and evaporated. The remaining residue was purified by column chromatography (silica gel; heptane/EtOAc 5:1 to 3:1) to obtain ethyl 3,5-dimethyl-2-[4-(trifluoromethyl)phenyl]imidazole-4-carboxylate (181

| Int. | Name | Structure | | Starting reagent |
|---|---|---|---|---|
| 18 | 4-(Chloromethyl)-5-propyl-2-[4-(trifluoromethyl)phenyl]-1H-imidazole; hydrochloride | 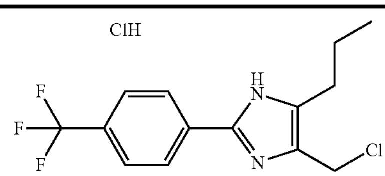 | MS (ESI): 267.5 (M + H − HCl)⁺ | Ethyl 3-oxohexanoate (CAS 3249-68-1) |
| 19 | (5-Benzyl-4-(chloromethyl)-2-[4-trifluoromethyl)phenyl]-1H-imidazole; hydrochloride | 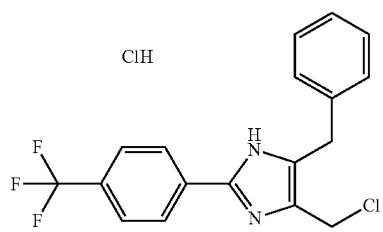 [SMILES: FC(F)(F)c1ccc(-c2nc(CCl)c(Cc3ccccc3)[nH]2)cc1 ; Cl] | ¹H-NMR | Methyl 3-oxo-4-phenyl-butanoate (CAS 37779-49-0) |

Intermediate 19: ¹H-NMR (DMSO-d₆, 300 MHz): δ 4.29 (s, 2H), 4.98 (s, 2H), 7.20-7.45 (m, 5H), 8.00 (d, J=9 Hz, 2H), 8.31 (d, J=9 Hz, 2H).

Intermediate 20

4-(Chloromethyl)-1,5-dimethyl-2-[4-(trifluoromethyl)phenyl]imidazole; hydrochloride

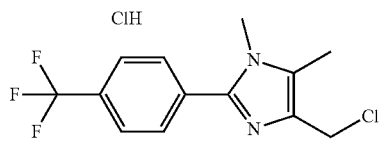 [SMILES: Cl ; Cc1c(CCl)nc(-c2ccc(C(F)(F)F)cc2)n1C]

Step 1:

A solution of ethyl 2-hydroxyimino-3-oxo-butanoate (CAS 66508-93-8) (3.0 g, 18.9 mmol) and [4-(trifluoromethyl)phenyl]methanamine (3.63 g, 20.7 mmol) in acetonitrile (40 ml) was heated to reflux overnight. The reaction mg, white solid) and the desired ethyl 1,5-dimethyl-2-[4-(trifluoromethyl)phenyl]imidazole-4-carboxylate (424 mg) as white solid. MS (ESI): 313.0 (M+H)⁺.

Step 3:

To a solution of ethyl 1,5-dimethyl-2-[4-(trifluoromethyl)phenyl]imidazole-4-carboxylate (175 mg, 0.56 mmol) in THF (3 ml) was added lithium aluminum hydride (28 mg, 0.73 mmol) and the mixture was stirred at RT for 2 h. Saturated NH₄Cl solution was added and the mixture was extracted with EtOAc. The combined organic layers were dried with Na₂SO₄ and concentrated. The remaining solid was triturated with DCM to obtain [1,5-dimethyl-2-[4-(trifluoromethyl)phenyl]imidazol-4-yl]methanol (96 mg) as white solid. MS (ESI): 271.3 (M+H)⁺.

Step 4:

To a suspension of [1,5-dimethyl-2-[4-(trifluoromethyl)phenyl]imidazol-4-yl]methanol (80 mg, 0.3 mmol) in toluene (3.0 ml) was added thionyl chloride (108 µl) and the mixture was stirred at RT. After completion of the reaction, diethyl ether was added and the precipitate was filtered and washed with diethyl ether. The title compound was obtained as white solid (96 mg). NMR (CDCl₃, 300 MHz): δ 2.46 (s, 3H), 3.81 (s, 3H), 4.92 (s, 2H), 7.86 (d, J=8.3 Hz, 2H), 7.97 (d, J=8.3 Hz, 2H).

Intermediate 21

4-(Chloromethyl)-1-(2-methoxyethyl)-5-methyl-2-[4-(trifluoromethyl)phenyl]imidazole; hydrochloride

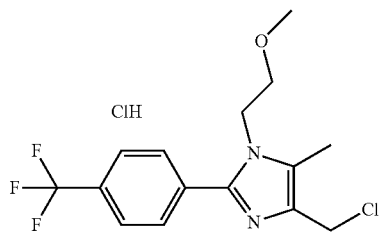 [SMILES: COCCn1c(-c2ccc(C(F)(F)F)cc2)nc(CCl)c1C ; Cl]

Step 1:

To a suspension of sodium hydride (55% dispersion in oil, 64 mg, 1.3 mmol) in DMF (4 ml) was added a solution of ethyl 5-methyl-2-[4-(trifluoromethyl)phenyl]-1H-imidazole-4-carboxylate (331 mg, 1.1 mmol) in DMF (1 ml) and the reaction mixture was stirred at RT for 1.5 h. Then 2-bromoethyl methyl ether (110 µl) was added and the reaction mixture was heated to 100° C. overnight. The mixture was cooled to RT and again sodium hydride (55% dispersion in oil, 6 mg) and 2-bromoethyl methyl ether (10 µl) were added. The reaction mixture was again heated to 100° C. overnight. Then water was added and the mixture was extracted with EtOAc. The combined extracts were dried with $Na_2SO_4$ and evaporated. The remaining residue was purified by column chromatography (50 g silica gel; heptane/EtOAc 4:1 to 2:1) to obtain ethyl 3-(2-methoxyethyl)-5-methyl-2-[4-(trifluoromethyl)phenyl]imidazole-4-carboxylate (122 mg, light yellow oil) and the desired ethyl 1-(2-methoxyethyl)-5-methyl-2-[4-(trifluoromethyl)phenyl]imidazole-4-carboxylate (123 mg) as light yellow oil. MS (ESI): 357.4 $(M+H)^+$.

Step 2:

To a suspension of lithium aluminum hydride (14 mg, 0.4 mmol) in THF (4 ml) was added a solution of ethyl 1-(2-methoxyethyl)-5-methyl-2-[4-(trifluoromethyl)phenyl]imidazole-4-carboxylate (115 mg, 0.3 mmol) in THF (4 ml) dropwise at 0° C. The reaction mixture was stirred at RT for 2 h. A mixture of $Na_2SO_4$ (1 g), silica gel (1 g) and 20 drops of water was added portionwise and stirring was continued for 10 min. The mixture was filtered and the filtrate was evaporated to obtain [1-(2-methoxyethyl)-5-methyl-2-[4-(trifluoromethyl)phenyl]imidazol-4-yl]methanol (89 mg) as light yellow solid. MS (ESI): 315.0 $(M+H)^+$.

Step 3:

To a solution of [1-(2-methoxyethyl)-5-methyl-2-[4-(trifluoromethyl)phenyl]imidazol-4-yl]methanol (85 mg, 0.3 mmol) in toluene (5.0 ml) was added thionyl chloride (100 µl) and the mixture was stirred at RT. After completion of the reaction all volatiles were removed under vacuum to obtain the title compound as orange solid (90 mg). NMR ($CDCl_3$, 300 MHz): δ 2.61 (s, 3H), 3.31 (s, 3H), 3.67 (t, J=5.1 Hz, 2H), 4.43 (t, J=5.1 Hz, 2H), 4.78 (s, 2H), 7.87 (d, J=8.4 Hz, 2H), 8.02 (d, J=8.4 Hz, 2H).

Intermediate 22

5-(Chloromethyl)-1-methyl-3-[4-(trifluoromethyl)phenyl]-1,2,4-triazole

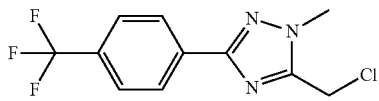

Step 1:

To a solution of 2-benzyloxyacetohydrazide (CAS 39256-35-4) (2.84 g; 15.8 mmol) in MeOH (40 ml) were added 4-(trifluormethyl)-benzonitrile (CAS 455-18-5) (5.39 g; 31.5 mmol) and potassium tert-butoxide (1.06 g; 9.46 mmol) and the mixture was heated to reflux for 22 h. The yellow solution was cooled to RT and water was added. MeOH was removed under vacuum and the remaining aqueous layer was extracted with EtOAc. The combined extracts were dried with $Na_2SO_4$ and evaporated. The remaining residue was purified by column chromatography (50 g silica gel; heptane/EtOAc 90:10-75:25) to obtain 5-(benzyloxymethyl)-3-[4-(trifluoromethyl)phenyl]-1H-1,2,4-triazole as with solid (3.93 g). MS (ESI): 334.2 $(M+H)^+$.

Step 2:

To a solution of 5-(benzyloxymethyl)-3-[4-(trifluoromethyl)phenyl]-1H-1,2,4-triazole (1 g; 3 mmol) in THF (15 ml) were added powdered KOH (313 mg; 86%; 4.8 mmol), methyl iodide (280 µl; 4.5 mmol) and $Bu_4NBr$ (97 mg, 0.3 mmol) and the suspension was stirred overnight at RT. Then water was added and the mixture was extracted with EtOAc. The organic layers were combined, dried with $Na_2SO_4$ and evaporated. The remaining residue was purified by column chromatography (50 g silica gel; heptane/EtOAc 90:10-80:20) to obtain 5-(benzyloxymethyl)-1-methyl-3-[4-(trifluoromethyl)phenyl]-1,2,4-triazole (849 mg, light yellow solid, MS (ESI): 348.2 $(M+H)^+$) and 3-(benzyloxymethyl)-1-methyl-5-[4-(trifluoromethyl)phenyl]-1,2,4-triazole (141 mg, light yellow oil, MS (ESI): 348.2 $(M+H)^+$).

Step 3:

A suspension of 5-(benzyloxymethyl)-1-methyl-3-[4-(trifluoromethyl)phenyl]-1,2,4-triazole (830 mg; 2.39 mmol), ammonium formate (1.55 g; 23.9 mmol) and palladium (10% on carbon, 80 mg) in EtOH (12 ml) was heated to reflux for 20 h. Ammonium formate (775 mg; 97%; 11.9 mmol) was added and the black suspension was heated to reflux for additional 4 h. Again ammonium formate (775 mg) was added and the mixture was heated to reflux overnight. The reaction mixture was cooled to RT, filtered through celite. The filter cake was washed with EtOH and the filtrate was evaporated. The remaining residue was purified by column chromatography (20 g silica gel; heptane/EtOAc 70:30-30:70) to obtain [2-methyl-5-[4-(trifluoromethyl)phenyl]-1,2,4-triazol-3-yl]methanol (488 mg) as white solid. MS (ESI): 258.1 $(M+H)^+$.

Step 4:

A solution of thionyl chloride (0.62 ml; 8.54 mmol) in toluene (1 ml) was added to a suspension of [2-methyl-5-[4-(trifluoromethyl)phenyl]-1,2,4-triazol-3-yl]methanol (244 mg; 0.949 mmol) in toluene (4 ml) at RT. After the addition was complete, the mixture was heated to 65° C. for 5 min and then cooled to RT and stirred for 2.5 h at this temperature. Then diethyl ether was added and the precipitate was filtered off, washed with diethyl ether and dried to obtain the title compound (269 mg) as white solid. MS (ESI): 276.3 (M+H)⁺. ¹H-NMR (DMSO-d₆, 300 MHz): δ 3.99 (s, 3H), 5.06 (s, 2H), 7.84 (d, J=8.0 Hz, 2H), 8.18 (d, J=8.0 Hz, 2H).

Intermediate 23

3-(Chloromethyl)-1-methyl-5-[4-(trifluoromethyl)phenyl]-1,2,4-triazole

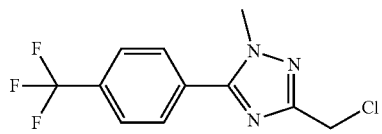

The title compound was prepared in analogy to intermediate 22 from 3-(benzyloxymethyl)-1-methyl-5-[4-(trifluoromethyl)phenyl]-1,2,4-triazole and was obtained as brown solid. ¹H-NMR (DMSO-d₆, 300 MHz): δ 4.00 (s, 3H), 4.77 (s, 2H), 7.94 (d, J=8.1 Hz, 2H), 8.04 (d, J=8.1 Hz, 2H).

Intermediate 24

3-(Chloromethyl)-4-methyl-1-[4-(trifluoromethyl)phenyl]pyrazole

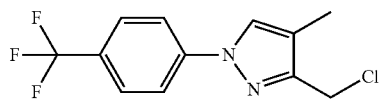

Step 1:
Ethyl-2-chloroacetoacetate (CAS 609-15-4) (1.82 ml; 95%; 12.41 mmol) was added at RT to a solution of sodium acetate trihydrate (1.69 g; 12.41 mmol) in EtOH (70 ml) and water (3.5 ml). The mixture was stirred for 20 min at RT and then cooled to 0° C. In a second flask, a solution of NaNO₂ (856 mg; 12.41 mmol) in water (12 ml) was added dropwise to a white suspension of 4-aminobenzotrifluoride (2.0 g; 12.41 mmol) in 6N HCl (19.5 ml) at 0° C. This reaction mixture was stirred at 0° C. until all solids dissolved. This solution was then transferred dropwise to the first solution. During the addition a solid precipitated. After the addition was completed, the yellow reaction mixture was stirred at 0° C. for 1 h, then concentrated to ~½ volume and stored overnight at −24° C. The precipitated solid was filtered off, washed with cold water and dried. The residue was triturated with toluene to obtain ethyl 2-chloro-2-[[4-(trifluoromethyl)phenyl]hydrazono]acetate (3.294 g) as light brown solid. MS (ESI): 293.4 (M−H)⁻.

Step 2:
Propionaldehyde (2.0 ml; 96%; 26.4 mmol) was added during 25 min to a suspension of K₂CO₃ (256 mg; 1.851 mmol) in morpholine (5 ml) at 25° C. The mixture was then stirred at 25-30° C. for 2.5 h. After concentration of the reaction mixture it was filtered and the filtrate was distilled under vacuum to obtain 4-[prop-1-enyl]morpholine (2.15 g, colorless oil) containing ~20% morpholine. This material was used in the next reaction step without further purification.

Step 3:
To a stirred solution of 4-[prop-1-enyl]morpholine (product from step 2, 270 mg; 80%; 1.967 mmol) in dry chloroform (3 ml, ethanol free) was added triethylamine (235 µl; 1.967 mmol) followed by a suspension of ethyl 2-chloro-2-[[4-(trifluoromethyl)phenyl]hydrazono]acetate (product from step 1, 500 mg; 1.967 mmol) in dry chloroform (3 ml, ethanol free). After the addition was completed, the yellow solution was stirred at 40° C. for 1 h, then at RT overnight. Water was added and the pH adjusted to 5 by addition of 0.1N HCl. This mixture was extracted with chloroform and the combined organic layers were washed with saturated NaHCO₃ solution and water, dried with Na₂SO₄ and evaporated. The remaining residue was dissolved in dioxane (6 ml) and 2N HCl (1.5 ml) was added. The solution was heated to reflux for 1 h and then concentrated to dryness. The remaining residue was dissolved in chloroform and this solution was washed with water. The organic layer was dried with Na₂SO₄ and evaporated. The remaining material was purified by column chromatography (20 g silica gel; heptane/EtOAc 95:5-90:10) to obtain ethyl 4-methyl-1-[4-(trifluoromethyl)phenyl]pyrazole-3-carboxylate (106 mg) as light brown oil that solidified after standing.

Step 4:
A solution of ethyl 4-methyl-1-[4-(trifluoromethyl)phenyl]pyrazole-3-carboxylate (100 mg; 0.335 mmol) in THF (4 ml) was added dropwise to a cooled suspension of lithium aluminum hydride (15 mg; 0.396 mmol) in THF (2 ml). The resulting suspension was stirred at RT for 2 h. A mixture of Na₂SO₄ (0.5 g), silica gel (0.3 g) and 8 drops of water was added portionwise and stirring was continued for 10 min. The solids were filtered off and washed with THF and the filtrate was evaporated. The remaining residue was purified by column chromatography (10 g silica gel; heptane/EtOAc 90:10-70:30) to obtain [4-methyl-1-[4-(trifluoromethyl)phenyl]pyrazol-3-yl]methanol (59 mg) as yellow oil that solidified after standing. MS (ESI): 257.4 (M+H)⁺.

Step 5:
To a solution of [4-methyl-1-[4-(trifluoromethyl)phenyl]pyrazol-3-yl]methanol (54 mg; 0.211 mmol) in toluene (1 ml) was added thionyl chloride (76.4 µl) and the solution was stirred at RT for 2.5 h. All volatiles were removed to obtain the title compound (56 mg) as brown oil that solidified in the freezer. NMR (DMSO-d₆, 300 MHz): δ 2.15 (s, 3H), 4.82 (s, 2H), 7.85 (d, J=8.4 Hz, 2H), 8.00 (d, J=8.4 Hz, 2H) 8.45 (s, 1H).

Intermediate 25

3-Methyl-1-[4-(trifluoromethyl)phenyl]pyrazole-4-carbaldehyde

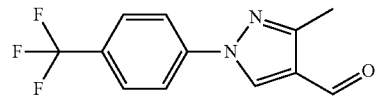

Step 1:
To a mixture of [4-(trifluoromethyl)phenyl]boronic acid (5.0 g, 26 mmol), 3-methyl-1H-pyrazole (1.08 g, 13 mmol) and pyridine (2.11 ml) in DCM (160 ml) were added anhydrous cupric(II)acetate (9.563 g, 53 mmol) and 4 Å molecular sieves and the reaction mixture was stirred at RT overnight. The mixture was then filtered with Celite and concentrated. The remaining residue was purified by column chromatography (100 g silica gel; heptane/EtOAc 95:5-80:20) to obtain 3-methyl-1-[4-(trifluoromethyl)phenyl]pyrazole (2.3 g) as white solid. MS (ESI): 227.4 (M+H)⁺.

Step 2:

To a solution of 3-methyl-1-[4-(trifluoromethyl)phenyl]pyrazole (1.0 g, 4 mmol) in DMF (10 ml) was added phosphorus oxychloride (607 µl) and the mixture was heated to 90° C. After 4 h again phosphorus oxychloride (405 µl) was added and heating to 90° C. was continued overnight. The reaction mixture was then poured on ice-water and this mixture was extracted with diethyl ether. The combined extracts were dried with Na$_2$SO$_4$ and concentrated. The remaining residue was purified by column chromatography (silica gel; heptane/EtOAc 4:1-2:1) to obtain the title compound (460 mg) as white solid. MS (ESI): 313.4 (M+OAc)$^-$.

Intermediate 26

[2-[4-(Trifluoromethyl)phenyl]-1H-imidazol-4-yl]methyl methanesulfonate

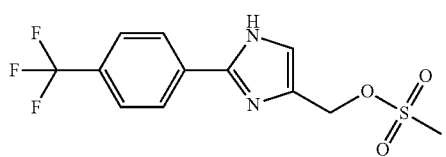 [SMILES: CS(=O)(=O)OCc1c[nH]c(-c2ccc(C(F)(F)F)cc2)n1]

Step 1:

A solution of 4-(trifluoromethyl)benzamidine; hydrochloride (8 g, 35.62 mmol) and 1,3-dihydroxyacetone dimer (6.42 g, 36.62 mmol) in ammonia solution (30%, 90 ml) was heated to 80° C. for 1 h. The reaction mixture was cooled and extracted with EtOAc. The combined organic layers were washed with water and brine, dried with Na$_2$SO$_4$ and evaporated. The remaining residue was purified by column chromatography (silica gel; EtOAc/hexane 4:1) to obtain [2-[4-(trifluoromethyl)phenyl]-1H-imidazol-4-yl]methanol as a pale brown solid. (3.2 g, 37%). $^1$H-NMR (DMSO-d$_6$, 400 MHz): δ 4.42 (d, J=5.6 Hz, 1H), 4.58 (d, J=5.76 Hz, 1H), 4.91 & 5.16 (a pair of t, J=5.6 Hz & 5.4 Hz, 1H), 6.94 & 7.16 (a pair of s, 1H), 4.91 & 5.16 (a pair of t, J=5.6 Hz & 5.4 Hz, 1H), 7.79 (d, J=8.12 Hz, 2H), 8.10 (d, J=8.16 Hz, 1H), 8.14 (d, J=8.20 Hz, 1H), 12.61 & 12.77 (a pair of s, 1H).

Step 2:

To a solution of [2-[4-(trifluoromethyl)phenyl]-1H-imidazol-4-yl]methanol (3 g, 12.38 mmol) in DCM (40 ml) was added triethylamine (3.4 ml, 24.39 mmol) followed by dropwise addition of mesyl chloride (1.43 ml, 18.5 mmol) at 0° C. The reaction mixture was stirred at RT for 2 h, washed with water and brine, dried with Na$_2$SO$_4$ and evaporated. The remaining residue was purified by column chromatography (silica gel; DCM/MeOH 96:4) to obtain the title compound as a pale brown solid. (2.6 g, 65%). $^1$H-NMR (DMSO-d$_6$, 400 MHz): δ 2.26 (s, 3H), 4.38 (s, 2H), 7.69 (s, 1H), 7.87 (d, J=8.44 Hz, 2H), 8.16 (d, J=8.2 Hz, 2H), 13.3 (brs, 1H).

Intermediate 27

[5-Methyl-2-[4-(trifluoromethyl)phenyl]-1H-imidazol-4-yl]methyl methanesulfonate

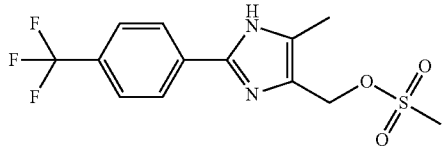 [SMILES: Cc1[nH]c(-c2ccc(C(F)(F)F)cc2)nc1COS(C)(=O)=O]

Step 1:

To a solution of 4-(trifluoromethyl)benzamidine; hydrochloride (10 g, 44.52 mmol) and 2,3-butanedione (4.6 g, 53.42 mmol) in water (50 ml) was added 2N NaOH solution (23 ml) at 0° C. until the pH of the mixture was adjusted to 8. The reaction mixture was stirred at 0° C. for 2.5 h. The precipitate that formed was collected by filtration and washed with water. Then 4N HCl (76 ml) was added and the mixture was heated to reflux for 4 h. The reaction mixture was then cooled to 0° C. and the pH was adjusted to 9 by slow addition of 8N NaOH solution. The precipitate that formed was collected by filtration washed successively with cold water, and 50% aqueous ethanol and dried under vacuum. The remaining solid was purified by column chromatography (silica gel; EtOAc/hexane 4:1) to obtain [5-methyl-2-[4-(trifluoromethyl)phenyl]-1H-imidazol-4-yl]methanol as a pale yellow solid (5.8 g, 51%). $^1$H-NMR (DMSO-d$_6$, 400 MHz): δ 2.14 & 2.25 (a pair of s, 3H), 4.35 (brs, 1H), 4.44 (brs, 1H), 4.70 (brs, 1H), 5.02 (brs, 1H), 7.76 (d, J=7.68 Hz, 2H), 7.99 (d, J=8.8 Hz, 2H), 8.05 (d, J=7.44 Hz, 1H), 8.11 (d, J=6.88 Hz, 1H), 12.40 & 12.53 (a pair of brs, 1H).

Step 2:

To a solution of [5-methyl-2-[4-(trifluoromethyl)phenyl]-1H-imidazol-4-yl]methanol (2.5 g, 9.76 mmol) in DCM (80 ml) was added triethylamine (2.72 ml, 19.51 mmol) followed by dropwise addition of mesyl chloride (1.13 ml, 14.60 mmol) at 0° C. The reaction mixture was stirred at RT for 2 h, washed with water and brine, dried with Na$_2$SO$_4$ and evaporated. The remaining residue was purified by column chromatography (silica gel; DCM/MeOH 96:4) to obtain the title compound as a pale brown solid. (3.1 g, 95%). $^1$H-NMR (DMSO-d$_6$, 400 MHz): δ 2.23 (s, 3H), 2.37 (s, 3H), 4.36 (s, 2H), 7.83 (d, J=8.2 Hz, 2H), 8.15 (d, J=8 Hz, 2H), 9.96 (brs, 1H).

Intermediate 28

4-(Bromomethyl)-5-methyl-2-[4-(trifluoromethyl)phenyl]thiazole

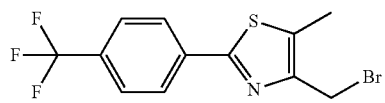

Step 1:

A solution of 4-trifluoromethyl-thiobenzamide (CAS 72505-21-6) (4 g, 19.5 mmol) and 3-chloro-2-butanone (3.9 ml, 39 mmol) in isopropanol (20 ml) was heated to reflux for 30 h. The reaction mixture was concentrated to a volume of 10 ml, cooled to 50° C. and diisopropylether (20 ml) was added dropwise. The solution was cooled to RT, the resulting crystals were filtered off, washed with ice cold diisopropylether and dried in vacuo to give 2.6 g (8.9 mmol) of 4,5-dimethyl-2-(4-trifluoromethyl-phenyl)-thiazole hydrochloride as off-white crystals. MS (ESI): 258.4 (M+H)$^+$.

Step 2:

4,5-Dimethyl-2-(4-trifluoromethyl-phenyl)-thiazole hydrochloride (2.6 g, 8.9 mmol) was suspended in ethyl acetate and ice water. Triethylamine (1.2 ml, 8.9 mmol) was added, the organic layer was separated and the aqueous layer was extracted with ethyl acetate. The combined organic layers were washed with brine/ice water 1/1 dried with sodium sulfate and the solvent was removed under reduced pressure. The residue was dried in vacuo and dissolved in acetonitrile (30 ml) under an argon atmosphere. The solution was cooled to 0° C., N-bromosuccinimide (2.05 g, 11.5 mmol) and 2,2'-azobis(2-methylpropionitrile) (145 mg, 0.89 mmol) were added and the reaction mixture was stirred at RT for 14 h. Water was added and the formed precipitate was filtered off, washed with water and dried in vacuo to give yellow crystals. The crystals were purified by column chromatography (silica gel, n-heptane/dichloromethane) to give 385 mg (1.2 mmol) of the title compound as off-white crystals. MS (ESI): 336.2 (M+H)$^+$.

Intermediate 29

5-Chloro-3-methyl-1-(4-piperidyl)benzimidazol-2-one

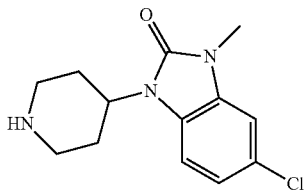 [SMILES: Cn1c(=O)n(C2CCNCC2)c2ccc(Cl)cc21]

Step 1:

5-Chloro-1-(4-piperidyl)-2-benzimidazolone (3 g; 97%; 11.56 mmol) was added portionwise to a solution of di-tert-butyl-dicarbonate (2.575 g; 98%; 11.56 mmol) in THF (35 ml) at 0° C. After the addition was completed, the reaction mixture was stirred for 1.5 h at 0° C. The reaction mixture was allowed to warm to RT and diluted Na$_2$CO$_3$ solution (~30 ml) was added. The mixture was extracted with diethyl ether and the organic layers were combined, dried with Na$_2$SO$_4$ and evaporated. The remaining residue was triturated with diethyl ether to obtain tert-butyl 4-(5-chloro-2-oxo-3H-benzimidazol-1-yl)piperidine-1-carboxylate (3.936 g) as with solid. MS (ESI): 352.4 (M+H)$^+$.

Step 2:

To a suspension of sodium hydride (55% dispersion in oil, 27 mg; 0.625 mmol) in DMF was added a solution of tert-butyl 4-(5-chloro-2-oxo-3H-benzimidazol-1-yl)piperidine-1-carboxylate (200 mg; 0.568 mmol) in DMF (2 ml) dropwise at RT. After 1 h a solution of methyl iodide (38.9 µl; 0.625 mmol) in DMF (0.5 ml) was added dropwise and the reaction mixture was stirred at RT for 1.5 h. Again methyl iodide (38.9 µl; 0.625 mmol) in DMF (0.5 ml) was added and the reaction mixture was stirred for 3.5 h at RT. Then ice/water was added and the mixture was extracted with EtOAc. The combined organic layers were washed with water and brine, dried with Na$_2$SO$_4$ and evaporated to obtain tert-butyl 4-(5-chloro-3-methyl-2-oxo-benzimidazol-1-yl)piperidine-1-carboxylate (200 mg) as white foam. MS (ESI): 366.0 (M+H)$^+$.

Step 3:

To a solution of tert-butyl 4-(5-chloro-3-methyl-2-oxo-benzimidazol-1-yl)piperidine-1-carboxylate (200 mg; 0.547 mmol) in DCM (2 ml) was added TFA (0.5 ml) at RT. The solution was stirred at RT for 1.5 h. All volatiles were removed and the residue was partitioned between 1N NaOH solution and DCM. The layers were separated and the aqueous layer was extracted with DCM. The combined organic layers were dried with Na$_2$SO$_4$ and evaporated to obtain the title compound (129 mg) as with solid. MS (ESI): 266.1 (M+H)$^+$.

The following intermediates were prepared in analogy to intermediate 29:

| Int. | Name | Structure | MS (ESI) | Reagent used in step 2 |
|---|---|---|---|---|
| 30 | 5-Chloro-3-ethyl-1-(4-piperidyl)benzimidazol-2-one | 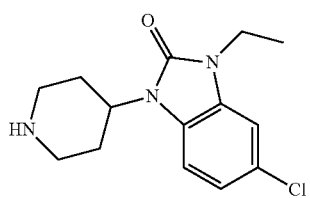 [SMILES: CCn1c(=O)n(C2CCNCC2)c2ccc(Cl)cc21] | 280.3 (M + H)$^+$ | Ethyl iodide |
| 31 | 5-Chloro-3-(2-methoxyethyl)-1-(4-piperidyl)benzimidazol-2-one | 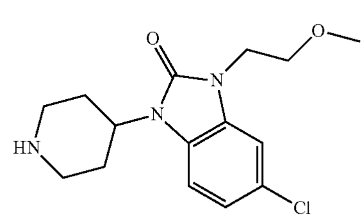 [SMILES: COCCn1c(=O)n(C2CCNCC2)c2ccc(Cl)cc21] | 310.3 (M + H)$^+$ | 2-Bromoethyl methyl ether |

-continued

| Int. | Name | Structure | MS (ESI) | Reagent used in step 2 |
|---|---|---|---|---|
| 32 | 2-[6-Chloro-2-oxo-3-(4-piperidyl)benzimidazol-1-yl]ethylacetate | 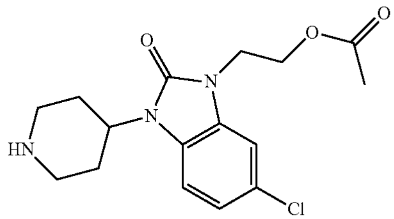 [SMILES: CC(=O)OCCn1c(=O)n(C2CCNCC2)c2ccc(Cl)cc21] | 338.4 (M + H)+ | 2-Bromoethyl acetate |
| 33 | 2-[6-Chloro-2-oxo-3-(4-piperidyl)benzimidazol-1-yl]acetamide | 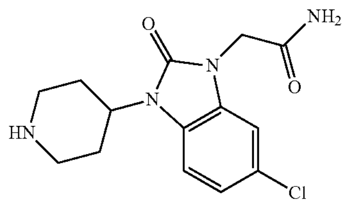 [SMILES: NC(=O)Cn1c(=O)n(C2CCNCC2)c2ccc(Cl)cc21] | 309.1 (M + H)+ | 2-Bromoacetamide |
| 34 | 2-[6-Chloro-2-oxo-3-(4-piperidyl)benzimidazol-1-yl]-N-methyl-acetamide | 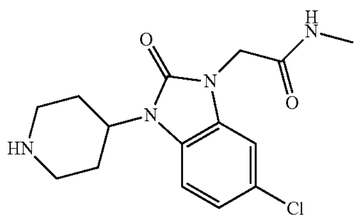 [SMILES: CNC(=O)Cn1c(=O)n(C2CCNCC2)c2ccc(Cl)cc21] | 323.3 (M + H)+ | 2-Chloro-N-methylacetamide |
| 35 | Methyl 2-[6-chloro-2-oxo-3-(4-piperidyl)benzimidazol-1-yl]acetate | 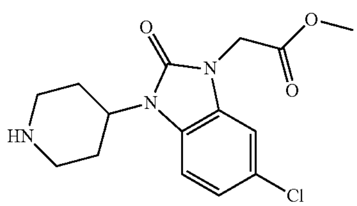 [SMILES: COC(=O)Cn1c(=O)n(C2CCNCC2)c2ccc(Cl)cc21] | 324.1 (M + H) | Methyl bromoacetate |

Intermediate 36

5-Chloro-3-(2-methylsulfonylethyl)-1-(4-piperidyl)benzimidazol-2-one

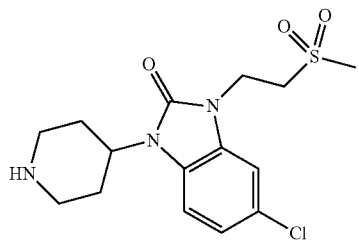 [SMILES: CS(=O)(=O)CCn1c(=O)n(C2CCNCC2)c2ccc(Cl)cc21]

Step 1:

A solution of tert-butyl 4-[5-chloro-3-(2-methylsulfanyl-ethyl)-2-oxo-benzimidazol-1-yl]piperidine-1-carboxylate (195 mg; 0.458 mmol, prepared in analogy to tert-butyl 4-(5-chloro-3-methyl-2-oxo-benzimidazol-1-yl)piperidine-1-carboxylate (Intermediate 29, step 2) using 2-chloroethylmethylsulfide instead of methyl iodide) in MeOH (2.5 ml) was cooled to 0° C. and a solution of Oxone (422 mg; 0.687 mmol) in water (2 ml) was added slowly. The reaction mixture was stirred for 4 h, then diluted with water and extracted with EtOAc. The combined organic layers were washed with water, dried with Na₂SO₄ and evaporated to obtain tert-butyl 4-[5-chloro-3-(2-methylsulfonylethyl)-2-oxo-benzimidazol-1-yl]piperidine-1-carboxylate (203 mg) as white foam. MS (ESI): 458.1 (M+H)+.

Step 2:

The title compound was prepared in analogy to intermediate 29 from tert-butyl 4-[5-chloro-3-(2-methylsulfonyl-ethyl)-2-oxo-benzimidazol-1-yl]piperidine-1-carboxylate and was obtained as white foam. MS (ESI): 358.1 (M+H)+.

Intermediate 37

1-Methyl-3-(4-piperidyl)-4H-quinazolin-2-one

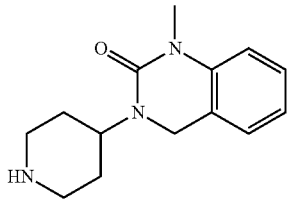 [SMILES: CN1C(=O)N(C2CCNCC2)Cc2ccccc21]

Step 1:

To a suspension of sodium hydride (55% dispersion in oil, 15 mg; 0.3 mmol) in DMF (0.5 ml) was added a solution of 3-(1-benzyl-4-piperidyl)-1,4-dihydroquinazolin-2-one (CAS 79098-88-7) (100 mg, 0.3 mmol) in DMF (2 ml). The mixture was stirred at RT for 1 h and then a solution of methyl iodide (21 µl) in DMF (2 ml) was added and the reaction mixture was stirred at RT overnight. More methyl iodide (4 µl) was added and the reaction mixture was heated to 40° C. for 1 h. Ice water was added and the mixture was extracted with EtOAc. The combined extracts were dried with Na$_2$SO$_4$ and evaporated to obtain 3-(1-benzyl-4-piperidyl)-1-methyl-4H-quinazolin-2-one (104 mg) as yellow oil. MS (ESI): 336.4 (M+H)$^+$.

Step 2:

A solution of 3-(1-benzyl-4-piperidyl)-1-methyl-4H-quinazolin-2-one (102 mg) in ethanol (12 ml) was kept under an atmosphere of hydrogen in the presence of palladium (10% on carbon, 10 mg) for 2 days. The solution was then filtered with Dicalit and the filtrate was evaporated to obtain the title compound (75 mg) as greenish oil which was used in the next reaction step without further purification. MS (ESI): 244.3 (M−H)$^-$.

Intermediate 38

1-(2-Methoxyethyl)-3-(4-piperidyl)-4H-quinazolin-2-one

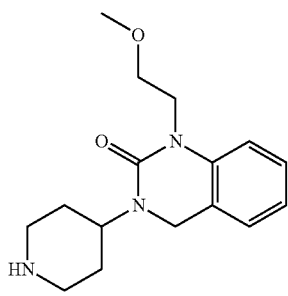 [SMILES: COCCN1C(=O)N(C2CCNCC2)Cc2ccccc21]

The title compound was prepared in analogy to intermediate 37 from 3-(1-benzyl-4-piperidyl)-1,4-dihydroquinazolin-2-one using 2-bromoethyl methyl ether instead of methyl iodide in step 1 and was obtained as greenish oil which was used in the next reaction step without further purification. MS (ESI): 290.3 (M+H)$^+$.

Intermediate 39

7-Fluoro-3-(4-piperidyl)-1,4-dihydroquinazolin-2-one

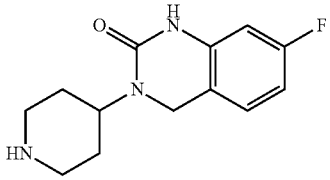 [SMILES: O=C1Nc2cc(F)ccc2CN1C1CCNCC1]

Step 1:

To a mixture of 4-fluoro-2-nitrobenzoic acid (4.0 g, 22 mmol), 4-amino-1-benzylpiperidine (4.523 g, 24 mmol), 1-hydroxybenzotriazole (584 mg, 4 mmol) and triethylamine (6.024 ml, 43 mmol) in EtOAc (60 ml) was added N-(3-dimethylaminopropyl)-N'-ethylcarbodiimide hydrochloride (4.971 g, 26 mmol) and the mixture was stirred overnight. Water was added and the mixture was extracted with EtOAc. The combined extracts were washed with brine, dried with Na$_2$SO$_4$ and evaporated. The remaining residue was triturated with EtOAc to obtain N-(1-benzyl-4-piperidyl)-4-fluoro-2-nitro-benzamide (4.0 g) as weak yellow solid. MS (ESI): 356.5 (M−H)$^-$.

Step 2:

A suspension of lithium aluminum hydride (5.04 g, 132.8 mmol) in dioxane (30 ml) was heated to reflux. Then a solution of N-(1-benzyl-4-piperidyl)-4-fluoro-2-nitro-benzamide (5.9 g, 37.9 mmol) in dioxane (55 ml) was added dropwise over a period of 30 min and heating to reflux was continued for 6 h. The reaction mixture was cooled to 0° C. and water (10 ml) was added carefully. The mixture was then poured onto 50% aqueous NaOH solution (50 ml) and extracted with diethyl ether. The combined extracts were dried with Na$_2$SO$_4$ and evaporated. The remaining residue was purified by column chromatography (200 g silica gel; DCM/MeOH 97:3-90:10) to obtain 2-amino-N-(1-benzyl-4-piperidyl)-4-fluoro-benzamide as yellow oil (1.75 g). MS (ESI): 314.1 (M+H)$^+$.

Step 3:

To a solution of 2-amino-N-(1-benzyl-4-piperidyl)-4-fluoro-benzamide (1.3 g, 4.1 mmol) in THF (20 ml) was added 1,1'-carbonyl-diimidazole at 0° C. The reaction mixture was stirred for 15 min at 0° C. and then at RT for 4 h. Water was added and the mixture was extracted with EtOAc. The combined extracts were washed with brine, dried with Na$_2$SO$_4$ and evaporated. The remaining residue was triturated with EtOAc to obtain 3-(1-benzyl-4-piperidyl)-7-fluoro-1,4-dihydroquinazolin-2-one as white solid (1 g). MS (ESI): 338.5 (M−H)$^-$.

Step 4:

A solution of 3-(1-benzyl-4-piperidyl)-7-fluoro-1,4-dihydroquinazolin-2-one (1.36 g) in ethanol (12 ml) was kept under an atmosphere of hydrogen in the presence of palladium (10% on carbon, 136 mg) overnight. The reaction mixture was filtered with Dicalite and the filtrate was evaporated to obtain the title compound as white solid (1.1 g). MS (ESI): 250.3 (M+H)$^+$.

Intermediate 40

3-(4-Piperidyl)-1H-pyrrolo[3,2-c]pyridine

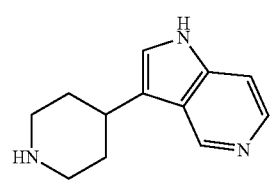 [SMILES: c1cc2[nH]cc(C3CCNCC3)c2cn1]

Step 1:

To a mixture of 1H-pyrrolo[3,2-c]pyridine (CAS 271-34-1) (180 mg, 1.5 mmol) and tert-butyl 4-oxopiperidine-1-carboxylate (607 mg, 3 mmol) in MeOH (5 ml) was added potassium hydroxide (342 mg, 6.1 mmol) and the mixture was heated to reflux overnight. More tert-butyl 4-oxopiperidine-1-carboxylate (155 mg) was added and the reaction mixture was again heated to reflux overnight. The reaction mixture was poured on ice water and was extracted with DCM. The combined extracts were dried with Na$_2$SO$_4$ and evaporated. The remaining residue was triturated with MeOH and filtered. The filtrate was evaporated and the remaining oil was purified by column chromatography (50 g silica gel; DCM/MeOH 98:2-90:10) to obtain tert-butyl 4-(1H-pyrrolo[3,2-c]pyridin-3-yl)-3,6-dihydro-2H-pyridine-1-carboxylate (350 mg) as light orange solid. MS (ESI): 298.5 (M–H)⁻.

Step 2:
To a mixture of tert-butyl 4-(1H-pyrrolo[3,2-c]pyridin-3-yl)-3,6-dihydro-2H-pyridine-1-carboxylate (350 mg) and PtO$_2$ (40 mg, 80.5%) in ethanol (8 ml) hydrogen pressure (4.1 bar) was applied overnight. The reaction mixture was filtered with Dicalite and the filtrate was evaporated. 160 mg from the remaining residue were again dissolved in ethanol (5 ml), PtO$_2$ (40 mg, 80.5%) was added and again hydrogen pressure (4.1 bar) was applied overnight. The reaction mixture was filtered with Dicalite and the filtrate was evaporated to obtain tert-butyl 4-(1H-pyrrolo[3,2-c]pyridin-3-yl)piperidine-1-carboxylate (138 mg) as light yellow solid. MS (ESI): 300.5 (M–H)⁻.

Step 3:
To a solution of tert-butyl 4-(1H-pyrrolo[3,2-c]pyridin-3-yl)piperidine-1-carboxylate (138 mg) in DCM (3 ml) was added TFA (350 µl) and the mixture was stirred at RT for 3 h. Then 1N NaOH solution was added until the pH was adjusted to 12 and the mixture was extracted with DCM. The combined extracts were dried with Na$_2$SO$_4$ and evaporated to obtain the title compound (50 mg) as light yellow solid. MS (ESI): 202.3 (M+H)⁺.

Intermediate 41

5-chloro-1-(4-piperidyl)indolin-2-one

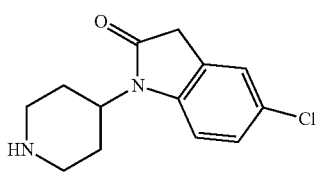 [SMILES: O=C1Cc2cc(Cl)ccc2N1C1CCNCC1]

Step 1:
To sodium hydride (55% dispersion in oil, 5.454 g, 125 mmol) was carefully added DMSO (80 ml) and the mixture was heated slowly to 100° C. Then a solution of diethyl malonate (7.915 ml, 52 mmol) in DMSO (10 ml) was added and 10 min after completion of the addition a solution of 2,4-dichloronitrobenzene (10 g, 52 mmol) in DMSO (10 ml) was added. The mixture was heated to 100° C. for 1.5 h, then stirred at RT overnight and finally poured on water and extracted with diethyl ether. The organic extracts were dried with Na$_2$SO$_4$ and evaporated to obtain a brown oil that was subjected to Kugelrohr distillation. Diethyl 2-(5-chloro-2-nitro-phenyl)propanedioate was obtained with ~85% purity (15.3 g) and was used in the next reaction step without further purification. MS (ESI): 314.3 (M–H)⁻.

Step 2:
To a solution of diethyl 2-(5-chloro-2-nitro-phenyl)propanedioate (15.3 g from step 1, ~15.3 g) in DMSO (150 ml) were added lithium chloride (4.314 g) and water (960 µl) and the mixture was heated to 120° C. for 4 d. Then water was added and the mixture was extracted with EtOAc. The combined extracts were dried with Na$_2$SO$_4$ and evaporated and the remaining residue was purified by column chromatography (200 g silica gel; heptane/EtOAc 4:1) to obtain ethyl 2-(5-chloro-2-nitro-phenyl)acetate (6.98 g) as light brown oil. MS (ESI): 242.3 (M–H)⁻.

Step 3:
To a mixture of ethyl 2-(5-chloro-2-nitro-phenyl)acetate (6.6 g) and PtO$_2$ (1.32 g, 80.5%) in benzene (200 ml) hydrogen pressure (2.8 bar) was applied for 3 h. The reaction mixture was filtered with Dicalite and the filtrate was evaporated to obtain ethyl 2-(2-amino-5-chloro-phenyl)acetate (5.8 g) that was used in the next reaction step without further purification. MS (ESI): 214.1 (M+H)⁺.

Step 4:
To a mixture of ethyl 2-(2-amino-5-chloro-phenyl)acetate (5.6 g) and tert-butyl 4-oxopiperidine-1-carboxylate (7.833 g) in DCM (50 ml) were added sodium triacetoxyborohydride (8.170 g) and AcOH (4.5 ml) and the mixture was stirred at RT for 4 d. Saturated NaHCO$_3$ solution was added and the mixture was extracted with EtOAc. The combined extracts were dried with Na$_2$SO$_4$ and evaporated and the remaining residue was triturated with EtOAc to obtain tert-butyl 4-(5-chloro-2-oxo-indolin-1-yl)piperidine-1-carboxylate (4.48 g) as white solid. MS (ESI): 349.2 (M–H)⁻.

Step 5:
To a solution of tert-butyl 4-(5-chloro-2-oxo-indolin-1-yl)piperidine-1-carboxylate (650 mg) in DCM (6.5 ml) was added TFA (1.42 ml) and the mixture was stirred at RT for 1 h. Then 1N NaOH solution was added until the pH was adjusted to 12 and the mixture was extracted with DCM. The combined extracts were dried with Na$_2$SO$_4$ and evaporated to obtain the title compound (430 mg) as light brown solid. MS (ESI): 251.1 (M+H)⁺.

Intermediate 42

5-(4-Bromophenyl)-3-(4-piperidyl)-1H-imidazol-2-one; trifluoroacetic acid salt

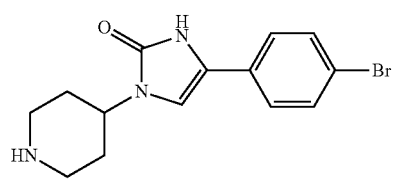

TFA salt

Step 1:
A solution of 2-bromo-1-(4-bromophenyl)ethanone (30.53 g, 100 mmol) in DCM (50 ml) was added to a suspension of tert-butyl 4-aminopiperidine-1-carboxylate (20 g, 90 mmol) and sodium acetate (8.18 g, 90 mmol) in DCM (150 ml) at 0° C. The reaction mixture was stirred at RT for 16 h. A solution of sodium cyanate (9.73 g, 140 mmol) in water (10 ml) was added to the reaction mixture followed by the addition of glacial acetic acid (20 ml). The reaction mixture was again stirred at RT for 16 h. The reaction mixture was poured into crushed ice and stirred for half an hour. The organic layer was separated and washed successively with water, saturated NaHCO$_3$ solution and citric acid solution and finally again with water, dried with Na$_2$SO$_4$ and evaporated under reduced pressure. The residue was stirred with diethyl ether (200 ml) and filtered; the solid thus obtained was again stirred with methanol (100 ml) for 0.5 h and filtered to get a light yellow solid, which was dried under high vacuum to get tert-butyl 4-[5-(4-bromophenyl)-2-oxo-1H-imidazol-3-yl]piperidine-1-carboxylate (10.75 g). MS (ESI): 422 (M+H)⁺.

Step 2:

Tert-butyl 4-[5-(4-bromophenyl)-2-oxo-1H-imidazol-3-yl]piperidine-1-carboxylate was dissolved in a mixture of DCM and TFA 4:1 (3 ml/1 mmol) at 0° C. and the mixture was stirred for 2 h. DCM was completely evaporated, the remaining residue was dissolved in chloroform and again evaporated to remove residual of TFA. The title compound obtained by this procedure was used in the next reaction steps without further purification.

Intermediate 43

5-(4-Bromophenyl)-2-(4-piperidyl)-4H-1,2,4-triazol-3-one; Trifluoroacetic Acid Salt

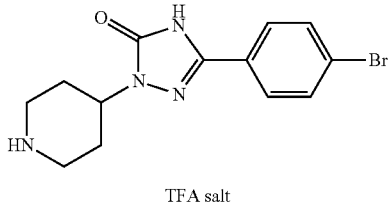 [SMILES: O=c1[nH]c(-c2ccc(Br)cc2)nn1C1CCNCC1]

TFA salt

Step 1:

Ethoxycarbonylisothiocyanate (11 g, 83 mmol) was added to a solution of bromobenzene (15.8 g, 100 mmol) in DCM (85 ml). Anhydrous aluminium chloride (22.34 g, 167 mmol) was added portionwise to the reaction mixture at 0° C. The reaction mixture was then stirred at the same temperature for 4 h. Ice cold water was added carefully over a period of 1 h. The organic layer was separated, washed with water, dried with Na₂SO₄ and evaporated. The remaining residue was purified by silica gel column chromatography (silica gel; hexane/EtOAc 95:5) to obtain ethyl N-(4-bromobenzenecarbothioyl)carbamate (3.3 g). MS (ESI): 288 (M+H)⁺.

Step 2:

Hydrazine hydrate (125 ml, 2.5 mol) was added to a solution of tert-butyl 4-oxopiperidine-1-carboxylate (25 g, 0.125 mol) in ethanol (225 ml) and the reaction mixture was stirred at RT for 12 h. The reaction mixture was cooled and sodium borohydride (17.7 g, 0.48 mmol) was added portionwise. The reaction mixture was stirred at the same temperature for 2 h. The solvent was evaporated and the residue was dissolved in DCM. The DCM solution was washed with water, dried with Na₂SO₄ and evaporated to obtain tert-butyl 4-hydrazinopiperidine-1-carboxylate (18 g).

Step 3:

Diisopropylethyl amine (20.7 g, 129 mmol) was added to a solution of tert-butyl 4-hydrazinopiperidine-1-carboxylate (16.43 g, 76 mmol, from step 2) and ethyl N-(4-bromobenzenecarbothioyl)carbamate (20 g, 70 mmol, from step 1) in THF (440 ml). The reaction mixture was heated to reflux for 2 h, then cooled and the precipitate that formed was filtered. The white solid thus obtained was dried to obtain tert-butyl 4-[3-(4-bromophenyl)-5-oxo-4H-1,2,4-triazol-1-yl]piperidine-1-carboxylate (14 g). MS (ESI): 423 (M+H)⁺.

Step 4:

Tert-Butyl 4-[3-(4-bromophenyl)-5-oxo-4H-1,2,4-triazol-1-yl]piperidine-1-carboxylate was converted to the title compound in analogy to intermediate 42, step 2 and was used for the next reaction step without further purification.

Intermediate 44

6-Bromo-3-(4-piperidyl)-1,4-dihydroquinazolin-2-one; hydrochloride

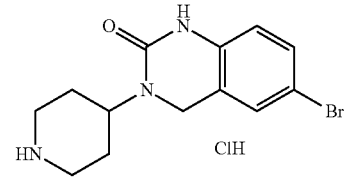 [SMILES: O=C1Nc2ccc(Br)cc2CN1C1CCNCC1 ; Cl]

Step 1:

Tert-butyl 4-aminopiperidine-1-carboxylate (34.76 g, 173.5 mmol) was added to a solution of 5-bromo-2-nitrobenzaldehyde (20357-20-4) (36.30 g, 157 mmol) in methanol (200 ml) and the reaction mixture was stirred at RT for 1 h. Sodium borohydride (8.95 g, 236.5 mmol) was added portionwise to the reaction mixture at 0° C. and stirring was continued for 1 h. Saturated ammonium chloride solution was added at 0° C. and the methanol was evaporated. The mixture was extracted with EtOAc and the combined organic layers were washed with water, dried with Na₂SO₄ and evaporated. The remaining residue was purified by column chromatography (silica gel; hexane/EtOAc 95:5 to 90:10) to obtain tert-butyl 4-[(5-bromo-2-nitro-phenyl)methylamino]piperidine-1-carboxylate (40 g). MS (ESI): 414 (M+H)⁺.

Step 2:

Ammonium chloride (11.61 g, 217.05 mmol) was added to a suspension of tert-butyl 4-[(5-bromo-2-nitro-phenyl)methylamino]piperidine-1-carboxylate (30 g, 72.4 mmol) and zinc dust (33.13 g, 506.65 mmol) in methanol (700 ml). The reaction mixture was heated under refluxed for 1 h. The reaction mixture filtered through Celite and the filtrate was evaporated. Water was added and the mixture was extracted with DCM. The combined organic layers were washed with water, dried with Na₂SO₄ and evaporated. The remaining residue was purified by silica gel column chromatography to obtain tert-butyl 4-[(2-amino-5-bromo-phenyl)methylamino]piperidine-1-carboxylate (18 g). MS (ESI): 384 (M+H)⁺.

Step 3:

Carbonyldiimidazole (2.63 g, 16.2 mmol) was added to a solution of tert-butyl 4-[(2-amino-5-bromo-phenyl)methylamino]piperidine-1-carboxylate (5.0 g, 13.0 mmol) and triethylamine (5.48 ml, 38.9 mmol) in acetonitrile (40 ml) and the reaction was stirred at RT for 2 h. Another portion of carbonyldiimidazole (1.68 g, 1.03 mmol) was added and stirring was continued for another 2 h. The Solvent was evaporated under reduced pressure. Water was added and the mixture was extracted with EtOAc. The combined extracts were washed with water, dried with Na₂SO₄ and evaporated. The remaining residue was purified by column chromatography (silica gel; hexane/EtOAc 70:30 to 60:40) to obtain tert-butyl 4-(6-bromo-2-oxo-1,4-dihydroquinazolin-3-yl)piperidine-1-carboxylate (2.5 g). MS (ESI): 410 (M+H)⁺.

Step 4:

Tert-butyl 4-(6-bromo-2-oxo-1,4-dihydroquinazolin-3-yl)piperidine-1-carboxylate was dissolved in a saturated solution of HCl gas in EtOAc. After 2 h, all volatiles were removed to obtain the title compound that was used for the next reaction step without further purification.

Intermediate 45

1-(4-Piperidyl)-5H-imidazo[4,5-c]pyridin-4-one; hydrochloride

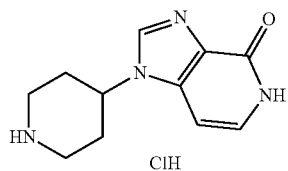 [SMILES: O=c1[nH]ccc2c1ncn2C1CCNCC1 ; Cl]

Step 1:

To a solution of tert-butyl 4-aminopiperidine-1-carboxylate (31.75 g, 158.5 mmol) in DMF (30 ml) was added to a solution of 4-chloro-3-nitro-pyridine (CAS 13091-23-1) (25 g, 157.6 mmol) and triethylamine (25.65 ml, 189 mmol) in DMF (100 ml) and the reaction mixture was stirred at RT for 15 h. The reaction mixture was poured into ice-cold water and this mixture was stirred for 2 h, then allowed to settle for another 2 h and filtered. The orange solid that was collected was washed with water, dried and re-crystallized from EtOAc to obtain tert-butyl 4-[(3-nitro-4-pyridyl)amino]piperidine-1-carboxylate (44 g).

Step 2:

Palladium (2.5 g, 10% on carbon) was added to a solution of tert-butyl 4-[(3-nitro-4-pyridyl)amino]piperidine-1-carboxylate (25 g, 77.5 mmol) in ethanol (375 ml) and hydrogen pressure (50 psi) was applied in a parr shaker for 16 h. The reaction mixture was filtered through Celite and the filtrate was evaporated. The remaining residue was triturated with diethyl ether to obtain tert-butyl 4-[(3-amino-4-pyridyl)amino]piperidine-1-carboxylate (18.45 g). MS (ESI): 293 (M+H)$^+$.

Step 3:

4-Toluene sulfonic acid (0.65 g, 3.4 mmol) was added to a solution of tert-butyl 4-[(3-amino-4-pyridyl)amino]piperidine-1-carboxylate (10.0 g, 34.22 mmol) and triethylorthoformate (10.14 g, 68 mmol) in toluene (70 ml) and the mixture was heated to reflux for 16 h. The solvent was evaporated and the remaining residue was triturated with diethyl ether to obtain tert-butyl 4-imidazo[4,5-c]pyridin-1-ylpiperidine-1-carboxylate (7.5 g). MS (ESI): 303 (M+H)$^+$.

Step 4:

3-Chloroperbenzoic acid (7.4 g, 33 mmol, 77%) was added to a solution of tert-butyl 4-imidazo[4,5-c]pyridin-1-ylpiperidine-1-carboxylate (10 g, 33 mmol) in DCM (100 ml) at 10° C. and the reaction mixture was stirred at RT for 18 h. The solvent was evaporated and the remaining residue was purified by column chromatography (neutral alumina; DCM/MeOH 95:5 to 70:30) to obtain tert-butyl 4-(5-oxidoimidazo[4,5-c]pyridin-5-ium-1-yl)piperidine-1-carboxylate (8.2 g). MS (ESI): 319 (M+H)$^+$.

Step 5:

A solution of tert-butyl 4-(5-oxidoimidazo[4,5-c]pyridin-5-ium-1-yl)piperidine-1-carboxylate (10 g, 31.4 mmol) in acetic anhydride (100 ml) was heated to reflux for 18 h. The acetic anhydride was evaporated under reduced pressure. The remaining residue was purified by column chromatography (neutral alumina; DCM/MeOH 97:3) to obtain 1-(1-acetyl-4-piperidyl)-5H-imidazo[4,5-c]pyridin-4-one (4.8 g). MS (ESI): 261 (M+H)$^+$.

Step 6:

Concentrated HCl (24 ml) was added to a solution of 1-(1-acetyl-4-piperidyl)-5H-imidazo[4,5-c]pyridin-4-one (6.0 g, 18.8 mmol) in ethanol (48 ml) and the reaction mixture was heated to reflux for 16 h. The solvent was evaporated under reduced pressure and the remaining residue was precipitated with ethanol. The precipitate was filtered off and washed with diethyl ether to obtain the title compound as brown solid (4.5 g). MS (ESI): 219 (M+H)$^+$.

Intermediate 46

3-(4-Piperidyl)-5-pyrrolidin-1-yl-1H-benzimidazol-2-one; hydrochloride

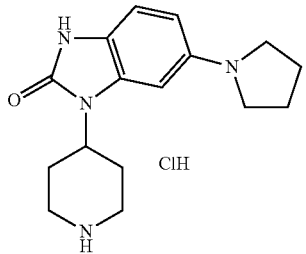 [SMILES: O=c1[nH]c2ccc(N3CCCC3)cc2n1C1CCNCC1 ; Cl]

Step 1:

To a solution of 2,4-dichloro-1-nitro-benzene (65 g, 0.34 mol) in DMF was added tert-butyl 4-aminopiperidine-1-carboxylate (114 g, 0.57 mol) and K$_2$CO$_3$ (94 g, 0.68 mol) and the mixture was heated to 85-90° C. for 48 h. DMF was removed under vacuum and water was added to the remaining residue. The mixture was extracted with EtOAc and the extracts were dried with Na$_2$SO$_4$ and evaporated. The remaining residue was purified by column chromatography to obtain tert-butyl 4-(5-chloro-2-nitro-anilino)piperidine-1-carboxylate (75 g) as a yellow powder. $^1$H-NMR (DMSO-d$_6$, 400 MHz): δ 1.40 (s, 9H), 1.40-1.45 (m, 2H), 1.89-1.92 (m, 2H), 2.96 (brs, 2H), 3.87-3.90 (m, 3H), 6.70-6.73 (m, 1H), 7.27 (brs, 1H), 7.95-8.09 (m, 2H).

Step 2:

A mixture of tert-butyl 4-(5-chloro-2-nitro-anilino)piperidine-1-carboxylate (60 g, 0.17 mol), K$_2$CO$_3$ (47 g, 0.34 mol) and pyrrolidine (265 mL) was heated to reflux. After completion of the reaction, all volatiles were distilled off and water was added to the residual material. The solid formed was filtered and dried to give tert-butyl 4-(2-nitro-5-pyrrolidin-1-yl-anilino)piperidine-1-carboxylate (60 g) as a yellow solid. MS (ESI): 391 (M+H)$^+$.

Step 3:

A solution of tert-butyl 4-(2-nitro-5-pyrrolidin-1-yl-anilino)piperidine-1-carboxylate in ethanol was subjected to catalytic hydrogenation using palladium on carbon as a catalyst and applying a hydrogen pressure of 50 psi for 12 hours in presence of catalytic amount of triethylamine. The reaction mixture was filtered over Celite under argon. The filtrate is concentrated under reduced pressure in presence of argon to give tert-butyl 4-(2-amino-5-pyrrolidin-1-yl-anilino)piperidine-1-carboxylate as black viscous mass which was immediately used as such for the next step. MS (ESI): 361 (M+H)+.

Step 4:

A mixture of tert-butyl 4-(2-amino-5-pyrrolidin-1-yl-anilino)piperidine-1-carboxylate (69 g, 0.19 mol), triethylamine (80 mL, 0.58 mol) and 1,1'-carbonyl-diimidazole (62 g, 0.38 mol) in acetonitrile (600 ml) was stirred at RT for 4 h and then heated to reflux for 30 min. The solvent was removed, water was added and the mixture was extracted with DCM. The organic extracts were concentrated and the remaining residue was purified by column chromatography with neutral alumina to obtain tert-butyl 4-(2-oxo-6-pyrrolidin-1-yl-3H-benzimidazol-1-yl)piperidine-1-carboxylate (45 g) as a white solid. MS (ESI): 387 (M+H)+.

Step 5:

Tert-butyl 4-(2-oxo-6-pyrrolidin-1-yl-3H-benzimidazol-1-yl)piperidine-1-carboxylate (1 g) was dissolved in a HCl solution in dioxane (20 ml) and the mixture was stirred at RT. After 10 min all volatiles were removed to obtain the title compound (897 mg) as purple solid that was used in the next reaction step without further purification. MS (ESI): 287.1 (M+H)+.

The following intermediates were prepared in analogy to intermediate 46:

Enzyme is added to the substance dilutions in 96-well microtitre plates and the reaction is started with substrate. Fluorescence emission is measured over 20 minutes, during which time a linear increase is observed in the absence of inhibitor. $IC_{50}$ are calculated by standard methods.

Inhibition of human Cat S, mouse Cat S, human Cat K, mouse Cat K, human Cat B, mouse Cat B, human Cat L and mouse Cat L have been measured separately. The results obtained for human Cat S are expressed in the following table.

The compounds of the invention have a CatS $IC_{50}$ below 5 uM. Particular compounds of the invention have a CatS $IC_{50}$ below 1 uM, in particular below 0.1 uM.

The compound of formula (I) is a preferential human Cat S inhibitor with a selectivity over human Cat K, Cat B and Cat L of at least 10 fold.

| Example | CatS $IC_{50}$ uM |
|---|---|
| 1 | 0.28 |
| 2 | 0.78 |
| 3 | 0.45 |

| Int. | Name | Structure | MS (ESI) | Reagent used in step 2 |
|---|---|---|---|---|
| 47 | Morpholino-3-(4-piperidyl)-1H-benzimidazol-2-one; hydrochloride | 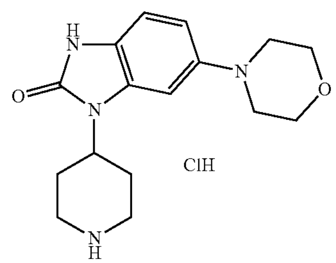 [SMILES: O=c1[nH]c2ccc(N3CCOCC3)cc2n1C1CCNCC1 ; Cl] | 303.3 (M + H)+ | Morpholine |
| 48 | 5-(4-Methylpiperazin-1-yl)-3-(4-piperidyl)-1H-benzimidazol-2-one; dihydrochloride | 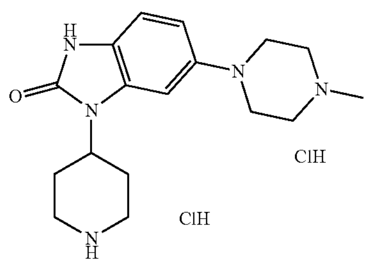 [SMILES: CN1CCN(c2ccc3[nH]c(=O)n(C4CCNCC4)c3c2)CC1 ; Cl ; Cl] | 316.2 (M + H)+ | 1-Methylpiperazine |

Example 82

Cathepsin Enzyme Inhibition Assay

Enzyme activity is measured by observing the increase in fluorescence intensity caused by cleavage of a peptide substrate containing a fluorophore whose emission is quenched in the intact peptide.

Assay buffer: 100 mM potassium phosphate pH 6.5, EDTA-Na 5 mM, Triton X-100 0.001%, DTT 5 mM.

Enzymes (all at 1 nM): human and mouse Cathepsin S, Cat K, Cat B, Cat L.

Substrate (20 Z-Val-Val-Arg-AMC, except for Cat K which uses Z-Leu-Arg-AMC (both from Bachem).

Z=Benzyloxycarbonyl.

AMC=7-Amino-4-Methyl-Coumarin.

DTT=dithiothreitol.

Final volume: 100 μL.

Excitation 360 nm, Emission 465 nm.

-continued

| Example | CatS $IC_{50}$ uM |
|---|---|
| 4 | 2.545 |
| 5 | 2.045 |
| 6 | 0.42 |
| 7 | 0.245 |
| 8 | 3.275 |
| 9 | 0.19 |
| 10 | 0.28 |
| 11 | 0.46 |
| 12 | 0.59 |
| 13 | 2.75 |
| 14 | 4.321 |
| 15 | 4.56 |

-continued

| Example | CatS IC$_{50}$ uM |
|---|---|
| 16 | 1.5 |
| 17 | 0.195 |
| 18 | 0.195 |
| 19 | 0.47 |
| 20 | 1.035 |
| 21 | 4.07 |
| 22 | 1.96 |
| 23 | 1.02 |
| 24 | 0.985 |
| 25 | 0.18 |
| 26 | 0.15 |
| 27 | 0.22 |
| 28 | 0.19 |
| 29 | 0.28 |
| 30 | 0.23 |
| 31 | 0.31 |
| 32 | 0.33 |
| 33 | 0.13 |
| 34 | 0.93 |
| 35 | 0.257 |
| 36 | 0.77 |
| 37 | 0.595 |
| 38 | 0.47 |
| 39 | 0.242 |
| 40 | 0.077 |
| 41 | 0.875 |
| 42 | 0.287 |
| 43 | 0.445 |
| 44 | 0.385 |
| 45 | 0.11 |
| 46 | 0.305 |
| 47 | 0.145 |
| 48 | 0.45 |
| 49 | 1.195 |
| 50 | 0.605 |
| 51 | 1.845 |
| 52 | 1.375 |
| 53 | 0.145 |
| 54 | 0.135 |
| 55 | 0.35 |
| 56 | 0.225 |
| 57 | 0.995 |
| 58 | 3.35 |
| 59 | 0.285 |
| 60 | 0.915 |
| 61 | 1.935 |
| 62 | 0.3 |
| 63 | 0.667 |
| 64 | 0.928 |
| 65 | 0.585 |
| 66 | 0.45 |
| 67 | 1.383 |
| 68 | 0.65 |
| 69 | 1.67 |
| 70 | 0.245 |
| 71 | 0.084 |
| 72 | 0.024 |
| 73 | 0.175 |
| 74 | 0.094 |
| 75 | 0.06 |
| 76 | 0.317 |
| 77 | 0.155 |
| 78 | 1.07 |
| 79 | 2.87 |
| 80 | 0.099 |
| 81 | 0.17 |

Example A

Film coated tablets containing the following ingredients can be manufactured in a conventional manner:

| Ingredients | Per tablet | |
|---|---|---|
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titan dioxide | 0.8 mg | 1.6 mg |

The active ingredient is sieved and mixed with microcrystalline cellulose and the mixture is granulated with a solution of polyvinylpyrrolidone in water. The granulate is then mixed with sodium starch glycolate and magnesium stearate and compressed to yield kernels of 120 or 350 mg respectively. The kernels are lacquered with an aq. solution/suspension of the above mentioned film coat.

Example B

Capsules containing the following ingredients can be manufactured in a conventional manner:

| Ingredients | Per capsule |
|---|---|
| Compound of formula (I) | 25.0 mg |
| Lactose | 150.0 mg |
| Maize starch | 20.0 mg |
| Talc | 5.0 mg |

The components are sieved and mixed and filled into capsules of size 2.

Example C

Injection solutions can have the following composition:

| | |
|---|---|
| Compound of formula (I) | 3.0 mg |
| Polyethylene glycol 400 | 150.0 mg |
| Acetic acid | q.s. ad pH 5.0 |
| Water for injection solutions | ad 1.0 ml |

The active ingredient is dissolved in a mixture of Polyethylene glycol 400 and water for injection (part). The pH is adjusted to 5.0 by addition of acetic acid. The volume is adjusted to 1.0 ml by addition of the residual amount of water. The solution is filtered, filled into vials using an appropriate overage and sterilized.

The invention claimed is:

1. A compound of formula (I)

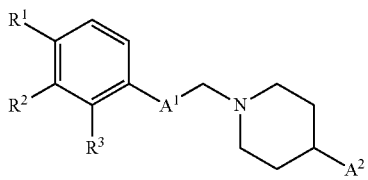

wherein

R¹ is haloalkylsulfonyl, haloalkyl, alkylsulfonyl, phenylalkylsulfonyl, halogen or alkyl;

R² is hydrogen or halogen;

R³ is hydrogen or halogen;

A¹ is 1H-imidazolyl optionally substituted with one or two substituents independently selected from alkyl, phenyl, phenylalkyl and alkoxyalkyl; and A² is heterocyclyl or substituted heterocyclyl, wherein heterocyclyl is oxodihydroquinazolinyl, oxodihydrobenzoimidazolyl, 1H-pyrrolopyridine, oxodihydroindolyl, benzoimidazol-1-yl, 3-oxo-4H-benzo[1,4]oxazinyl, oxo-1H-imidazolyl, benzo[d]isoxazolyl, oxo-4H-[1,2,4]triazolyl, oxo-5H-imidazopyridinyl or oxopiperidinyl and wherein substituted heterocyclyl is heterocyclyl substituted with one or two substituents independently selected from alkyl, halogen, alkoxycarbonylalkyl, alkoxyalkyl, pyrrolidinyl, hydroxyalkyl, alkylcarbonyloxyalkyl, alkylsulfonylalkyl, morpholinyl, aminocarbonylalkyl, alkylaminocarbonylalkyl, alkylpiperazinyl, halophenyl and carboxyalkyl;

or a pharmaceutically acceptable salt or ester thereof.

2. A compound according to claim 1, or a pharmaceutically acceptable salt or ester thereof, wherein R¹ is haloalkylsulfonyl, haloalkyl or alkylsulfonyl.

3. A compound according to claim 1, or a pharmaceutically acceptable salt or ester thereof, wherein R¹ is trifluoromethylsulfonyl, trifluoromethyl or methylsulfonyl.

4. A compound according to claim 1, or a pharmaceutically acceptable salt or ester thereof, wherein R² is hydrogen or chloro.

5. A compound according to claim 1, or a pharmaceutically acceptable salt or ester thereof, wherein R³ is hydrogen.

6. A compound according to claim 1, or a pharmaceutically acceptable salt or ester thereof, wherein A¹ is alkyl-1H-imidazolyl or dialkyl-1H-imidazolyl.

7. A compound according to claim 1, or a pharmaceutically acceptable salt or ester thereof, wherein A¹ is methyl-1H-imidazolyl, propyl-1H-imidazolyl or dimethyl-1H-imidazolyl.

8. A compound according to claim 1, or a pharmaceutically acceptable salt or ester thereof, wherein A² is oxodihydroquinazolinyl, alkyloxodihydrobenzoimidazolyl, (alkylpyrrolidinyl)oxodihydrobenzoimidazolyl or 1H-pyrrolopyridine.

9. A compound according to claim 1, or a pharmaceutically acceptable salt or ester thereof, wherein A² is oxodihydroquinazolinyl, methyloxodihydrobenzoimidazolyl, (methylpyrrolidinyl)oxodihydrobenzoimidazolyl or 1H-pyrrolopyridine.

10. A compound according to claim 1 selected from

3-{1-[5-Methyl-2-(4-trifluoromethanesulfonyl-phenyl)-1H-imidazol-4-ylmethyl]-piperidin-4-yl}-3,4-dihydro-1H-quinazolin-2-one;

1-Methyl-3-{1-[5-methyl-2-(4-trifluoromethanesulfonyl-phenyl)-1H-imidazol-4-ylmethyl]-piperidin-4-yl}-1,3-dihydro-benzoimidazol-2-one;

3-{1-[2-(3-Chloro-4-trifluoromethyl-phenyl)-5-methyl-1H-imidazol-4-ylmethyl]-piperidin-4-yl}-3,4-dihydro-1H-quinazolin-2-one;

3-{1-[1,5-Dimethyl-2-(4-trifluoromethyl-phenyl)-1H-imidazol-4-ylmethyl]-piperidin-4-yl}-3,4-dihydro-1H-quinazolin-2-one;

3-{1-[2-(4-Methanesulfonyl-phenyl)-5-methyl-1H-imidazol-4-ylmethyl]-piperidin-4-yl}-3,4-dihydro-1H-quinazolin-2-one 3-{1-[5-Methyl-2-(4-phenylmethanesulfonyl-phenyl)-1H-imidazol-4-ylmethyl]-piperidin-4-yl}-3,4-dihydro-1H-quinazolin-2-one;

3-{1-[2-(3-Chloro-4-trifluoromethyl-phenyl)-5-methyl-1H-imidazol-4-ylmethyl]-piperidin-4-yl}-7-fluoro-3,4-dihydro-1H-quinazolin-2-one;

(6-Chloro-3-{1-[5-methyl-2-(4-trifluoromethyl-phenyl)-1H-imidazol-4-ylmethyl]-piperidin-4-yl}-2-oxo-2,3-dihydro-benzoimidazol-1-yl)-acetic acid methyl ester;

1-(2-Methoxy-ethyl)-3-{1-[5-methyl-2-(4-trifluoromethyl-phenyl)-1H-imidazol-4-ylmethyl]-piperidin-4-yl}-3,4-dihydro-1H-quinazolin-2-one;

1-Methyl-3-{1-[5-methyl-2-(4-trifluoromethyl-phenyl)-1H-imidazol-4-ylmethyl]-piperidin-4-yl}-3,4-dihydro-1H-quinazolin-2-one;

3-{1-[2-(3-Fluoro-4-trifluoromethyl-phenyl)-5-methyl-1H-imidazol-4-ylmethyl]-piperidin-4-yl}-3,4-dihydro-1H-quinazolin-2-one;

5-Chloro-3-ethyl-1-{1-[5-methyl-2-(4-trifluoromethyl-phenyl)-1H-imidazol-4-ylmethyl]-piperidin-4-yl}-1,3-dihydro-benzoimidazol-2-one;

3-{1-[5-Methyl-2-(4-trifluoromethanesulfonyl-phenyl)-1H-imidazol-4-ylmethyl]-piperidin-4-yl}-1H-pyrrolo[3,2-c]pyridine;

1-Methyl-3-{1-[5-methyl-2-(4-phenylmethanesulfonyl-phenyl)-1H-imidazol-4-ylmethyl]-piperidin-4-yl}-1,3-dihydro-benzoimidazol-2-one;

1-{1-[2-(4-Methanesulfonyl-phenyl)-5-methyl-1H-imidazol-4-ylmethyl]-piperidin-4-yl}-3-methyl-1,3-dihydro-benzoimidazol-2-one;

7-Fluoro-3-{1-[5-methyl-2-(4-trifluoromethyl-phenyl)-1H-imidazol-4-ylmethyl]-piperidin-4-yl}-3,4-dihydro-1H-quinazolin-2-one;

1-{1-[5-Methyl-2-(4-trifluoromethyl-phenyl)-1H-imidazol-4-ylmethyl]-piperidin-4-yl}-6-pyrrolidin-1-yl-1,3-dihydro-benzoimidazol-2-one;

3-{1-[5-Methyl-2-(4-trifluoromethyl-phenyl)-1H-imidazol-4-ylmethyl]-piperidin-4-yl}-3,4-dihydro-1H-quinazolin-2-one;

5-Chloro-3-methyl-1-{1-[5-methyl-2-(4-trifluoromethyl-phenyl)-1H-imidazol-4-ylmethyl]-piperidin-4-yl}-1,3-dihydro-benzoimidazol-2-one;

6-Bromo-3-[1-[[2-[4(trifluoromethyl)phenyl]-1H-imidazol-5-yl]methyl]-4-piperidyl]-1,4-dihydroquinazolin-2-one;

5-Chloro-3-(2-methoxy-ethyl)-1-{1-[5-methyl-2-(4-trifluoromethyl-phenyl)-1H-imidazol-4-ylmethyl]-piperidin-4-yl}-1,3-dihydro-benzoimidazol-2-one;

3-{1-[5-Benzyl-2-(4-trifluoromethyl-phenyl)-1H-imidazol-4-ylmethyl]-piperidin-4-yl}-3,4-dihydro-1H-quinazolin-2-one 5-Chloro-3-(2-hydroxy-ethyl)-1-{1-[5-methyl-2-(4-trifluoromethyl-phenyl)-1H-imidazol-4-ylmethyl]-piperidin-4-yl}-1,3-dihydro-benzoimidazol-2-one;
1-{1-[2-(3-Chloro-4-trifluoromethyl-phenyl)-5-methyl-1H-imidazol-4-ylmethyl]-piperidin-4-yl}-3-methyl-1,3-dihydro-benzoimidazol-2-one;
5-Chloro-1-{1-[5-methyl-2-(4-trifluoromethyl-phenyl)-1H-imidazol-4-ylmethyl]-piperidin-4-yl}-1,3-dihydro-benzoimidazol-2-one;
1-{1-[1,5-Dimethyl-2-(4-trifluoromethyl-phenyl)-1H-imidazol-4-ylmethyl]-piperidin-4-yl}-3-methyl-1,3-dihydro-benzoimidazol-2-one;
5-Chloro-3-(2-methanesulfonyl-ethyl)-1-{1-[5-methyl-2-(4-trifluoromethyl-phenyl)-1H-imidazol-4-ylmethyl]-piperidin-4-yl}-1,3-dihydro-benzoimidazol-2-one;
Acetic acid 2-(6-chloro-3-{1-[5-methyl-2-(4-trifluoromethyl-phenyl)-1H-imidazol-4-ylmethyl]-piperidin-4-yl}-2-oxo-2,3-dihydro-benzoimidazol-1-yl)-ethyl ester;
1-Methyl-3-{1-[5-methyl-2-(4-trifluoromethyl-phenyl)-1H-imidazol-4-ylmethyl]-piperidin-4-yl}-1,3-dihydro-benzoimidazol-2-one;
3-{1-[2-(2-Chloro-4-trifluoromethyl-phenyl)-5-methyl-1H-imidazol-4-ylmethyl]-piperidin-4-yl}-3,4-dihydro-1H-quinazolin-2-one;
1-{1-[5-Methyl-2-(4-trifluoromethyl-phenyl)-1H-imidazol-4-ylmethyl]-piperidin-4-yl}-6-morpholin-4-yl-1,3-dihydro-benzoimidazol-2-one;
3-{1-[2-(3,4-Dichloro-phenyl)-5-methyl-1H-imidazol-4-ylmethyl]-piperidin-4-yl}-3,4-dihydro-1H-quinazolin-2-one;
3-{1-[5-Propyl-2-(4-trifluoromethyl-phenyl)-1H-imidazol-4-ylmethyl]-piperidin-4-yl}-3,4-dihydro-1H-quinazolin-2-one;
3-{1-[2-(3-Chloro-4-trifluoromethyl-phenyl)-5-methyl-1H-imidazol-4-ylmethyl]-piperidin-4-yl}-1H-pyrrolo[2,3-b]pyridine;
2-(6-Chloro-3-{1-[5-methyl-2-(4-trifluoromethyl-phenyl)-1H-imidazol-4-ylmethyl]-piperidin-4-yl}-2-oxo-2,3-dihydro-benzoimidazol-1-yl)-acetamide;
3-{1-[1-(2-Methoxy-ethyl)-5-methyl-2-(4-trifluoromethyl-phenyl)-1H-imidazol-4-ylmethyl]-piperidin-4-yl}-3,4-dihydro-1H-quinazolin-2-one;
2-(6-Chloro-3-{1-[5-methyl-2-(4-trifluoromethyl-phenyl)-1H-imidazol-4-ylmethyl]-piperidin-4-yl}-2-oxo-2,3-dihydro-benzoimidazol-1-yl)-N-methyl-acetamide;
3-{1-[5-(2-Methoxy-ethyl)-2-(4-trifluoromethyl-phenyl)-1H-imidazol-4-ylmethyl]-piperidin-4-yl}-3,4-dihydro-1H-quinazolin-2-one;
1-{1-[2-(3-Fluoro-4-trifluoromethyl-phenyl)-5-methyl-1H-imidazol-4-ylmethyl]-piperidin-4-yl}-3-methyl-1,3-dihydro-benzoimidazol-2-one;
1-{1-[5-Methyl-2-(4-trifluoromethyl-phenyl)-1H-imidazol-4-ylmethyl]-piperidin-4-yl}-1,3-dihydro-benzoimidazol-2-one;
5-Chloro-1-{1-[5-methyl-2-(4-trifluoromethyl-phenyl)-1H-imidazol-4-ylmethyl]-piperidin-4-yl}-1,3-dihydro-indol-2-one;
1-{1-[5-Methyl-2-(4-trifluoromethyl-phenyl)-1H-imidazol-4-ylmethyl]-piperidin-4-yl}-1H-benzoimidazole;
3-{1-[2-(3,4-Dichloro-phenyl)-5-methyl-1H-imidazol-4-ylmethyl]-piperidin-4-yl}-7-fluoro-3,4-dihydro-1H-quinazolin-2-one;
6-(4-Methyl-piperazin-1-yl)-1-{1-[5-methyl-2-(4-trifluoromethyl-phenyl)-1H-imidazol-4-ylmethyl]-piperidin-4-yl}-1,3-dihydro-benzoimidazol-2-one;
4-{1-[5-Methyl-2-(4-trifluoromethyl-phenyl)-1H-imidazol-4-ylmethyl]-piperidin-4-yl}-4H-benzo[1,4]oxazin-3-one;
3-{1-[5-Methyl-2-(4-trifluoromethyl-phenyl)-1H-imidazol-4-ylmethyl]-piperidin-4-yl}-1H-pyrrolo[2,3-b]pyridine;
5-(4-Bromophenyl)-3-[1-[[4-methyl-2-[4-(trifluoromethyl)phenyl]-1H-imidazol-5-yl]methyl]-4-piperidyl]-1H-imidazol-2-one;
6-Fluoro-3-{1-[5-methyl-2-(4-trifluoromethyl-phenyl)-1H-imidazol-4-ylmethyl]-piperidin-4-yl}-benzo[d]isoxazole;
3-{1-[2-(4-Chloro-3-fluoro-phenyl)-5-methyl-1H-imidazol-4-ylmethyl]-piperidin-4-yl}-3,4-dihydro-1H-quinazolin-2-one;
3-{1-[5-Methyl-2-(4-trifluoromethyl-phenyl)-1H-imidazol-4-ylmethyl]-piperidin-4-yl}-1H-pyrrolo[3,2-c]pyridine;
1-{1-[5-Methyl-2-(4-trifluoromethyl-phenyl)-1H-imidazol-4-ylmethyl]-piperidin-4-yl}-1,3-dihydro-indol-2-one;
1-{1-[2-(3,4-Dichloro-phenyl)-5-methyl-1H-imidazol-4-ylmethyl]-piperidin-4-yl}-3-methyl-1,3-dihydro-benzoimidazol-2-one;
1-{1-[2-(2-Chloro-4-trifluoromethyl-phenyl)-1H-imidazol-4-ylmethyl]-piperidin-4-yl}-3-methyl-1,3-dihydro-benzoimidazol-2-one;
1-Methyl-3-{1-[5-propyl-2-(4-trifluoromethyl-phenyl)-1H-imidazol-4-ylmethyl]-piperidin-4-yl}-1,3-dihydro-benzoimidazol-2-one;
Sodium (6-chloro-3-{1-[5-methyl-2-(4-trifluoromethyl-phenyl)-1H-imidazol-4-ylmethyl]-piperidin-4-yl}-2-oxo-2,3-dihydro-benzoimidazol-1-yl)-acetate;
1-Methyl-3-{1-[5-phenyl-2-(4-trifluoromethyl-phenyl)-1H-imidazol-4-ylmethyl]-piperidin-4-yl}-1,3-dihydro-benzoimidazol-2-one;
3-{1-[2-(2,4-Dichloro-phenyl)-5-methyl-1H-imidazol-4-ylmethyl]-piperidin-4-yl}-3,4-dihydro-1H-quinazolin-2-one;
5-Chloro-1-{1-[2-(3-chloro-4-methyl-phenyl)-5-methyl-1H-imidazol-4-ylmethyl]-piperidin-4-yl}-1,3-dihydro-benzoimidazol-2-one;
5-Chloro-1-{1-[2-(4-chloro-phenyl)-5-methyl-1H-imidazol-4-ylmethyl]-piperidin-4-yl}-1,3-dihydro-benzoimidazol-2-one;
3-(1-{5-Methyl-2-[4-(2-methyl-propane-1-sulfonyl)-phenyl]-1H-imidazol-4-ylmethyl}-piperidin-4-yl)-3,4-dihydro-1H-quinazolin-2-one;
3-{1-[2-(3,4-Dichloro-phenyl)-5-methyl-1H-imidazol-4-ylmethyl]-piperidin-4-yl}-1H-pyrrolo[2,3-b]pyridine;
5-(4-Bromophenyl)-2-[1-[[2-[4-(trifluoromethyl)phenyl]-1H-imidazol-5-yl]methyl]-4-piperidyl]-4H-1,2,4-triazol-3-one;
1-{1-[2-(4-Chloro-3-fluoro-phenyl)-5-methyl-1H-imidazol-4-ylmethyl]-piperidin-4-yl}-3-methyl-1,3-dihydro-benzoimidazol-2-one;
3-{1-[5-(2-Methoxy-ethyl)-2-(4-trifluoromethyl-phenyl)-1H-imidazol-4-ylmethyl]-piperidin-4-yl}-1H-pyrrolo[3,2-c]pyridine;
5-Chloro-1-{1-[2-(3-fluoro-4-methyl-phenyl)-5-methyl-1H-imidazol-4-ylmethyl]-piperidin-4-yl}-1,3-dihydro-benzoimidazol-2-one;
1-Methyl-3-{1-[5-methyl-2-(4-trifluoromethyl-phenyl)-oxazol-4-ylmethyl]-piperidin-4-yl}-1,3-dihydro-benzoimidazol-2-one;

1-[1-[[4-Methyl-2-[4-(trifluoromethyl)phenyl]-1H-imidazol-5-yl]methyl]-4-piperidyl]-5H-imidazo[4,5-c]pyridin-4-one;
1-Methyl-3-(1-{5-methyl-2-[4-(2-methyl-propane-1-sulfonyl)-phenyl]-1H-imidazol-4-ylmethyl}-piperidin-4-yl)-1,3-dihydro-benzoimidazol-2-one;
1-[1-[[4-Methyl-2-[4-(trifluoromethyl)phenyl]-1H-imidazol-5-yl]methyl]-4-piperidyl]piperidin-2-one;
1-{1-[2-(2,4-Dichloro-phenyl)-5-methyl-1H-imidazol-4-ylmethyl]-piperidin-4-yl}-3-methyl-1,3-dihydro-benzoimidazol-2-one;
5-Chloro-1-[1-(5-methyl-2-p-tolyl-1H-imidazol-4-ylmethyl)-piperidin-4-yl]-1,3-dihydro-benzoimidazol-2-one;
1-[1-[[2-[4-(Trifluoromethyl)phenyl]-1H-imidazol-5-yl]methyl]-4-piperidyl]-5H-imidazo[4,5-c]pyridin-4-one; and
5-(4-Bromophenyl)-3-[1-[[2-[4-(trifluoromethyl)phenyl]-1H-imidazol-5-yl]methyl]-4-piperidyl]-1H-imidazol-2-one;
or a pharmaceutically acceptable salt or ester thereof.

11. A compound according to claim 1 selected from
3-{1-[5-Methyl-2-(4-trifluoromethanesulfonyl-phenyl)-1H-imidazol-4-ylmethyl]-piperidin-4-yl}-3,4-dihydro-1H-quinazolin-2-one;
1-Methyl-3-{1-[5-methyl-2-(4-trifluoromethanesulfonyl-phenyl)-1H-imidazol-4-ylmethyl]-piperidin-4-yl}-1,3-dihydro-benzoimidazol-2-one;
3-{1-[2-(3-Chloro-4-trifluoromethyl-phenyl)-5-methyl-1H-imidazol-4-ylmethyl]-piperidin-4-yl}-3,4-dihydro-1H-quinazolin-2-one;
3-{1-[1,5-Dimethyl-2-(4-trifluoromethyl-phenyl)-1H-imidazol-4-ylmethyl]-piperidin-4-yl}-3,4-dihydro-1H-quinazolin-2-one;
3-{1-[2-(4-Methanesulfonyl-phenyl)-5-methyl-1H-imidazol-4-ylmethyl]-piperidin-4-yl}-3,4-dihydro-1H-quinazolin-2-one;
3-{1-[5-Methyl-2-(4-trifluoromethanesulfonyl-phenyl)-1H-imidazol-4-ylmethyl]-piperidin-4-yl}-1H-pyrrolo[3,2-c]pyridine;
1-{1-[2-(4-Methanesulfonyl-phenyl)-5-methyl-1H-imidazol-4-ylmethyl]-piperidin-4-yl}-3-methyl-1,3-dihydro-benzoimidazol-2-one;
3-{1-[5-Propyl-2-(4-trifluoromethyl-phenyl)-1H-imidazol-4-ylmethyl]-piperidin-4-yl}-3,4-dihydro-1H-quinazolin-2-one;
6-(4-Methyl-piperazin-1-yl)-1-{1-[5-methyl-2-(4-trifluoromethyl-phenyl)-1H-imidazol-4-ylmethyl]-piperidin-4-yl}-1,3-dihydro-benzoimidazol-2-one; and
3-{1-[5-Methyl-2-(4-trifluoromethyl-phenyl)-1H-imidazol-4-ylmethyl]-piperidin-4-yl}-1H-pyrrolo[3,2-c]pyridine;
or a pharmaceutically acceptable salt or ester thereof.

12. A process for the manufacture of a compound according to claim 1, or a pharmaceutically acceptable salt or ester thereof, comprising one of the following steps:
(a) the reaction of a compound of formula (II)

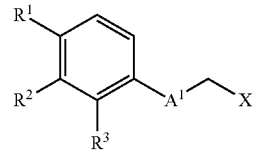

(II)

in the presence of a compound of formula (III)

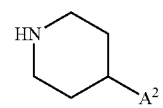

(III)

and a base; or
(b) the reaction of a compound of formula (IV)

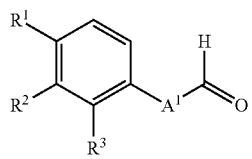

(IV)

in the presence of a compound of formula (III) as defined above and a reducing agent;
wherein X is Cl, Br, I or —OSO$_2$R; and R is methyl or p-toluyl.

13. A compound according to claim 1, or a pharmaceutically acceptable salt or ester thereof, when manufactured according to a process of claim 12.

14. A pharmaceutical composition comprising a compound according to claim 1, or a pharmaceutically acceptable salt or ester thereof, and a therapeutically inert carrier.

* * * * *